US011292836B2

(12) United States Patent
Tsun et al.

(10) Patent No.: US 11,292,836 B2
(45) Date of Patent: Apr. 5, 2022

(54) ANTI-CD47 ANTIBODIES AND USES THEREOF

(71) Applicant: INNOVENT BIOLOGICS (SUZHOU) CO., LTD., Jiangsu (CN)

(72) Inventors: Andy Tsun, Jiangsu (CN); Dandan Liu, Jiangsu (CN); Bingliang Chen, Jiangsu (CN); Junjian Liu, Jiangsu (CN)

(73) Assignee: INNOVENT BIOLOGICS (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 16/473,867

(22) PCT Filed: Aug. 28, 2018

(86) PCT No.: PCT/CN2018/102752
§ 371 (c)(1),
(2) Date: Jun. 26, 2019

(87) PCT Pub. No.: WO2019/042285
PCT Pub. Date: Mar. 7, 2019

(65) Prior Publication Data
US 2020/0181259 A1    Jun. 11, 2020

(30) Foreign Application Priority Data
Aug. 29, 2017    (CN) .......................... 201710759828.9

(51) Int. Cl.
| | |
|---|---|
| *A61K 39/00* | (2006.01) |
| *G01N 33/53* | (2006.01) |
| *C07H 21/04* | (2006.01) |
| *C12P 21/06* | (2006.01) |
| *C12N 15/87* | (2006.01) |
| *C12N 15/74* | (2006.01) |
| *C07K 16/00* | (2006.01) |
| *C07K 16/46* | (2006.01) |
| *C07K 16/28* | (2006.01) |
| *A61P 35/00* | (2006.01) |
| *G01N 33/577* | (2006.01) |

(52) U.S. Cl.
CPC .......... *C07K 16/2803* (2013.01); *A61P 35/00* (2018.01); *G01N 33/577* (2013.01); *A61K 2039/505* (2013.01); *C07K 2317/21* (2013.01); *C07K 2317/24* (2013.01); *C07K 2317/35* (2013.01); *C07K 2317/55* (2013.01); *C07K 2317/565* (2013.01); *C07K 2317/92* (2013.01); *G01N 2333/70503* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,101,719 | B2 | 1/2012 | Kikuchi et al. |
| 8,236,313 | B2 | 8/2012 | Isenberg et al. |
| 8,562,997 | B2 | 10/2013 | Jaiswal et al. |
| 8,758,750 | B2 | 6/2014 | Weissman et al. |
| 8,759,025 | B2 | 6/2014 | Kikuchi et al. |
| 8,951,527 | B2 | 2/2015 | Isenberg et al. |
| 9,017,675 | B2 | 4/2015 | Liu et al. |
| 9,045,541 | B2 | 6/2015 | Eckelman et al. |
| 9,221,908 | B2 | 12/2015 | Frazier et al. |
| 9,352,037 | B2 | 5/2016 | van den Berg |
| 9,382,320 | B2 | 7/2016 | Liu et al. |
| 9,399,682 | B2 | 7/2016 | Jaiswal et al. |
| 9,518,116 | B2 | 12/2016 | Frazier et al. |
| 9,518,117 | B2 | 12/2016 | Frazier et al. |
| 9,605,076 | B2 | 3/2017 | Jaiswal et al. |
| 9,611,329 | B2 | 4/2017 | Jaiswal et al. |
| 2015/0183874 | A1 | 7/2015 | Liu et al. |
| 2015/0238604 | A1 | 8/2015 | Eckelman et al. |
| 2016/0304609 | A1 | 10/2016 | Liu et al. |
| 2020/0377593 | A1* | 12/2020 | Liu .......................... A61P 35/02 |

FOREIGN PATENT DOCUMENTS

| | | |
|---|---|---|
| CN | 104271757 A | 1/2015 |
| CN | 105101997 A | 11/2015 |
| CN | 105102479 A | 11/2015 |
| CN | 105121467 A | 12/2015 |
| CN | 103665165 B | 2/2016 |
| CN | 106084052 A | 11/2016 |
| CN | 106117354 A | 11/2016 |

(Continued)

OTHER PUBLICATIONS

Wang et al. Novel fully human anti-CD47 antibodies stimulate phagocytosis and promote elimination of AML cells. J Cell Physiol. 2021;236:4470-4481. (Year: 2021).*
Examination Report No. 1 in Australian application AU2018325845 dated Apr. 23, 2020.
Sick et al., Activation of CD47 receptors causes proliferation of human astrocytoma but not normal astrocytes via an Akt-dependent pathway, Glia. 2011, 59(2): 308-19.
Pettersen et al., CD47 signals T cell death, J. Immunol., 1999, 162 (12): 7031-40.
Xu et al., Effect of CD47 on preventing and Treating Tumours, Guangdong Medical Journal., vol. 35, No.(18), 2014, pp. 2945-2947.
Yuan et al., Research Advances in the Relationship Between CD47 and Breast Cancer, Chinese Journal of Histochemistry and Cytochemistry., vol. 25, No. (4), 2016, pp. 371-374.

(Continued)

*Primary Examiner* — Maher M Haddad
(74) *Attorney, Agent, or Firm* — Leason Ellis, LLP

(57) ABSTRACT

The present invention is directed to a novel antibody against CD47 and the antibody fragments thereof and a composition comprising the antibody or antibody fragments thereof. The present invention relates further to a nucleic acid encoding the antibodies or antibody fragments thereof and host cells comprise the same, as well as the relevant use of the same. In addition, the present invention is also directed to the use of these antibodies and antibody fragments in the therapy and diagnosis.

20 Claims, 7 Drawing Sheets

Specification includes a Sequence Listing.

(56) References Cited

FOREIGN PATENT DOCUMENTS

| EP | 1693385 A1 | 8/2006 |
|---|---|---|
| EP | 2282772 B1 | 1/2014 |
| EP | 2242512 B1 | 4/2016 |
| EP | 2569013 B1 | 11/2016 |
| JP | 2013-534409 A | 9/2013 |
| KR | 1020060121150 | 11/2006 |
| WO | 2005/044857 A1 | 5/2005 |
| WO | 2009/091547 A1 | 7/2009 |
| WO | 2014/094122 A1 | 6/2014 |
| WO | 2015/105995 A2 | 7/2015 |
| WO | 2017049251 A2 | 3/2017 |
| WO | 2019/129054 A1 | 7/2019 |
| WO | 2019184912 | 10/2019 |

OTHER PUBLICATIONS

International Search Report in corresponding PCT application PCT/CN2018/102752 dated Nov. 19, 2018.
International Search Report and Written Opinion in corresponding PCT application PCT/CN2018/102752 dated Nov. 19, 2018.
Zeng et al.: "A fully human anti-C047 blocking antibody with therapeutic potential for cancer", Oncotarget, vol. 7, No. 50, 2016, pp. 83040-83050.
Uno et al.: "Antitumor activity of a monoclonal antibody against CD47 in xenograft models of human leukemia": Oncol Rep 2007; 17:1189-94.
Kikuchi et al.: "A bivalent single-chain Fv fragment against CD47 induces apoptosis for leukemic cells": Biochem Biophys Res Commun 2004315: 912-8.

\* cited by examiner

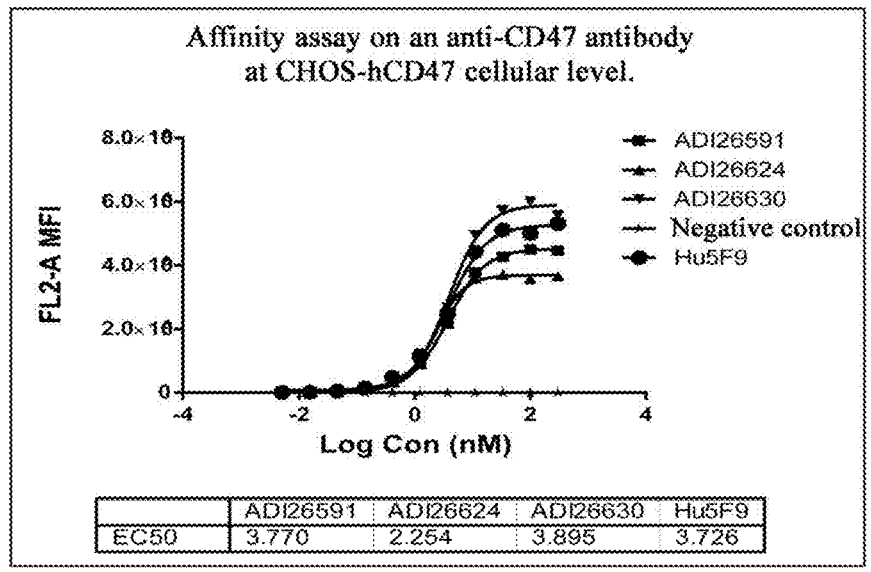
Fig. 1. Affinity assay with flow cytometery on an anti-CD47 antibody in IgG1 format produced in yeasts at the cellular level.
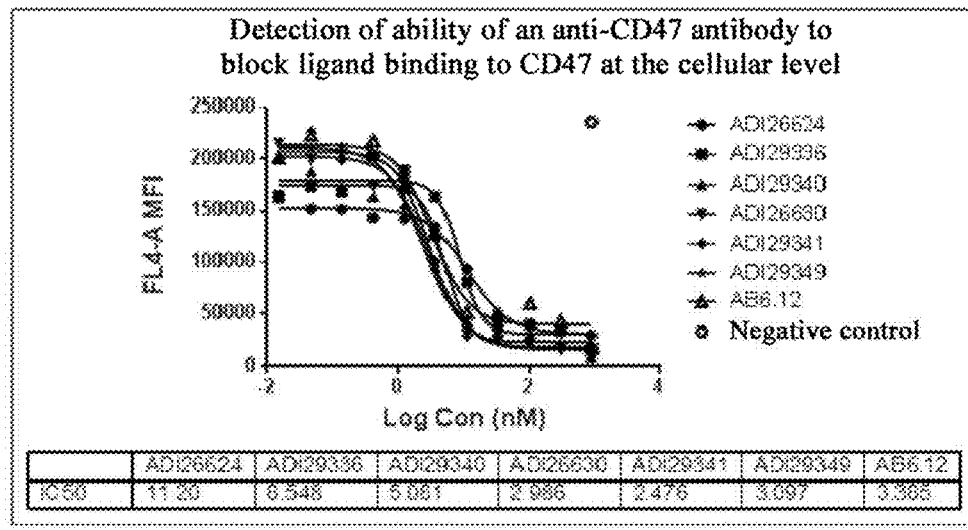
Fig. 2. Blocking of SIRPα binding to a CD47 expressed on CHO cells by the present antibody in IgG1 format produced in yeast cells as assayed with flow cytometery.

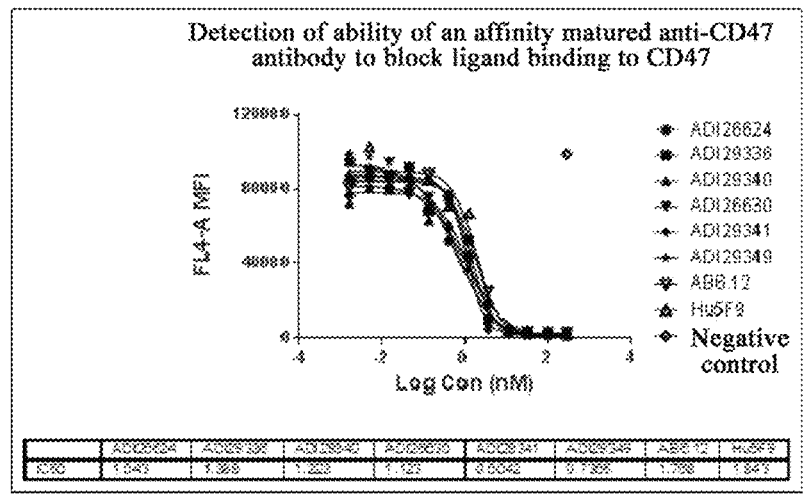

Fig. 3. Blocking of SIRPα binding to a CD47 expressed on CHO cells by the present antibody in IgG4 format produced in CHO cells as assayed with flow cytometery.

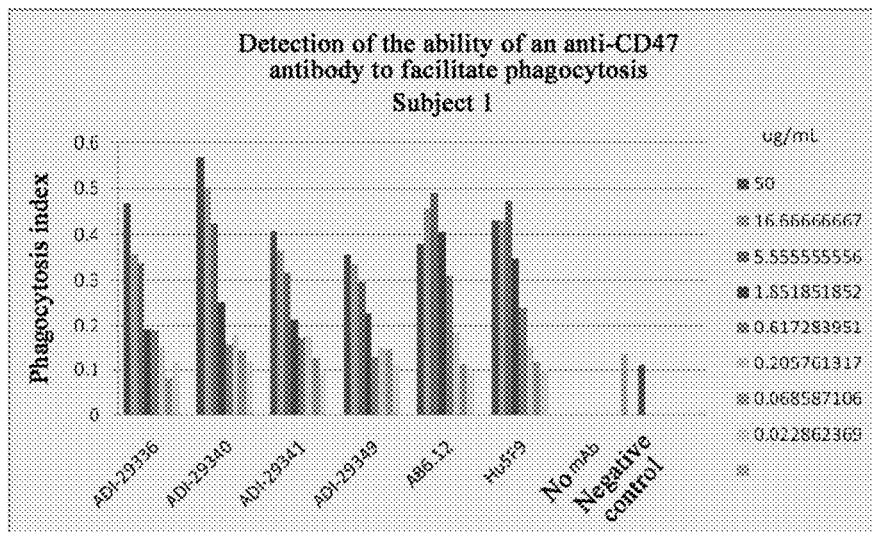

Fig. 4. Detection of the ability of the present antibody in IgG1 format produced in yeast cells to facilitate phagocytosis of tumor cells by macrophages, the antibody including the antibody-affinity-matured antibodies ADI-29336, ADI-29340, ADI-29341 and ADI-29349 in IgG1 format produced in yeast cells.

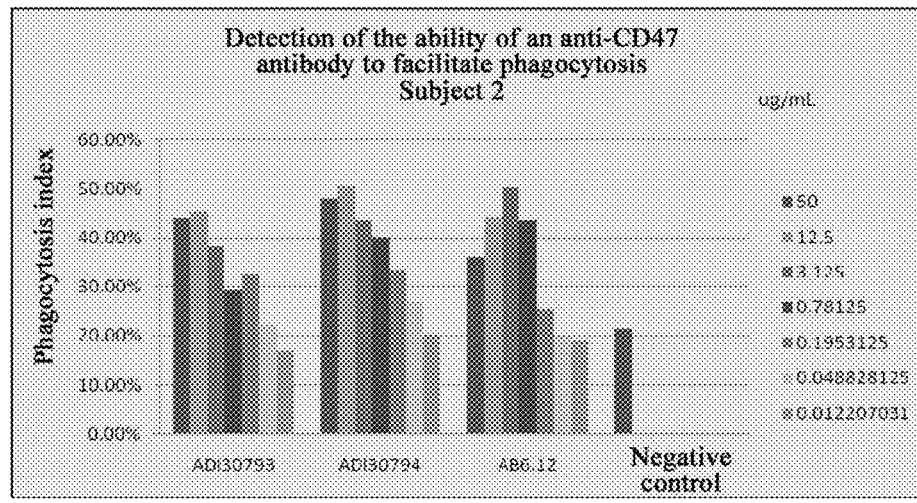
Fig. 5. Detection of the ability of the present IgG1 antibody produced in yeast cells to facilitate phagocytosis of tumor cells by macrophages, the antibody including ADI-30793 and ADI-30794 in IgG1 format produced in yeast cells.
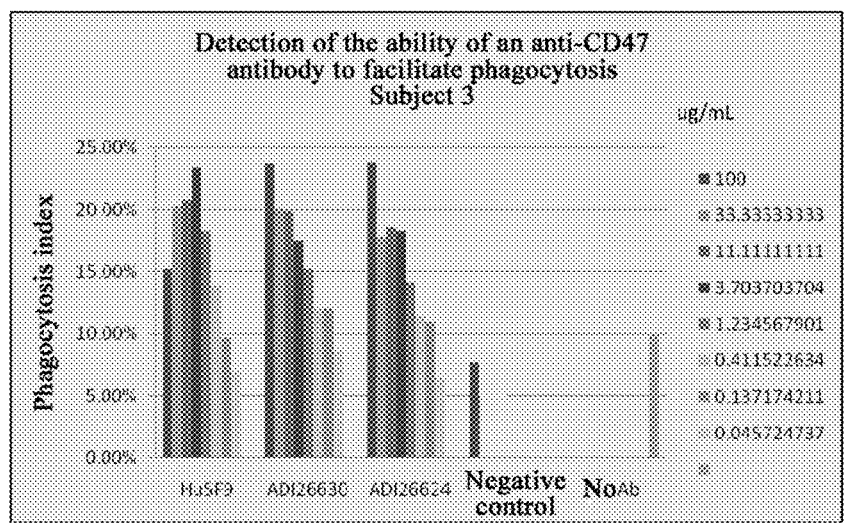
Fig. 6. Detection of the ability of the present antibody in IgG4 format produced in CHO cells to facilitate phagocytosis of tumor cells by macrophages.

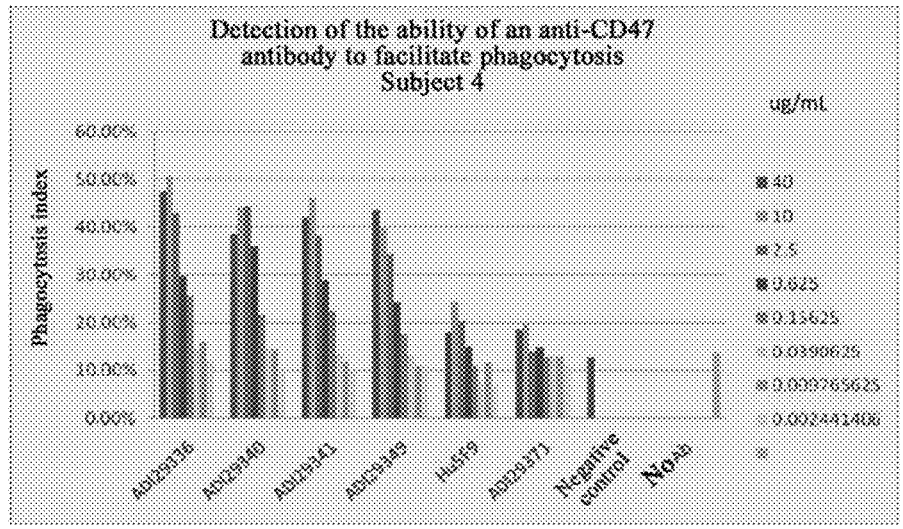
Fig. 7. Detection of the ability of the present antibody in IgG4 format produced in CHO cells to facilitate phagocytosis of tumor cells by macrophages. Include are ADI-29336, ADI-29340, ADI-29341 and ADI-29349 and ADI-29371.
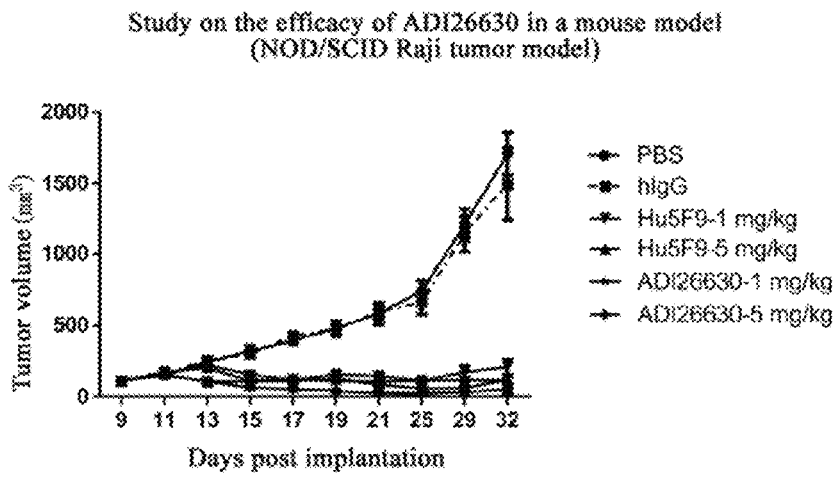
Fig. 8A: Study on the anti-tumor activity of the present antibody ADI-26630 in IgG4 format produced in CHO cells in a mouse model (NOD/SCID Raji tumor model).

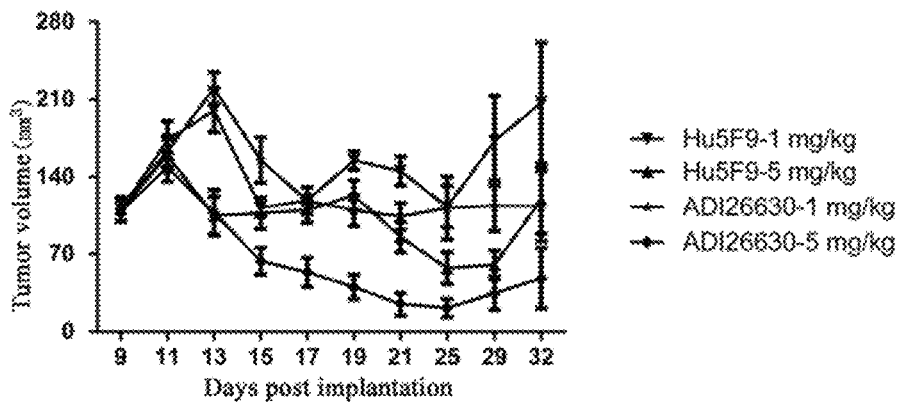
Fig. 8B Study on the anti-tumor activity of the present antibody ADI-26630 in IgG4 format produced in CHO cells in a mouse model (NOD/SCID Raji tumor model), Fig 8B is an enlarged partial view of Fig. 8A.
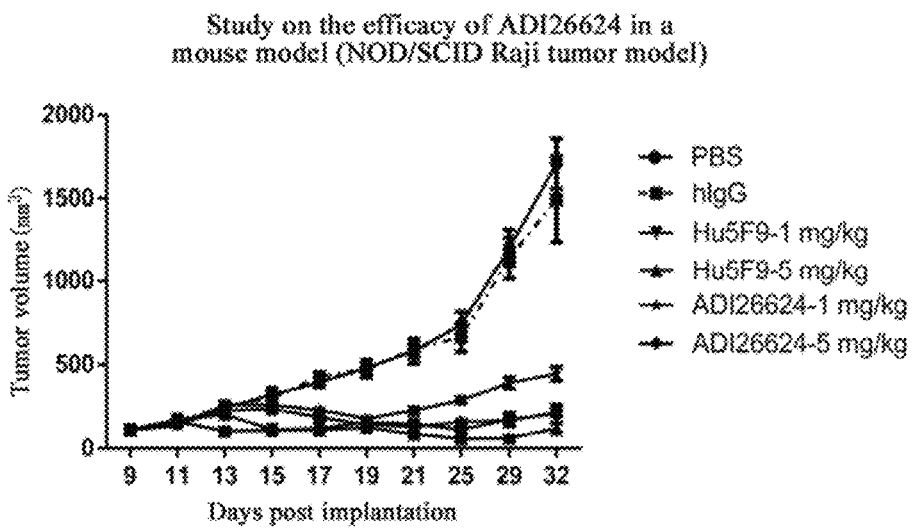
Fig. 9: Study on the anti-tumor activity of the presentantibody ADI-26624 in IgG4 format produced in CHO cells in a mouse model (NOD/SCID Raji tumor model).

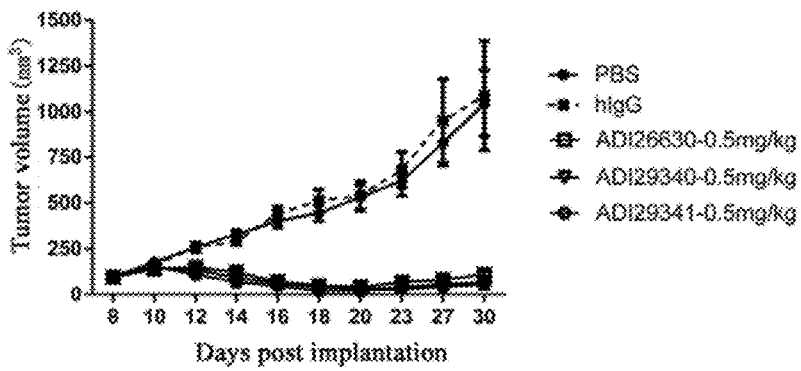
Fig. 10: Study on the anti-tumor activity of the present antibodies ADI-26630, ADI29340 and ADI29341 in IgG4 format produced in CHO cells at a dosage of 0.5 mg/kg in a mouse model (NOD/SCID Raji tumor model).
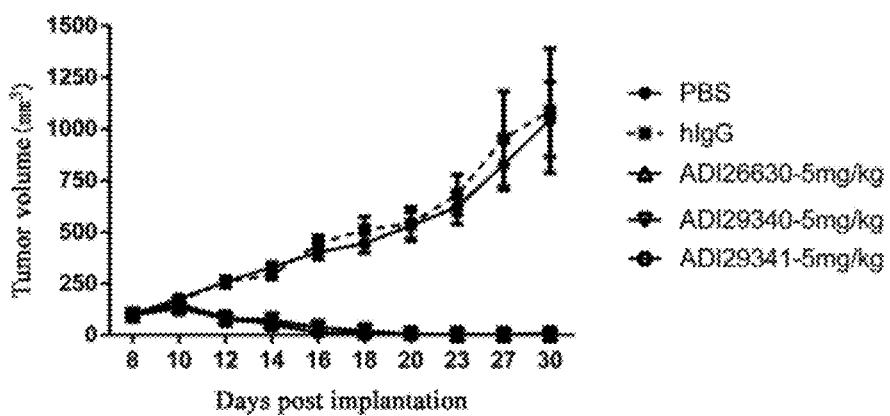
Fig. 11: Study on the anti-tumor activity of the present antibodies ADI-26630, ADI29340 and ADI29341 in IgG4 format produced in CHO cells at a dosage of 5 mg/kg in a mouse model (NOD/SCID Raji tumor model).

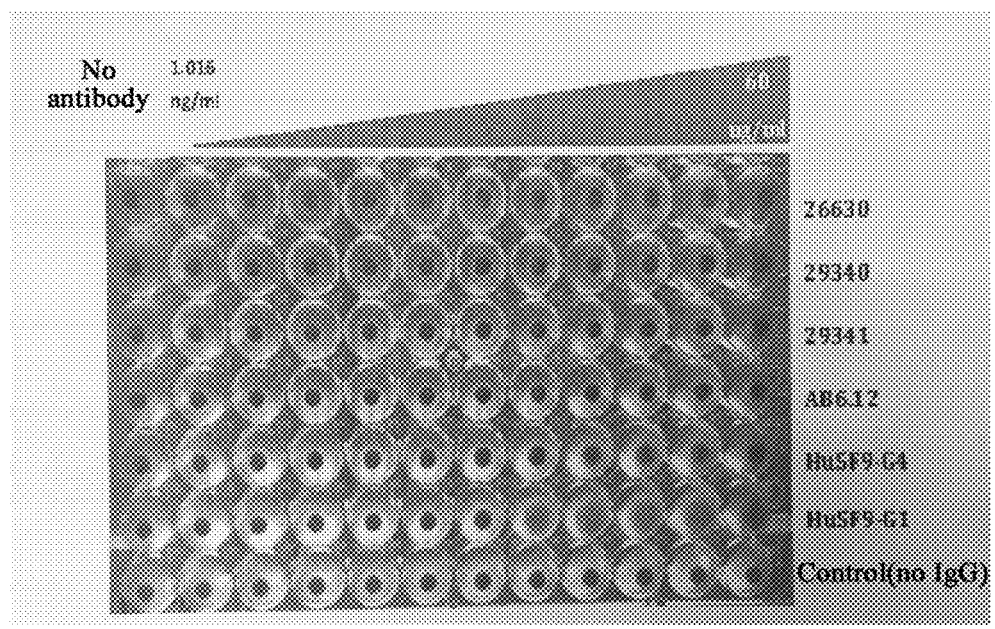
Fig. 12: Result of detecting the activity of an anti-CD47 antibody of the invention to facilitate RBC agglutination activity.

SEQUENCE LISTING

<160> NUMBER OF SEQ ID NOS: 107

<210> SEQ ID NO 1
<211> LENGTH: 9
<212> TYPE: PRT
<213> ORGANISM: artificial sequence
<220> FEATURE:
<223> OTHER INFORMATION: synthetic

<400> SEQUENCE: 1

Gly Ser Ile Ser Ser Tyr Tyr Trp Ser
1               5

<210> SEQ ID NO 2
<211> LENGTH: 9
<212> TYPE: PRT
<213> ORGANISM: artificial sequence
<220> FEATURE:
<223> OTHER INFORMATION: synthetic

<400> SEQUENCE: 2

Gly Ser Ile Ser Asn Tyr Tyr Trp Ser
1               5

<210> SEQ ID NO 3
<211> LENGTH: 9
<212> TYPE: PRT
<213> ORGANISM: artificial sequence
<220> FEATURE:
<223> OTHER INFORMATION: synthetic

<400> SEQUENCE: 3

Gly Ser Ile Asp Tyr Tyr Tyr Trp Ser
1               5

<210> SEQ ID NO 4
<211> LENGTH: 9
<212> TYPE: PRT
<213> ORGANISM: artificial sequence
<220> FEATURE:
<223> OTHER INFORMATION: synthetic

<400> SEQUENCE: 4

Gly Ser Ile Glu His Tyr Tyr Trp Ser
1               5

<210> SEQ ID NO 5
<211> LENGTH: 9
<212> TYPE: PRT
<213> ORGANISM: artificial sequence
<220> FEATURE:
<223> OTHER INFORMATION: synthetic

<400> SEQUENCE: 5

Gly Ser Ile Asp His Tyr Tyr Trp Ser
1               5

<210> SEQ ID NO 6
<211> LENGTH: 9
<212> TYPE: PRT
<213> ORGANISM: artificial sequence
<220> FEATURE:
<223> OTHER INFORMATION: synthetic

<400> SEQUENCE: 6

Phe Thr Phe Ser Ser Tyr Ala Met Ser
1               5

<210> SEQ ID NO 7
<211> LENGTH: 9
<212> TYPE: PRT
<213> ORGANISM: artificial sequence
<220> FEATURE:
<223> OTHER INFORMATION: synthetic

<400> SEQUENCE: 7

Phe Thr Phe Gly Asn Tyr Ala Met Ser
1               5

<210> SEQ ID NO 8
<211> LENGTH: 9
<212> TYPE: PRT
<213> ORGANISM: artificial sequence
<220> FEATURE:
<223> OTHER INFORMATION: synthetic

<400> SEQUENCE: 8

Phe Thr Phe Asp Ser Tyr Ala Met Thr
1               5

<210> SEQ ID NO 9
<211> LENGTH: 16
<212> TYPE: PRT
<213> ORGANISM: artificial sequence
<220> FEATURE:
<223> OTHER INFORMATION: synthetic

<400> SEQUENCE: 9

Tyr Ile Tyr Tyr Ser Gly Ser Thr Asn Tyr Asn Pro Ser Leu Lys Ser
1               5                   10                  15

<210> SEQ ID NO 10
<211> LENGTH: 16
<212> TYPE: PRT
<213> ORGANISM: artificial sequence
<220> FEATURE:
<223> OTHER INFORMATION: synthetic

<400> SEQUENCE: 10

Thr Ile Tyr Tyr Ser Gly Ser Thr Arg Tyr Asn Pro Ser Leu Lys Ser
1               5                   10                  15

<210> SEQ ID NO 11
<211> LENGTH: 16
<212> TYPE: PRT
<213> ORGANISM: artificial sequence
<220> FEATURE:
<223> OTHER INFORMATION: synthetic

<400> SEQUENCE: 11

Tyr Ile Tyr Tyr Ser Gly Ser Thr Gly Tyr Asn Pro Ser Leu Lys Ser
1               5                   10                  15

<210> SEQ ID NO 12
<211> LENGTH: 16
<212> TYPE: PRT
<213> ORGANISM: artificial sequence
<220> FEATURE:
<223> OTHER INFORMATION: synthetic

<400> SEQUENCE: 12

Tyr Ile Tyr Tyr Ser Gly Ser Thr Glu Tyr Asn Pro Ser Leu Lys Ser
1               5                   10                  15

<210> SEQ ID NO 13
<211> LENGTH: 17
<212> TYPE: PRT
<213> ORGANISM: artificial sequence
<220> FEATURE:
<223> OTHER INFORMATION: synthetic

<400> SEQUENCE: 13

Ala Ile Ser Gly Ser Gly Gly Ser Thr Tyr Tyr Ala Asp Ser Val Lys
1               5                   10                  15

Gly

<210> SEQ ID NO 14
<211> LENGTH: 16
<212> TYPE: PRT
<213> ORGANISM: artificial sequence
<220> FEATURE:
<223> OTHER INFORMATION: synthetic

<400> SEQUENCE: 14

Met Ile Ser Gly Gly Gly Ser Thr Tyr Tyr Ala Asp Ser Val Lys Gly
1               5                   10                  15

<210> SEQ ID NO 15
<211> LENGTH: 17
<212> TYPE: PRT
<213> ORGANISM: artificial sequence
<220> FEATURE:
<223> OTHER INFORMATION: synthetic

<400> SEQUENCE: 15

Val Ile Ser Gly Ser Gly Gly Lys Thr Tyr Tyr Ala Asp Ser Val Lys
1               5                   10                  15

Gly

<210> SEQ ID NO 16
<211> LENGTH: 17
<212> TYPE: PRT
<213> ORGANISM: artificial sequence
<220> FEATURE:
<223> OTHER INFORMATION: synthetic

<400> SEQUENCE: 16

Ala Ile Ser Gly Ser Gly Gly Lys Thr Tyr Tyr Ala Asp Ser Val Lys
1               5                   10                  15

Gly

<210> SEQ ID NO 17
<211> LENGTH: 9
<212> TYPE: PRT
<213> ORGANISM: artificial sequence
<220> FEATURE:
<223> OTHER INFORMATION: synthetic

<400> SEQUENCE: 17

Ala Arg Gly Lys Ser Ala Phe Asp Pro
1               5

<210> SEQ ID NO 18
<211> LENGTH: 9
<212> TYPE: PRT
<213> ORGANISM: artificial sequence
<220> FEATURE:
<223> OTHER INFORMATION: synthetic

<400> SEQUENCE: 18

Ala Arg Gly Lys Ser Ala Phe Asn Pro
1               5

<210> SEQ ID NO 19
<211> LENGTH: 9
<212> TYPE: PRT
<213> ORGANISM: artificial sequence
<220> FEATURE:
<223> OTHER INFORMATION: synthetic

<400> SEQUENCE: 19

Ala Arg Gly Lys Thr Gly Ser Ala Ala
1               5

<210> SEQ ID NO 20
<211> LENGTH: 11
<212> TYPE: PRT
<213> ORGANISM: artificial sequence
<220> FEATURE:
<223> OTHER INFORMATION: synthetic

<400> SEQUENCE: 20

Ala Lys Thr Pro Ile Tyr Tyr Gly Phe Asp Leu
1               5                   10

<210> SEQ ID NO 21
<211> LENGTH: 11
<212> TYPE: PRT
<213> ORGANISM: artificial sequence
<220> FEATURE:
<223> OTHER INFORMATION: synthetic

<400> SEQUENCE: 21

Ala Lys Thr His Leu Tyr Tyr Gly Phe Asp Leu
1               5                   10

<210> SEQ ID NO 22
<211> LENGTH: 11
<212> TYPE: PRT
<213> ORGANISM: artificial sequence
<220> FEATURE:
<223> OTHER INFORMATION: synthetic

<400> SEQUENCE: 22

Ala Lys Thr Ala Ile Tyr Tyr Gly Phe Asp Leu
1               5                   10

<210> SEQ ID NO 23
<211> LENGTH: 11
<212> TYPE: PRT
<213> ORGANISM: artificial sequence
<220> FEATURE:
<223> OTHER INFORMATION: synthetic

<400> SEQUENCE: 23

Arg Ala Ser Gln Gly Ile Ser Arg Trp Leu Ala
1               5                   10

<210> SEQ ID NO 24
<211> LENGTH: 11
<212> TYPE: PRT
<213> ORGANISM: artificial sequence
<220> FEATURE:
<223> OTHER INFORMATION: synthetic

<400> SEQUENCE: 24

```
Arg Ala Ser Gln Gly Ile Ser Ser Trp Leu Ala
1               5                   10

<210> SEQ ID NO 25
<211> LENGTH: 7
<212> TYPE: PRT
<213> ORGANISM: artificial sequence
<220> FEATURE:
<223> OTHER INFORMATION: synthetic

<400> SEQUENCE: 25

Ala Ala Ser Ser Leu Gln Ser
1               5

<210> SEQ ID NO 26
<211> LENGTH: 7
<212> TYPE: PRT
<213> ORGANISM: artificial sequence
<220> FEATURE:
<223> OTHER INFORMATION: synthetic

<400> SEQUENCE: 26

Gly Ala Ser Ser Leu Gln Ser
1               5

<210> SEQ ID NO 27
<211> LENGTH: 10
<212> TYPE: PRT
<213> ORGANISM: artificial sequence
<220> FEATURE:
<223> OTHER INFORMATION: synthetic

<400> SEQUENCE: 27

Gln Gln Ala Asp Leu His Pro Pro Leu Thr
1               5                   10

<210> SEQ ID NO 28
<211> LENGTH: 9
<212> TYPE: PRT
<213> ORGANISM: artificial sequence
<220> FEATURE:
<223> OTHER INFORMATION: synthetic

<400> SEQUENCE: 28

Gln Gln Thr Val Ser Phe Pro Ile Thr
1               5

<210> SEQ ID NO 29
<211> LENGTH: 9
<212> TYPE: PRT
<213> ORGANISM: artificial sequence
<220> FEATURE:
<223> OTHER INFORMATION: synthetic

<400> SEQUENCE: 29

Gln Gln Lys Asn Pro Phe Pro Pro Thr
1               5

<210> SEQ ID NO 30
<211> LENGTH: 9
<212> TYPE: PRT
<213> ORGANISM: artificial sequence
<220> FEATURE:
<223> OTHER INFORMATION: synthetic

<400> SEQUENCE: 30
```

```
Gln Gln Lys Asn Pro Phe Pro Pro Phe
1               5
```

<210> SEQ ID NO 31
<211> LENGTH: 26
<212> TYPE: PRT
<213> ORGANISM: artificial sequence
<220> FEATURE:
<223> OTHER INFORMATION: synthetic

<400> SEQUENCE: 31

```
Gln Val Gln Leu Gln Glu Ser Gly Pro Gly Leu Val Lys Pro Ser Glu
1               5                   10                  15

Thr Leu Ser Leu Thr Cys Thr Val Ser Gly
            20                  25
```

<210> SEQ ID NO 32
<211> LENGTH: 26
<212> TYPE: PRT
<213> ORGANISM: artificial sequence
<220> FEATURE:
<223> OTHER INFORMATION: synthetic

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25
```

<210> SEQ ID NO 33
<211> LENGTH: 14
<212> TYPE: PRT
<213> ORGANISM: artificial sequence
<220> FEATURE:
<223> OTHER INFORMATION: synthetic

<400> SEQUENCE: 33

```
Trp Ile Arg Gln Pro Pro Gly Lys Gly Leu Glu Trp Ile Gly
1               5                   10
```

<210> SEQ ID NO 34
<211> LENGTH: 14
<212> TYPE: PRT
<213> ORGANISM: artificial sequence
<220> FEATURE:
<223> OTHER INFORMATION: synthetic

<400> SEQUENCE: 34

```
Trp Val Arg Gln Ala Pro Gly Lys Gly Leu Glu Trp Val Ser
1               5                   10
```

<210> SEQ ID NO 35
<211> LENGTH: 30
<212> TYPE: PRT
<213> ORGANISM: artificial sequence
<220> FEATURE:
<223> OTHER INFORMATION: synthetic

<400> SEQUENCE: 35

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30
```

<210> SEQ ID NO 36

```
<211> LENGTH: 30
<212> TYPE: PRT
<213> ORGANISM: artificial sequence
<220> FEATURE:
<223> OTHER INFORMATION: synthetic

<400> SEQUENCE: 36

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys
            20                  25                  30

<210> SEQ ID NO 37
<211> LENGTH: 11
<212> TYPE: PRT
<213> ORGANISM: artificial sequence
<220> FEATURE:
<223> OTHER INFORMATION: synthetic

<400> SEQUENCE: 37

Trp Gly Gln Gly Thr Leu Val Thr Val Ser Ser
1               5                   10

<210> SEQ ID NO 38
<211> LENGTH: 11
<212> TYPE: PRT
<213> ORGANISM: artificial sequence
<220> FEATURE:
<223> OTHER INFORMATION: synthetic

<400> SEQUENCE: 38

Trp Gly Arg Gly Thr Leu Val Thr Val Ser Ser
1               5                   10

<210> SEQ ID NO 39
<211> LENGTH: 23
<212> TYPE: PRT
<213> ORGANISM: artificial sequence
<220> FEATURE:
<223> OTHER INFORMATION: synthetic

<400> SEQUENCE: 39

Asp Ile Gln Met Thr Gln Ser Pro Ser Ser Val Ser Ala Ser Val Gly
1               5                   10                  15
Asp Arg Val Thr Ile Thr Cys
            20

<210> SEQ ID NO 40
<211> LENGTH: 23
<212> TYPE: PRT
<213> ORGANISM: artificial sequence
<220> FEATURE:
<223> OTHER INFORMATION: synthetic

<400> SEQUENCE: 40

Asp Ile Gln Leu Thr Gln Ser Pro Ser Ser Val Ser Ala Ser Val Gly
1               5                   10                  15
Asp Arg Val Thr Ile Thr Cys
            20

<210> SEQ ID NO 41
<211> LENGTH: 15
<212> TYPE: PRT
<213> ORGANISM: artificial sequence
<220> FEATURE:
<223> OTHER INFORMATION: synthetic
```

<400> SEQUENCE: 41

Trp Tyr Gln Gln Lys Pro Gly Lys Ala Pro Lys Leu Leu Ile Tyr
1               5                   10                  15

<210> SEQ ID NO 42
<211> LENGTH: 32
<212> TYPE: PRT
<213> ORGANISM: artificial sequence
<220> FEATURE:
<223> OTHER INFORMATION: synthetic

<400> SEQUENCE: 42

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 43
<211> LENGTH: 10
<212> TYPE: PRT
<213> ORGANISM: artificial sequence
<220> FEATURE:
<223> OTHER INFORMATION: synthetic

<400> SEQUENCE: 43

Phe Gly Gly Gly Thr Lys Val Glu Ile Lys
1               5                   10

<210> SEQ ID NO 44
<211> LENGTH: 115
<212> TYPE: PRT
<213> ORGANISM: artificial sequence
<220> FEATURE:
<223> OTHER INFORMATION: synthetic

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser
        115

<210> SEQ ID NO 45
<211> LENGTH: 115
<212> TYPE: PRT
<213> ORGANISM: artificial sequence
<220> FEATURE:
<223> OTHER INFORMATION: synthetic

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Thr Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gly Lys Ser Ala Phe Asn Pro Trp Gly Gln Gly Thr Leu Val Thr
            100                 105                 110

Val Ser Ser
        115

<210> SEQ ID NO 46
<211> LENGTH: 115
<212> TYPE: PRT
<213> ORGANISM: artificial sequence
<220> FEATURE:
<223> OTHER INFORMATION: synthetic

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asp Tyr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Gly Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gly Lys Ser Ala Phe Asp Pro Trp Gly Gln Gly Thr Leu Val Thr
            100                 105                 110

Val Ser Ser
        115

<210> SEQ ID NO 47
<211> LENGTH: 115
<212> TYPE: PRT
<213> ORGANISM: artificial sequence
<220> FEATURE:
<223> OTHER INFORMATION: synthetic

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
            100                 105                 110

Val Ser Ser
        115

<210> SEQ ID NO 48
<211> LENGTH: 115
<212> TYPE: PRT
<213> ORGANISM: artificial sequence
<220> FEATURE:
<223> OTHER INFORMATION: synthetic

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu His Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
            100                 105                 110

Val Ser Ser
        115

<210> SEQ ID NO 49
<211> LENGTH: 115
<212> TYPE: PRT
<213> ORGANISM: artificial sequence
<220> FEATURE:
<223> OTHER INFORMATION: synthetic

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asp His Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Glu Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
            100                 105                 110

Val Ser Ser

<210> SEQ ID NO 50
<211> LENGTH: 118
<212> TYPE: PRT
<213> ORGANISM: artificial sequence
<220> FEATURE:
<223> OTHER INFORMATION: synthetic

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Pro Ile Tyr Tyr Gly Phe Asp Leu Trp Gly Arg Gly Thr
            100                 105                 110

Leu Val Thr Val Ser Ser
        115

<210> SEQ ID NO 51
<211> LENGTH: 117
<212> TYPE: PRT
<213> ORGANISM: artificial sequence
<220> FEATURE:
<223> OTHER INFORMATION: synthetic

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ser Trp Val Arg Gln Ala Pro Gly Lys Gly Leu Glu Trp Val
        35                  40                  45

Ser Met Ile Ser Gly Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Pro Ile Tyr Tyr Gly Phe Asp Leu Trp Gly Arg Gly Thr Leu
            100                 105                 110

Val Thr Val Ser Ser
        115

<210> SEQ ID NO 52
<211> LENGTH: 118
<212> TYPE: PRT
<213> ORGANISM: artificial sequence
<220> FEATURE:
<223> OTHER INFORMATION: synthetic

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr His Leu Tyr Tyr Gly Phe Asp Leu Trp Gly Arg Gly Thr
            100                 105                 110

Leu Val Thr Val Ser Ser
            115

<210> SEQ ID NO 53
<211> LENGTH: 118
<212> TYPE: PRT
<213> ORGANISM: artificial sequence
<220> FEATURE:
<223> OTHER INFORMATION: synthetic

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ala Ile Tyr Tyr Gly Phe Asp Leu Trp Gly Arg Gly Thr
            100                 105                 110

Leu Val Thr Val Ser Ser
            115

<210> SEQ ID NO 54
<211> LENGTH: 108
<212> TYPE: PRT
<213> ORGANISM: artificial sequence
<220> FEATURE:
<223> OTHER INFORMATION: synthetic

<400> SEQUENCE: 54

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asp Leu His Pro Pro
                 85                  90                  95

Leu Thr Phe Gly Gly Gly Thr Lys Val Glu Ile Lys
            100                 105
```

```
<210> SEQ ID NO 55
<211> LENGTH: 107
<212> TYPE: PRT
<213> ORGANISM: artificial sequence
<220> FEATURE:
<223> OTHER INFORMATION: synthetic

<400> SEQUENCE: 55

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Arg Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Ser Phe Pro Ile
                 85                  90                  95

Thr Phe Gly Gly Gly Thr Lys Val Glu Ile Lys
            100                 105
```

```
<210> SEQ ID NO 56
<211> LENGTH: 293
<212> TYPE: PRT
<213> ORGANISM: artificial sequence
<220> FEATURE:
<223> OTHER INFORMATION: synthetic

<400> SEQUENCE: 56

Met Trp Pro Leu Val Ala Ala Leu Leu Leu Gly Ser Ala Cys Cys Gly
  1               5                  10                  15

Ser Ala Gln Leu Leu Phe Asn Lys Thr Lys Ser Val Glu Phe Thr Phe
                 20                  25                  30

Cys Asn Asp Thr Val Val Ile Pro Cys Phe Val Thr Asn Met Glu Ala
             35                  40                  45

Gln Asn Thr Thr Glu Val Tyr Val Lys Trp Lys Phe Lys Gly Arg Asp
 50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140
```

```
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
            165                 170                 175

Ile Ala Leu Leu Val Ala Gly Leu Val Ile Thr Val Ile Val Ile Val
        180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Glu
        290

<210> SEQ ID NO 57
<211> LENGTH: 107
<212> TYPE: PRT
<213> ORGANISM: artificial sequence
<220> FEATURE:
<223> OTHER INFORMATION: synthetic

<400> SEQUENCE: 57

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Asn Pro Phe Pro Pro
                85                  90                  95

Thr Phe Gly Gly Gly Thr Lys Val Glu Ile Lys
            100                 105

<210> SEQ ID NO 58
<211> LENGTH: 107
<212> TYPE: PRT
<213> ORGANISM: artificial sequence
<220> FEATURE:
<223> OTHER INFORMATION: synthetic

<400> SEQUENCE: 58

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Gly Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Asn Pro Phe Pro Pro
                85                  90                  95

Phe Phe Gly Gly Gly Thr Lys Val Glu Ile Lys
            100                 105
```

<210> SEQ ID NO 59
<211> LENGTH: 345
<212> TYPE: DNA
<213> ORGANISM: artificial sequence
<220> FEATURE:
<223> OTHER INFORMATION: synthetic

<400> SEQUENCE: 59

```
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctattaca gtgggagcac caactacaac    180
ccctccctca agagtcgagt caccatatca gtagacacgt ccaagaacca gttctccctg    240
aagctgagtt ctgtgaccgc cgcagacacg gcggtgtact actgcgccag ggtaagagt     300 gcattcgacc catggggaca gggtacattg gtcaccgtct cctca                    345
```

<210> SEQ ID NO 60
<211> LENGTH: 345
<212> TYPE: DNA
<213> ORGANISM: artificial sequence
<220> FEATURE:
<223> OTHER INFORMATION: synthetic

<400> SEQUENCE: 60

```
caggtgcagc tgcaggagtc gggcccagga ctggtgaagc cttcggagac cctgtccctc     60
acctgcactg tctctggtgg ctccatcagt aattactact ggagctggat ccggcagccc    120
ccagggaagg gactggagtg gattgggacg atctattaca gtgggagcac ccgttacaac    180
ccctccctca agagtcgagt caccatatca gtagacacgt ccaagaacca gttctccctg    240
aagctgagtt ctgtgaccgc cgcagacacg gcggtgtact actgcgccag ggtaagagt     300 gcattcaacc catggggaca gggtacattg gtcaccgtct cctca                    345
```

<210> SEQ ID NO 61
<211> LENGTH: 345
<212> TYPE: DNA
<213> ORGANISM: artificial sequence
<220> FEATURE:
<223> OTHER INFORMATION: synthetic

<400> SEQUENCE: 61

```
caggtgcagc tgcaggagtc gggcccagga ctggtgaagc cttcggagac cctgtccctc     60
acctgcactg tctctggtgg ctccatcgat tattactact ggagctggat ccggcagccc    120
ccagggaagg gactggagtg gattgggtat atctattact cggggagcac cggttacaac    180
ccctccctca agagtcgagt caccatatca gtagacacgt ccaagaacca gttctccctg    240
aagctgagtt ctgtgaccgc cgcagacacg gcggtgtact actgcgccag ggtaagagt     300 gcattcgacc catggggaca gggtacattg gtcaccgtct cctca                    345
```

<210> SEQ ID NO 62
<211> LENGTH: 345
<212> TYPE: DNA
<213> ORGANISM: artificial sequence
<220> FEATURE:
<223> OTHER INFORMATION: synthetic

<400> SEQUENCE: 62

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagtt ctgtgaccgc cgcagacacg gcggtgtact actgcgccag ggtaagacg      300
ggatctgccg catggggaca gggtacattg gtcaccgtct cctca                     345
```

<210> SEQ ID NO 63
<211> LENGTH: 345
<212> TYPE: DNA
<213> ORGANISM: artificial sequence
<220> FEATURE:
<223> OTHER INFORMATION: synthetic

<400> SEQUENCE: 63

```
caggtgcagc tgcaggagtc gggcccagga ctggtgaagc cttcggagac cctgtccctc      60
acctgcactg tctctggtgg ctccatcgag cattactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagtt ctgtgaccgc cgcagacacg gcggtgtact actgcgccag ggtaagacg      300
ggatctgccg catggggaca gggtacattg gtcaccgtct cctca                     345
```

<210> SEQ ID NO 64
<211> LENGTH: 345
<212> TYPE: DNA
<213> ORGANISM: artificial sequence
<220> FEATURE:
<223> OTHER INFORMATION: synthetic

<400> SEQUENCE: 64

```
caggtgcagc tgcaggagtc gggcccagga ctggtgaagc cttcggagac cctgtccctc      60
acctgcactg tctctggtgg ctccatcgat cattactact ggagttggat ccggcagccc     120
ccagggaagg gactggagtg gattgggtat atctattact ctgggagcac cgagtacaac     180
ccctccctca agagtcgagt caccatatca gtagacacgt ccaagaacca gttctccctg     240
aagctgagtt ctgtgaccgc cgcagacacg gcggtgtact actgcgccag ggtaagacg      300
ggatctgccg catggggaca gggtacattg gtcaccgtct cctca                     345
```

<210> SEQ ID NO 65
<211> LENGTH: 354
<212> TYPE: DNA
<213> ORGANISM: artificial sequence
<220> FEATURE:
<223> OTHER INFORMATION: synthetic

<400> SEQUENCE: 65

```
gaggtgcagc tgttggagtc tggggagggc ttggtacagc ctgggggtc cctgagactc       60
tcctgtgcag cctctggatt cacctttagc agctatgcca tgagctgggt ccgccaggct     120
```

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggcggtgt actactgcgc caagacgcct    300
atatactacg gcttcgacct atgggggaga ggtaccttgg tcaccgtctc ctca          354
```

<210> SEQ ID NO 66
<211> LENGTH: 351
<212> TYPE: DNA
<213> ORGANISM: artificial sequence
<220> FEATURE:
<223> OTHER INFORMATION: synthetic

<400> SEQUENCE: 66

```
gaggtgcagc tgttggagtc tgggggaggc ttggtacagc ctggggggtc cctgagactc     60
tcctgtgcag cctctggatt cacctttggg aattatgcca tgagctgggt ccgccaggct    120
ccagggaagg ggctggagtg ggtctcaatg attagtgggg gtggtagcac atactacgca    180
gactccgtga agggccggtt caccatctcc agagacaatt ccaagaacac gctgtatctg    240
caaatgaaca gcctgagagc cgaggacacg gcggtgtact actgcgccaa gacgcctata    300
tactacggct tcgacctatg ggggagaggt accttggtca ccgtctcctc a             351
```

<210> SEQ ID NO 67
<211> LENGTH: 354
<212> TYPE: DNA
<213> ORGANISM: artificial sequence
<220> FEATURE:
<223> OTHER INFORMATION: synthetic

<400> SEQUENCE: 67

```
gaggtgcagc tgttggagtc tgggggaggc ttggtacagc ctggggggtc cctgagactc     60
tcctgtgcag cctctggatt cacctttgat agctatgcca tgacttgggt ccgccaggct    120
ccagggaagg ggctggagtg ggtctcagtt attagtggaa gtggtggtaa gacatactac    180
gcagactccg tgaagggccg gttcaccatc tccagagaca actccaagaa cacgctgtat    240
ctgcaaatga acagcctgag agccgaggac acggcggtgt actactgcgc caagacgcat    300
ctttactacg gcttcgacct atgggggaga ggtaccttgg tcaccgtctc ctca          354
```

<210> SEQ ID NO 68
<211> LENGTH: 354
<212> TYPE: DNA
<213> ORGANISM: artificial sequence
<220> FEATURE:
<223> OTHER INFORMATION: synthetic

<400> SEQUENCE: 68

```
gaggtgcagc tgttggagtc tgggggaggc ttggtacagc ctggggggtc cctgagactc     60
tcctgtgcag cctctggatt cacctttggg aattatgcca tgagctgggt ccgccaggct    120
ccagggaagg ggctggagtg ggtctcagct attagtggaa gtggtggtaa gacatactac    180
gcagactccg tgaagggccg gttcaccatc tccagagaca attccaagaa cacgctgtat    240
ctgcaaatga acagcctgag agccgaggac acggcggtgt actactgcgc caagacggct    300
atatactacg gcttcgacct atgggggaga ggtaccttgg tcaccgtctc ctca          354
```

<210> SEQ ID NO 69
<211> LENGTH: 324
<212> TYPE: DNA

```
<213> ORGANISM: artificial sequence
<220> FEATURE:
<223> OTHER INFORMATION: synthetic

<400> SEQUENCE: 69
gacatccaga tgacccagtc tccatcttcc gtgtctgcat ctgtaggaga cagagtcacc    60
atcacttgtc gggcgagtca gggtattagc aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcagcag gcagacctcc accctcctct cacttttggc   300
ggagggacca aggttgagat caaa                                          324

<210> SEQ ID NO 70
<211> LENGTH: 321
<212> TYPE: DNA
<213> ORGANISM: artificial sequence
<220> FEATURE:
<223> OTHER INFORMATION: synthetic

<400> SEQUENCE: 70
gacatccaga tgacccagtc tccatcttcc gtgtctgcat ctgtaggaga cagagtcacc    60
atcacttgtc gggcgagtca gggtattagc aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcagcag acagtctcct ccctatcac ttttggcgga    300 gggaccaagg ttgagatcaa a                                             321

<210> SEQ ID NO 71
<211> LENGTH: 321
<212> TYPE: DNA
<213> ORGANISM: artificial sequence
<220> FEATURE:
<223> OTHER INFORMATION: synthetic

<400> SEQUENCE: 71
gacatccaga tgacccagtc tccatcttcc gtgtctgcat ctgtaggaga cagagtcacc    60
atcacttgtc gggcgagtca gggtattagc aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcagcag acagtctcct ccctatcac tttcggcgga    300 gggaccaagg tggagatcaa a                                             321

<210> SEQ ID NO 72
<211> LENGTH: 321
<212> TYPE: DNA
<213> ORGANISM: artificial sequence
<220> FEATURE:
<223> OTHER INFORMATION: synthetic

<400> SEQUENCE: 72
gacatccagt tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatggt gcatccagtt tgcaaagtgg ggtcccatca   180
aggttcagcg gcagtggatc tgggacagat ttcactctca ccatcagcag cctgcagcct   240
```
gaagattttg caacttatta ctgtcagcag aaaaatccct tccctcctac ttttggcgga    300
gggaccaagg ttgagatcaa a    321

<210> SEQ ID NO 73
<211> LENGTH: 321
<212> TYPE: DNA
<213> ORGANISM: artificial sequence
<220> FEATURE:
<223> OTHER INFORMATION: synthetic

<400> SEQUENCE: 73
gacatccagt tgacccagtc tccatcttcc gtgtctgcat ctgtaggaga cagagtcacc    60
atcacttgtc gggcgagtca gggtattagc agctggttag cctggtatca gcagaaacca    120
gggaaagccc ctaagctcct gatctatggt gcatccagtt tgcaaagtgg ggtcccatca    180
aggttcagcg gcagtggatc tgggacagat ttcactctca ccatcagcag cctgcagcct    240
gaagattttg caacttatta ctgtcagcag aaaaatccct tccctccttt ttttggcgga    300
gggaccaagg ttgagatcaa a    321

<210> SEQ ID NO 74
<211> LENGTH: 441
<212> TYPE: PRT
<213> ORGANISM: artificial sequence
<220> FEATURE:
<223> OTHER INFORMATION: synthetic

<400> SEQUENCE: 74

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Glu Asp Pro Glu Val Gln Phe Asn Trp
        260                 265                 270

Tyr Val Asp Gly Val Glu Val His Asn Ala Lys Thr Lys Pro Arg Glu
    275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
        340                 345                 350

Met Thr Lys Asn Gln Val Ser Leu Thr Cys Leu Val Lys Gly Phe Tyr
    355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
        420                 425                 430

Gln Lys Ser Leu Ser Leu Ser Leu Gly
        435                 440

<210> SEQ ID NO 75
<211> LENGTH: 215
<212> TYPE: PRT
<213> ORGANISM: artificial sequence
<220> FEATURE:
<223> OTHER INFORMATION: synthetic

<400> SEQUENCE: 75

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Leu His Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 76
<211> LENGTH: 441
<212> TYPE: PRT
<213> ORGANISM: artificial sequence
<220> FEATURE:
<223> OTHER INFORMATION: synthetic

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Thr Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asn Pro Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Glu Asp Pro Glu Val Gln Phe Asn Trp
        260                 265                 270

Tyr Val Asp Gly Val Glu Val His Asn Ala Lys Thr Lys Pro Arg Glu
    275                 280                 285

-continued

```
Glu Gln Phe Asn Ser Thr Tyr Arg Val Val Ser Val Leu Thr Val Leu
290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                325                 330                 335
Gln Pro Arg Glu Pro Gln Val Tyr Thr Leu Pro Pro Ser Gln Glu Glu
                340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                405                 410                 415
Val Phe Ser Cys Ser Val Met His Glu Ala Leu His Asn His Tyr Thr
                420                 425                 430
Gln Lys Ser Leu Ser Leu Ser Leu Gly
            435                 440

<210> SEQ ID NO 77
<211> LENGTH: 441
<212> TYPE: PRT
<213> ORGANISM: artificial sequence
<220> FEATURE:
<223> OTHER INFORMATION: synthetic

<400> SEQUENCE: 77

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Asp Tyr Tyr
                20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Gly Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Lys Ser Ala Phe Asp Pro Trp Gly Gln Gly Thr Leu Val Thr
                100                 105                 110
Val Ser Ser Ala Ser Thr Lys Gly Pro Ser Val Phe Pro Leu Ala Pro
            115                 120                 125
Cys Ser Arg Ser Thr Ser Glu Ser Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Lys Thr Tyr Thr Cys Asn Val Asp His Lys Pro Ser Asn Thr Lys
            195                 200                 205
```

```
Val Asp Lys Arg Val Glu Ser Lys Tyr Gly Pro Pro Cys Pro Pro Cys
210                 215                 220
Pro Ala Pro Glu Ala Ala Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser Gln Glu Asp Pro Glu Val Gln Phe Asn Trp
                260                 265                 270
Tyr Val Asp Gly Val Glu Val His Asn Ala Lys Thr Lys Pro Arg Glu
                275                 280                 285
Glu Gln Phe Asn Ser Thr Tyr Arg Val Val Ser Val Leu Thr Val Leu
        290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                325                 330                 335
Gln Pro Arg Glu Pro Gln Val Tyr Thr Leu Pro Pro Ser Gln Glu Glu
                340                 345                 350
Met Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                405                 410                 415
Val Phe Ser Cys Ser Val Met His Glu Ala Leu His Asn His Tyr Thr
                420                 425                 430
Gln Lys Ser Leu Ser Leu Ser Leu Gly
                435                 440

<210> SEQ ID NO 78
<211> LENGTH: 441
<212> TYPE: PRT
<213> ORGANISM: artificial sequence
<220> FEATURE:
<223> OTHER INFORMATION: synthetic

<400> SEQUENCE: 78

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
                20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Asn Tyr Asn Pro Ser Leu Lys
        50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Lys Thr Gly Ser Ala Ala Trp Gly Gln Gly Thr Leu Val Thr
                100                 105                 110
Val Ser Ser Ala Ser Thr Lys Gly Pro Ser Val Phe Pro Leu Ala Pro
            115                 120                 125
```

```
Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
                260                 265                 270

Tyr Val Asp Gly Val Glu Val His Asn Ala Lys Thr Lys Pro Arg Glu
                275                 280                 285

Glu Gln Phe Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
                340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
                420                 425                 430

Gln Lys Ser Leu Ser Leu Ser Leu Gly
            435                 440

<210> SEQ ID NO 79
<211> LENGTH: 214
<212> TYPE: PRT
<213> ORGANISM: artificial sequence
<220> FEATURE:
<223> OTHER INFORMATION: synthetic

<400> SEQUENCE: 79

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
                20                  25                  30

Leu Ala Trp Tyr Gln Gln Lys Pro Gly Lys Ala Pro Lys Leu Leu Ile
            35                  40                  45
```

```
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Ser Phe Pro Ile
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 80
<211> LENGTH: 441
<212> TYPE: PRT
<213> ORGANISM: artificial sequence
<220> FEATURE:
<223> OTHER INFORMATION: synthetic

<400> SEQUENCE: 80

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Glu His Tyr
                20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Lys Thr Gly Ser Ala Ala Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190
```

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440

<210> SEQ ID NO 81
<211> LENGTH: 441
<212> TYPE: PRT
<213> ORGANISM: artificial sequence
<220> FEATURE:
<223> OTHER INFORMATION: synthetic

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asp His Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Glu Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
            100                 105                 110

```
Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440

<210> SEQ ID NO 82
<211> LENGTH: 444
<212> TYPE: PRT
<213> ORGANISM: artificial sequence
<220> FEATURE:
<223> OTHER INFORMATION: synthetic

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Thr Pro Ile Tyr Tyr Gly Phe Asp Leu Trp Gly Arg Gly Thr
                100                 105                 110
Leu Val Thr Val Ser Ser Ala Ser Thr Lys Gly Pro Ser Val Phe Pro
            115                 120                 125
Leu Ala Pro Cys Ser Arg Ser Thr Ser Glu Ser Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440
```

-continued

<210> SEQ ID NO 83
<211> LENGTH: 214
<212> TYPE: PRT
<213> ORGANISM: artificial sequence
<220> FEATURE:
<223> OTHER INFORMATION: synthetic

<400> SEQUENCE: 83

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Asn Pro Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 443
<212> TYPE: PRT
<213> ORGANISM: artificial sequence
<220> FEATURE:
<223> OTHER INFORMATION: synthetic

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ser Trp Val Arg Gln Ala Pro Gly Lys Gly Leu Glu Trp Val
        35                  40                  45

Ser Met Ile Ser Gly Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

```
Lys Thr Pro Ile Tyr Tyr Gly Phe Asp Leu Trp Gly Arg Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
        210                 215                 220

Pro Cys Pro Ala Pro Glu Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
            435                 440

<210> SEQ ID NO 85
<211> LENGTH: 444
<212> TYPE: PRT
<213> ORGANISM: artificial sequence
<220> FEATURE:
<223> OTHER INFORMATION: synthetic

<400> SEQUENCE: 85

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Asp Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Lys Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr His Leu Tyr Tyr Gly Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
```

<210> SEQ ID NO 86
<211> LENGTH: 214
<212> TYPE: PRT
<213> ORGANISM: artificial sequence
<220> FEATURE:
<223> OTHER INFORMATION: synthetic

<400> SEQUENCE: 86

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Asn Pro Phe Pro Pro
                85                  90                  95

Phe Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87
<211> LENGTH: 444
<212> TYPE: PRT
<213> ORGANISM: artificial sequence
<220> FEATURE:
<223> OTHER INFORMATION: synthetic

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95
Ala Lys Thr Ala Ile Tyr Tyr Gly Phe Asp Leu Trp Gly Arg Gly Thr
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440

<210> SEQ ID NO 88
<211> LENGTH: 444
<212> TYPE: PRT
<213> ORGANISM: artificial sequence
<220> FEATURE:
<223> OTHER INFORMATION: synthetic

<400> SEQUENCE: 88
```

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Lys Ser Ala Phe Asp Pro Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
```

```
                420             425             430
His Tyr Thr Gln Lys Ser Leu Ser Leu Ser Pro Gly
        435                 440
```

<210> SEQ ID NO 89
<211> LENGTH: 444
<212> TYPE: PRT
<213> ORGANISM: artificial sequence
<220> FEATURE:
<223> OTHER INFORMATION: synthetic

<400> SEQUENCE: 89

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Thr Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asn Pro Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

```
            340                 345                 350
Arg Asp Glu Leu Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
            435                 440

<210> SEQ ID NO 90
<211> LENGTH: 444
<212> TYPE: PRT
<213> ORGANISM: artificial sequence
<220> FEATURE:
<223> OTHER INFORMATION: synthetic

<400> SEQUENCE: 90

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Asp Tyr Tyr
                20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Gly Tyr Asn Pro Ser Leu Lys
        50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Lys Ser Ala Phe Asp Pro Trp Gly Gln Gly Thr Leu Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
```

```
            260                 265                 270
Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 91
<211> LENGTH: 444
<212> TYPE: PRT
<213> ORGANISM: artificial sequence
<220> FEATURE:
<223> OTHER INFORMATION: synthetic

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
```

```
                180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
            290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440

<210> SEQ ID NO 92
<211> LENGTH: 444
<212> TYPE: PRT
<213> ORGANISM: artificial sequence
<220> FEATURE:
<223> OTHER INFORMATION: synthetic

<400> SEQUENCE: 92

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Glu His Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Gly Lys Thr Gly Ser Ala Ala Trp Gly Gln Gly Thr Leu Val Thr
```

```
                100             105             110
Val Ser Ser Ala Ser Thr Lys Gly Pro Ser Val Phe Pro Leu Ala Pro
            115                 120             125

Ser Ser Lys Ser Thr Ser Gly Gly Thr Ala Ala Leu Gly Cys Leu Val
            130                 135             140

Lys Asp Tyr Phe Pro Glu Pro Val Thr Val Ser Trp Asn Ser Gly Ala
145             150             155             160

Leu Thr Ser Gly Val His Thr Phe Pro Ala Val Leu Gln Ser Ser Gly
            165                 170             175

Leu Tyr Ser Leu Ser Ser Val Val Thr Val Pro Ser Ser Ser Leu Gly
            180                 185             190

Thr Gln Thr Tyr Ile Cys Asn Val Asn His Lys Pro Ser Asn Thr Lys
            195                 200             205

Val Asp Lys Lys Val Glu Pro Lys Ser Cys Asp Lys Thr His Thr Cys
210             215                 220

Pro Pro Cys Pro Ala Pro Glu Leu Leu Gly Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
            275             280             285

Pro Arg Glu Glu Gln Tyr Asn Ser Thr Tyr Arg Val Val Ser Val Leu
            290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
            325             330             335

Ala Lys Gly Gln Pro Arg Glu Pro Gln Val Tyr Thr Leu Pro Pro Ser
            340             345             350

Arg Asp Glu Leu Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
            370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro Gly
            435             440

<210> SEQ ID NO 93
<211> LENGTH: 444
<212> TYPE: PRT
<213> ORGANISM: artificial sequence
<220> FEATURE:
<223> OTHER INFORMATION: synthetic

<400> SEQUENCE: 93

Gln Val Gln Leu Gln Glu Ser Gly Pro Gly Leu Val Lys Pro Ser Glu
1               5               10              15

Thr Leu Ser Leu Thr Cys Thr Val Ser Gly Gly Ser Ile Asp His Tyr
```

```
                20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Glu Tyr Asn Pro Ser Leu Lys
        50                  55                  60
Ser Arg Val Thr Ile Ser Val Asp Thr Ser Lys Asn Gln Phe Ser Leu
 65                 70                  75                  80
Lys Leu Ser Ser Val Thr Ala Ala Asp Thr Ala Val Tyr Tyr Cys Ala
                85                  90                  95
Arg Gly Lys Thr Gly Ser Ala Ala Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440
```

-continued

```
<210> SEQ ID NO 94
<211> LENGTH: 447
<212> TYPE: PRT
<213> ORGANISM: artificial sequence
<220> FEATURE:
<223> OTHER INFORMATION: synthetic

<400> SEQUENCE: 94
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Pro Ile Tyr Tyr Gly Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 95
<211> LENGTH: 446
<212> TYPE: PRT
<213> ORGANISM: artificial sequence
<220> FEATURE:
<223> OTHER INFORMATION: synthetic

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ser Trp Val Arg Gln Ala Pro Gly Lys Gly Leu Glu Trp Val
        35                  40                  45

Ser Met Ile Ser Gly Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Pro Ile Tyr Tyr Gly Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 96
<211> LENGTH: 447
<212> TYPE: PRT
<213> ORGANISM: artificial sequence
<220> FEATURE:
<223> OTHER INFORMATION: synthetic

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr His Leu Tyr Tyr Gly Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 97
<211> LENGTH: 447
<212> TYPE: PRT
<213> ORGANISM: artificial sequence
<220> FEATURE:
<223> OTHER INFORMATION: synthetic

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ala Ile Tyr Tyr Gly Phe Asp Leu Trp Gly Arg Gly Thr
            100                 105                 110

Leu Val Thr Val Ser Ser Ala Ser Thr Lys Gly Pro Ser Val Phe Pro
        115                 120                 125

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 98
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be Ser, Asp, Glu
<220> FEATURE:
<221> NAME/KEY: misc_feature
<222> LOCATION: (5)..(5)
<223> OTHER INFORMATION: Xaa can be Ser,Asn, Tyr or His

<400> SEQUENCE: 98
```

```
Gly Ser Ile Xaa Xaa Tyr Tyr Trp Ser
1               5
```

<210> SEQ ID NO 99
<211> LENGTH: 9
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be Ser, Gly or Asp
<220> FEATURE:
<221> NAME/KEY: misc_feature
<222> LOCATION: (5)..(5)
<223> OTHER INFORMATION: Xaa can be Ser or Asn
<220> FEATURE:
<221> NAME/KEY: misc_feature
<222> LOCATION: (9)..(9)
<223> OTHER INFORMATION: Xaa can be Ser or Thr

<400> SEQUENCE: 99

```
Phe Thr Phe Xaa Xaa Tyr Ala Met Xaa
1               5
```

<210> SEQ ID NO 100
<211> LENGTH: 16
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be Tyr or Thr
<220> FEATURE:
<221> NAME/KEY: misc_feature
<222> LOCATION: (9)..(9)
<223> OTHER INFORMATION: Xaa can be Asn, Arg, Gly or Glu

<400> SEQUENCE: 100

```
Xaa Ile Tyr Tyr Ser Gly Ser Thr Xaa Tyr Asn Pro Ser Leu Lys Ser
1               5                   10                  15
```

<210> SEQ ID NO 101
<211> LENGTH: 17
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be Ala, Met, or Val
<220> FEATURE:
<221> NAME/KEY: misc_feature
<222> LOCATION: (5)..(5)
<223> OTHER INFORMATION: Xaa can be Ser or deleted
<220> FEATURE:
<221> NAME/KEY: misc_feature
<222> LOCATION: (8)..(8)
<223> OTHER INFORMATION: Xaa can be Ser or Lys

<400> SEQUENCE: 101

```
Xaa Ile Ser Gly Xaa Gly Gly Xaa Thr Tyr Tyr Ala Asp Ser Val Lys
1               5                   10                  15
Gly
```

<210> SEQ ID NO 102
<211> LENGTH: 9

-continued

```
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be Ser or Thr
<220> FEATURE:
<221> NAME/KEY: misc_feature
<222> LOCATION: (6)..(6)
<223> OTHER INFORMATION: Xaa can be Ala,or Gly
<220> FEATURE:
<221> NAME/KEY: misc_feature
<222> LOCATION: (7)..(7)
<223> OTHER INFORMATION: Xaa can be Phe,or Ser
<220> FEATURE:
<221> NAME/KEY: misc_feature
<222> LOCATION: (8)..(8)
<223> OTHER INFORMATION: Xaa can be Asp, Asn or Ala
<220> FEATURE:
<221> NAME/KEY: misc_feature
<222> LOCATION: (9)..(9)
<223> OTHER INFORMATION: Xaa can be Pro or Ala

<400> SEQUENCE: 102

Ala Arg Gly Lys Xaa Xaa Xaa Xaa Xaa
1               5

<210> SEQ ID NO 103
<211> LENGTH: 11
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be Pro, His or Ala
<220> FEATURE:
<221> NAME/KEY: misc_feature
<222> LOCATION: (5)..(5)
<223> OTHER INFORMATION: Xaa can be Ile, or Leu

<400> SEQUENCE: 103

Ala Lys Thr Xaa Xaa Tyr Tyr Gly Phe Asp Leu
1               5                   10

<210> SEQ ID NO 104
<211> LENGTH: 467
<212> TYPE: PRT
<213> ORGANISM: artificial sequence
<220> FEATURE:
<223> OTHER INFORMATION: synthetic

<400> SEQUENCE: 104

Met Gly Trp Ser Leu Ile Leu Leu Phe Leu Val Ala Val Ala Thr Arg
1               5                   10                  15

Val Leu Ser Glu Val Arg Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Gly Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Thr Ser Arg Asp Asp Ser Lys Asn
                85                  90                  95
```

```
Ala Leu Tyr Leu Gln Met Asn Ser Leu Arg Ala Glu Asp Thr Ala Val
            100                 105                 110

Tyr Tyr Cys Ala Arg Gly Gly Pro Gly Trp Tyr Ala Ala Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly
465

<210> SEQ ID NO 105
<211> LENGTH: 236
<212> TYPE: PRT
<213> ORGANISM: artificial sequence
<220> FEATURE:
<223> OTHER INFORMATION: synthetic
```

<400> SEQUENCE: 105

```
Met Asp Phe Gln Val Gln Ile Ile Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asp Leu Pro Ala Phe Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 106
<211> LENGTH: 465
<212> TYPE: PRT
<213> ORGANISM: artificial sequence
<220> FEATURE:
<223> OTHER INFORMATION: synthetic

<400> SEQUENCE: 106

```
Met Gly Trp Ser Leu Ile Leu Leu Phe Leu Val Ala Val Ala Thr Arg
1               5                   10                  15

Val Leu Ser Glu Val Arg Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Gly Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Thr Ser Arg Asp Asp Ser Lys Asn
                85                  90                  95

Ala Leu Tyr Leu Gln Met Asn Ser Leu Arg Ala Glu Asp Thr Ala Val
            100                 105                 110
```

```
Tyr Tyr Cys Ala Arg Gly Gly Pro Gly Trp Tyr Ala Ala Asp Val Trp
            115                 120                 125

Gly Gln Gly Thr Thr Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465

<210> SEQ ID NO 107
<211> LENGTH: 236
<212> TYPE: PRT
<213> ORGANISM: artificial sequence
<220> FEATURE:
<223> OTHER INFORMATION: synthetic

<400> SEQUENCE: 107
```

-continued

```
Met Asp Phe Gln Val Gln Ile Ile Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln Ser Ile Ser Ser Tyr Leu Asn Trp Tyr Gln Gln Lys Pro Gly Lys
        50                  55                  60

Ala Pro Lys Leu Leu Ile Tyr Ala Ala Ser Ser Leu Gln Ser Gly Val
65                      70                  75                  80

Pro Ser Arg Phe Ser Gly Ser Gly Ser Gly Thr Asp Phe Thr Leu Thr
                85                  90                      95

Ile Ser Ser Leu Gln Pro Glu Asp Phe Ala Thr Tyr Tyr Cys Gln Gln
                100                 105                 110

Ala Asp Leu Pro Ala Phe Ala Phe Gly Gly Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235
```

ANTI-CD47 ANTIBODIES AND USES THEREOF

The present invention is directed to a novel antibody which binds specifically to the integrin-associated protein (IAP), (also named CD47) and the antibody fragments thereof and a composition comprising the antibody or antibody fragments. The present invention relates further to a nucleic acid encoding the antibodies or antibody fragments thereof and host cells comprise the same, as well as the relevant use of the same. In addition, the present invention is also directed to the use of these antibodies and antibody fragments in the therapy and diagnosis.

BACKGROUND OF THE INVENTION

Cancer immunotherapy is a highlight in the field of biological science in the recent years and both the T cell-based immune checkpoint inhibitor therapies with CTLA4 antibodies, PD-1 antibodies, PD-L1 antibodies, etc. and the cell therapies such as CAR-T, TCR-T, etc. are the immunotherapies very popular in the recent years. These immunotherapies without exception are focusing on how to restore the functionality of T cells, in the other words, primarily focusing on how to enhance the competency of the acquired immunity system. However, it is still tortuous for the pathway to conquer cancers by targeting the immune checkpoint and activating the functionality of T cells, thereby enhancing the competency of the acquired immunity system. Nonetheless, the role of the intrinsic immune system in the tumor immunotherapy has not been brought to play for a long time. In fact, macrophages represent about 50% in the tumor tissue over the entire tumor infiltration region. It is more important that the number of macrophages is inversely correlated to prognosis of a tumor, which further demonstrates the extremely important role of macrophages in tumors.

Two signals are required for the phagocytic effect of the macrophages: One signal is activation of the "Eat me" signal targeting the cell surface, another is deactivation of the "don't Eat me" signal targeting the same surface. Absence of either of the signals is insufficient to trigger initiation of the phagocytic effect. The increasing evidences demonstrate that CD47 belongs to a class of "don't Eat me" signals and inhibits macrophage phagocytosis by interacting with the Signal regulatory protein α (SIRP α) on the surface of macrophage. Tumor cells can also evade macrophage phagocytosis by expressing CD47 (See e.g., EP2242512 and the relevant literature cited therein).

CD47 is also called integrin-associated protein (IAP) and is an immunoglobulin superfamily member. CD47 is extensively expressed on the surface of cells and can interact with SIRPα, thrombospondin-1 (TSP1) and integrins, mediating an array of responses such as apoptosis, proliferation, immunity, etc. TSP1 is related to cellular proliferation, growth and differentiation. CD47 binding to TSP1 plays a key role in regulating cellular migration, cellular proliferation and apoptosis and facilitates angiogenesis and inflammatory response. Moreover, CD47 is an important marker for self-recognition on the cell surface. CD47 can bind to SIRP alpha protein on the surface of macrophage, phosphorylate the immunoreceptor tyrosine inhibition motif (ITIM) of the protein, and subsequently recruit the SHP-1 protein, resulting in a series of cascade responses to inhibit macrophage phagocytosis (see e.g., U.S. Pat. No. 9,382,320 and the relevant literature cited therein).

Different research studies demonstrate that, almost all of the tumor cells and tissues express CD47 highly. CD47 highly expressed on the surface of tumor cells signals "don't eat me" by binding to SIRP alpha on the surface of macrophages, which allows the macrophages in the tumor tissue infiltrated areas not only to be in harmony with the tumor cells, but also to facilitate proliferation of the vessels within the tumor, inhibit the role of the effector T-cell, thus facilitating proliferation and growth of tumor cells.

The role of CD47 in facilitating cell proliferation is largely dependent on cell types, since activation and loss of CD47 can results in enhanced proliferation. Activation of CD47 with TSP-1 can increase proliferation of human U87 and U373 astrocytoma cells, but not the normal astroglial cells. In addition, CD47 blocks the inhibitory effect of antibodies on proliferation of the unstimulated astrocytoma cells, but does not inhibit the normal astroglial cells. Although the exact mechanism has not been elucidated, CD47 might facilitate proliferation of cancer cells through PI3K/Akt pathway, while it can not facilitate proliferation of normal cells (Sick E., Boukhari A., Deramaudt T., Ronde P., Bucher B., André P., Gies J. P., Takeda K., Activation of CD47 receptors causes proliferation of human astrocytoma but not normal astrocytes via an Akt-dependent pathway, Glia. 2011 February, 59 (2): 308-19: 308-19).

CD47 attachment results in cell death of many normal and tumor cells line through apoptosis or autophagy. Activation of CD47 induces rapid apoptosis of T cells. Incubation of Jurkat cells and peripheral blood mononucleated cells (PBMC) with the monocolonal antibody Ad22 results in apoptosis within 3 hours. Nonetheless, no cell apoptosis was observed after incubation with other anti-CD47 antibodies. The function of CD47 to induce apoptosis appears to be dependent upon activation at specific epitopes on the extracellular domain (Pettersen R. D., Hestdal K., Olafsen M. K., Lie S. O., Lindberg F. P. (June, 1999), CD47 signals T cell death, J. Immunol. 162 (12): 7031-40. PMID 10358145).

At present, a plurality of anti-CD47 antibodies have been reported. For example, a human chimeric monoclonal antibody of IgG1 Class derived from B6H12 and the humanized B6H12 antibody produced by CDR-grafting have been reported in U.S. Patent US2015/0183874 A1, and have lower immunogenicity compared to the antibody known. An anti-CD47 antibody which does not result in apparent hemagglutinating reaction has been reported in U.S. Pat. No. 9,045,541 and is effective significantly in tumor model compared to the antibody known, for example in increasing the ability of macrophages to phagocytize the tumor cells.

The majority of antibodies known in the prior art which block CD47 binding to SIRPα cause agglutination of red blood cell, while facilitating macrophage phagocytosis, which weaken significantly the therapeutic effect of the corresponding antibody.

Hence, in the various therapies against tumors and/or cancers, there is a great need for developing an anti-CD47 antibody which has good specificity for a target site, excellent therapeutic efficacy (e.g., improve macrophage phagocytosis, inhibit tumor growth, and even enable complete disappearance of tumors), and less side effects. The present invention satisfies the need in this aspect.

SUMMARY OF THE INVENTION

The invention provides an anti-CD47 antibody, the composition, kit, method and use relevant to the anti-CD47 antibody.

The inventors of the invention have made the surprising discovery that the antibody developed in the present invention has significant anti-tumor activities, is able to inhibit significantly the growth of tumor, and even enables complete disappearance of tumor.

In some embodiments, the invention provides an anti-CD47 antibody which binds to a CD47 or a fragment thereof (preferably a human CD47 protein), or the antibody fragment thereof (preferably the antigen-binding fragment thereof).

In some embodiments, the anti-CD47 antibody or antigen-binding fragment thereof according to the present invention comprises or consists of the sequence of one to three of the following heavy chain complementary determining regions (HCDRs) selected from the group consisting of: (i) HCDR1 comprising the amino acid sequence selected from the group consisting of SEQ ID NO: 1, 2, 3, 4, 5, 6, 7, 8, 98 and 99, (ii) HCDR2 comprising the amino acid sequence selected from the group consisting of SEQ ID NO: 9, 10, 11, 12, 13, 14, 15, 16, 100 and 101, (iii) HCDR3 comprising the amino acid sequence selected from the group consisting of SEQ ID NO: 17, 18, 19, 20, 21, 22, 102 and 103, and (iv) HCDRs in (i), (ii) and (iii), comprising an amino acid substitution (e.g., a conservative substitution), deletion or insertion of at least one amino acid and no more than 5 amino acids, wherein the anti-CD47 antibody comprising the modified CDRs still has the ability to bind to CD47.

In some embodiments, the anti-CD47 antibody or antigen-binding fragment thereof according to the present invention comprises or consists of the sequence of one to three of the following light chain complementary determining regions (LCDRs) selected from the group consisting of: (i) LCDR1 comprising the amino acid sequence of SEQ ID NO: 23 and 24, (ii) LCDR2 comprising the amino acid sequence of SEQ ID NO: 25 and 26, (iii) LCDR3 comprising the amino acid sequence of SEQ ID NO: 27, 28, 29 and 30, and (iv) LCDRs in (i), (ii) and (iii), comprising an amino acid substitution (e.g., a conservative substitution), deletion or insertion of at least one amino acid and no more than 5 amino acids, wherein the anti-CD47 antibody comprising the modified CDRs still has the ability to bind to CD47.

In some embodiments, the anti-CD47 antibody or antigen-binding fragment thereof according to the present invention comprises A) one to three of the following heavy chain complementary determining regions (HCDRs) selected from the group consisting of: (i) HCDR1 comprising the amino acid sequence selected from the group consisting of SEQ ID NO: 1, 2, 3, 4, 5, 6, 7, 8, 98 and 99; (ii) HCDR2 comprising the amino acid sequence selected from the group consisting of SEQ ID NO: 9, 10, 11, 12, 13, 14, 15, 16, 100 and 101; (iii) HCDR3 comprising the amino acid sequence selected from the group consisting of SEQ ID NO: 17, 18, 19, 20, 21, 22, 102 and 103; (iv) HCDRs in (i), (ii) and (iii), comprising an amino acid substitution (e.g., a conservative substitution), deletion or insertion of at least one amino acid and no more than 5 amino acids; and B) one to three of the following light chain complementary determining regions (LCDRs) selected from the group consisting of: (i) LCDR1 comprising the amino acid sequence of SEQ ID NO: 23 and 24, (ii) LCDR2 comprising the amino acid sequence of SEQ ID NO: 25 and 26, (iii) LCDR3 comprising the amino acid sequence of SEQ ID NO: 27, 28, 29 and 30, and (iv) LCDRs in (i), (ii) and (iii), comprising an amino acid substitution (e.g., a conservative substitution), deletion or insertion of at least one amino acid and no more than 5 amino acids, wherein the anti-CD47 antibody comprising the modified CDRs still has the ability to bind to CD47.

In some embodiments, the anti-CD47 antibody or antigen-binding fragment thereof according to the present invention comprises the heavy chain complementarity determining regions HCDR1, HCDR2 and HCDR3, wherein HCDR1 comprises or consists of the amino acid sequence selected from the group consisting of SEQ ID NO: 1, 2, 3, 4, 5, 6, 7, 8, 98 and 99; HCDR2 comprises or consists of the amino acid sequence selected from the group consisting of SEQ ID NO: 9, 10, 11, 12, 13, 14, 15, 16, 100 and 101; HCDR3 comprises or consists of the amino acid sequence selected from the group consisting of SEQ ID NO: 17, 18, 19, 20, 21, 22, 102 and 103.

In some embodiments, the anti-CD47 antibody or antigen-binding fragment thereof according to the present invention comprises the light chain complementarity determining regions LCDR1, LCDR2 and LCDR3, wherein LCDR1 comprises or consists of the amino acid sequence selected from the group consisting of the amino acid sequence shown in SEQ ID NO: 23 and 24; LCDR2 comprises or consists of the amino acid sequence selected from the group consisting of the amino acid sequence shown in SEQ ID NO: 25 and 26; LCDR3 comprises or consists of the amino acid sequence selected from the group consisting of the amino acid sequence shown in SEQ ID NO: 27, 28, 29 and 30.

In some embodiments, anti-CD47 antibody or antigen-binding fragment thereof according to the present invention comprises the heavy chain complementarity determining regions HCDR1, HCDR2 and HCDR3 and the light chain complementarity determining regions LCDR1, LCDR2 and LCDR3, wherein HCDR1 comprises or consists of the amino acid sequence selected from the group consisting of SEQ ID NO: 1, 2, 3, 4, 5, 6, 7, 8, 98 and 99; HCDR2 comprises or consists of the amino acid sequence selected from the group consisting of SEQ ID NO: 9, 10, 11, 12, 13, 14, 15, 16, 100 and 101; HCDR3 comprises or consists of the amino acid sequence selected from the group consisting of SEQ ID NO: 17, 18, 19, 20, 21, 22, 102 and 103; LCDR1 comprises or consists of the amino acid sequence selected from the group consisting of the amino acid sequence shown in SEQ ID NO: 23 and 24; LCDR2 comprises or consists of the amino acid sequence selected from the group consisting of the amino acid sequence shown in SEQ ID NO: 25 and 26; LCDR3 comprises or consists of the amino acid sequence selected from the group consisting of the amino acid sequence shown in SEQ ID NO: 27, 28, 29 and 30.

In the preferred embodiment, the present invention provides an anti-CD47 antibody or antigen-binding fragment thereof comprising the heavy chain complementarity determining regions HCDR1, HCDR2 and HCDR3 and the light chain complementarity determining regions LCDR1, LCDR2 and LCDR3, wherein HCDR1 comprises or consists of the amino acid sequence shown in SEQ ID NO: 98 or 99; HCDR2 comprises or consists of the amino acid sequence shown in SEQ ID NO: 100 or 101; HCDR3 comprises or consists of the amino acid sequence shown in SEQ ID NO: 102 or 103; LCDR1 comprises or consists of the amino acid sequence selected from the group consisting of the amino acid sequence shown in SEQ ID NO: 23 and 24; LCDR2 comprises or consists of the amino acid sequence selected from the group consisting of the amino acid sequence shown in SEQ ID NO: 25 and 26; LCDR3 comprises or consists of the amino acid sequence selected from the group consisting of the amino acid sequence shown in SEQ ID NO: 27, 28, 29 and 30.

In the preferred embodiment, the present invention provides an anti-CD47 antibody or antigen-binding fragment thereof, wherein HCDR1 comprises or consists of the amino acid sequence shown in SEQ ID NO: 1; HCDR2 comprises or consists of the amino acid sequence shown in SEQ ID NO: 9; HCDR3 comprises or consists of the amino acid sequence shown in SEQ ID NO: 17; LCDR1 comprises or consists of the amino acid sequence shown in SEQ ID NO: 23; LCDR2 comprises or consists of the amino acid sequence shown in SEQ ID NO: 25; and LCDR3 comprises or consists of the amino acid sequence shown in SEQ ID NO: 27.

In the preferred embodiment, the present invention provides an anti-CD47 antibody or antigen-binding fragment thereof, wherein HCDR1 comprises or consists of the amino acid sequence shown in SEQ ID NO: 2; HCDR2 comprises or consists of the amino acid sequence shown in SEQ ID NO: 10; HCDR3 comprises or consists of the amino acid sequence shown in SEQ ID NO: 18; LCDR1 comprises or consists of the amino acid sequence shown in SEQ ID NO: 23; LCDR2 comprises or consists of the amino acid sequence shown in SEQ ID NO: 25; and LCDR3 comprises or consists of the amino acid sequence shown in SEQ ID NO: 27.

In the preferred embodiment, the present invention provides an anti-CD47 antibody or antigen-binding fragment thereof, wherein HCDR1 comprises or consists of the amino acid sequence shown in SEQ ID NO: 3; HCDR2 comprises or consists of the amino acid sequence shown in SEQ ID NO: 11; HCDR3 comprises or consists of the amino acid sequence shown in SEQ ID NO: 17; LCDR1 comprises or consists of the amino acid sequence shown in SEQ ID NO: 23; LCDR2 comprises or consists of the amino acid sequence shown in SEQ ID NO: 25; and LCDR3 comprises or consists of the amino acid sequence shown in SEQ ID NO: 27.

In the preferred embodiment, the present invention provides an anti-CD47 antibody or antigen-binding fragment thereof, wherein HCDR1 comprises or consists of the amino acid sequence shown in SEQ ID NO: 1; HCDR2 comprises or consists of the amino acid sequence shown in SEQ ID NO: 9; HCDR3 comprises or consists of the amino acid sequence shown in SEQ ID NO: 19; LCDR1 comprises or consists of the amino acid sequence shown in SEQ ID NO: 23; LCDR2 comprises or consists of the amino acid sequence shown in SEQ ID NO: 25; and LCDR3 comprises or consists of the amino acid sequence shown in SEQ ID NO: 28.

In the preferred embodiment, the present invention provides an anti-CD47 antibody or antigen-binding fragment thereof, wherein HCDR1 comprises or consists of the amino acid sequence shown in SEQ ID NO: 4; HCDR2 comprises or consists of the amino acid sequence shown in SEQ ID NO: 9; HCDR3 comprises or consists of the amino acid sequence shown in SEQ ID NO: 19; LCDR1 comprises or consists of the amino acid sequence shown in SEQ ID NO: 23; LCDR2 comprises or consists of the amino acid sequence shown in SEQ ID NO: 25; and LCDR3 comprises or consists of the amino acid sequence shown in SEQ ID NO: 28.

In the preferred embodiment, the present invention provides an anti-CD47 antibody or antigen-binding fragment thereof, wherein HCDR1 comprises or consists of the amino acid sequence shown in SEQ ID NO: 5; HCDR2 comprises or consists of the amino acid sequence shown in SEQ ID NO: 12; HCDR3 comprises or consists of the amino acid sequence shown in SEQ ID NO: 19; LCDR1 comprises or consists of the amino acid sequence shown in SEQ ID NO: 23; LCDR2 comprises or consists of the amino acid sequence shown in SEQ ID NO: 25; and LCDR3 comprises or consists of the amino acid sequence shown in SEQ ID NO: 28.

In the preferred embodiment, the present invention provides an anti-CD47 antibody or antigen-binding fragment thereof, wherein HCDR1 comprises or consists of the amino acid sequence shown in SEQ ID NO: 6; HCDR2 comprises or consists of the amino acid sequence shown in SEQ ID NO: 13; HCDR3 comprises or consists of the amino acid sequence shown in SEQ ID NO: 20; LCDR1 comprises or consists of the amino acid sequence shown in SEQ ID NO: 24; LCDR2 comprises or consists of the amino acid sequence shown in SEQ ID NO: 26; and LCDR3 comprises or consists of the amino acid sequence shown in SEQ ID NO: 29.

In the preferred embodiment, the present invention provides an anti-CD47 antibody or antigen-binding fragment thereof, wherein HCDR1 comprises or consists of the amino acid sequence shown in SEQ ID NO: 7; HCDR2 comprises or consists of the amino acid sequence shown in SEQ ID NO: 14; HCDR3 comprises or consists of the amino acid sequence shown in SEQ ID NO: 20; LCDR1 comprises or consists of the amino acid sequence shown in SEQ ID NO: 24; LCDR2 comprises or consists of the amino acid sequence shown in SEQ ID NO: 26; and LCDR3 comprises or consists of the amino acid sequence shown in SEQ ID NO: 29.

In the preferred embodiment, the present invention provides an anti-CD47 antibody or antigen-binding fragment thereof, wherein HCDR1 comprises or consists of the amino acid sequence shown in SEQ ID NO: 8; HCDR2 comprises or consists of the amino acid sequence shown in SEQ ID NO: 15; HCDR3 comprises or consists of the amino acid sequence shown in SEQ ID NO: 21; LCDR1 comprises or consists of the amino acid sequence shown in SEQ ID NO: 24; LCDR2 comprises or consists of the amino acid sequence shown in SEQ ID NO: 26; and LCDR3 comprises or consists of the amino acid sequence shown in SEQ ID NO: 30.

In the preferred embodiment, the present invention provides an anti-CD47 antibody or antigen-binding fragment thereof, wherein HCDR1 comprises or consists of the amino acid sequence shown in SEQ ID NO: 7; HCDR2 comprises or consists of the amino acid sequence shown in SEQ ID NO: 16; HCDR3 comprises or consists of the amino acid sequence shown in SEQ ID NO: 22; LCDR1 comprises or consists of the amino acid sequence shown in SEQ ID NO: 24; LCDR2 comprises or consists of the amino acid sequence shown in SEQ ID NO: 26; and LCDR3 comprises or consists of the amino acid sequence shown in SEQ ID NO: 30.

In some embodiments, the anti-CD47 antibody or antigen-binding fragment thereof according to the present invention comprises a heavy chain variable region HCVR comprising or consisting of an amino acid sequence having at least 90%, 91%, 92%, 93%, 94%, 95%, 96%, 97%, 98%, 99% or 100% identity to the amino acid sequence selected from the group consisting of SEQ ID NO: 44, 45, 46, 47, 48, 49, 50, 51, 52 and 53. In some embodiments, the heavy chain variable region HCVR of the anti-CD47 antibody comprises an amino acid sequence having one or more amino acid substitutions (e.g., conservative substitutions), insertions or deletions compared to the amino acid sequence selected from the group consisting of SEQ ID NO: 44, 45, 46, 47, 48, 49, 50, 51, 52 and 53, however, the anti-CD47 antibody comprising said HCVR still has the ability to bind to CD47.

In some embodiments, the anti-CD47 antibody or antigen-binding fragment thereof according to the present invention comprises a light chain variable region LCVR comprising or consisting of an amino acid sequence having at least 90%, 91%, 92%, 93%, 94%, 95%, 96%, 97%, 98%, 99% or 100% identity to the amino acid sequence shown in SEQ ID NO: 54, 55, 57 and 58. In some embodiments, the light chain variable region LCVR of the anti-CD47 antibody comprises an amino acid sequence having one or more amino acid substitutions (e.g., a conservative substitutions), insertions or deletions compared to the amino acid sequence shown in SEQ ID NO: 54, 55, 57 and 58, however, the anti-CD47 antibody comprising said LCVR still has the ability to bind to CD47.

In some embodiments, the anti-CD47 antibody or antigen-binding fragment thereof according to the present invention comprises a heavy chain variable region (HCVR) and a light chain variable region (LCVR), wherein the heavy chain variable region HCVR comprise or consists of an amino acid sequence having at least 90%, 91%, 92%, 93%, 94%, 95%, 96%, 97%, 98%, 99% or 100% identity to the amino acid sequence selected from the group consisting of SEQ ID NO: 44, 45, 46, 47, 48, 49, 50, 51, 52 and 53 and the light chain variable region LCVR comprises or consists of an amino acid sequence having at least 90%, 91%, 92%, 93%, 94%, 95%, 96%, 97%, 98%, 99% or 100% identity to the amino acid sequence shown in SEQ ID NO: 54, 55, 57 and 58.

In the preferred embodiment, the invention provides an anti-CD47 antibody or antigen-binding fragment thereof, wherein the heavy chain variable region HCVR comprises or consists of the amino acid sequence shown in SEQ ID NO: 44; and the light chain variable region LCVR comprises or consists of the amino acid sequence shown in SEQ ID NO: 54.

In the preferred embodiment, the invention provides an anti-CD47 antibody or antigen-binding fragment thereof, wherein the heavy chain variable region HCVR comprises or consists of the amino acid sequence shown in SEQ ID NO: 45; and the light chain variable region LCVR comprises or consists of the amino acid sequence shown in SEQ ID NO: 54.

In the preferred embodiment, the invention provides an anti-CD47 antibody or antigen-binding fragment thereof, wherein the heavy chain variable region HCVR comprises or consists of the amino acid sequence shown in SEQ ID NO: 46; and the light chain variable region LCVR comprises or consists of the amino acid sequence shown in SEQ ID NO: 54.

In the preferred embodiment, the invention provides an anti-CD47 antibody or antigen-binding fragment thereof, wherein the heavy chain variable region HCVR comprises or consists of the amino acid sequence shown in SEQ ID NO: 47; and the light chain variable region LCVR comprises or consists of the amino acid sequence shown in SEQ ID NO: 55.

In the preferred embodiment, the invention provides an anti-CD47 antibody or antigen-binding fragment thereof, wherein the heavy chain variable region HCVR comprises or consists of the amino acid sequence shown in SEQ ID NO: 48; and the light chain variable region LCVR comprises or consists of the amino acid sequence shown in SEQ ID NO: 55.

In the preferred embodiment, the invention provides an anti-CD47 antibody or antigen-binding fragment thereof, wherein the heavy chain variable region HCVR comprises or consists of the amino acid sequence shown in SEQ ID NO: 49; and the light chain variable region LCVR comprises or consists of the amino acid sequence shown in SEQ ID NO: 55.

In the preferred embodiment, the invention provides an anti-CD47 antibody or antigen-binding fragment thereof, wherein the heavy chain variable region HCVR comprises or consists of the amino acid sequence shown in SEQ ID NO: 50; and the light chain variable region LCVR comprises or consists of the amino acid sequence shown in SEQ ID NO: 57.

In the preferred embodiment, the invention provides an anti-CD47 antibody or antigen-binding fragment thereof, wherein the heavy chain variable region HCVR comprises or consists of the amino acid sequence shown in SEQ ID NO: 51; and the light chain variable region LCVR comprises or consists of the amino acid sequence shown in SEQ ID NO: 57.

In the preferred embodiment, the invention provides an anti-CD47 antibody or antigen-binding fragment thereof, wherein the heavy chain variable region HCVR comprises or consists of the amino acid sequence shown in SEQ ID NO: 52; and the light chain variable region LCVR comprises or consists of the amino acid sequence shown in SEQ ID NO: 58.

In the preferred embodiment, the invention provides an anti-CD47 antibody or antigen-binding fragment thereof, wherein the heavy chain variable region HCVR comprises or consists of the amino acid sequence shown in SEQ ID NO: 53; and the light chain variable region LCVR comprises or consists of the amino acid sequence shown in SEQ ID NO: 58.

In some embodiments, the anti-CD47 antibody or antigen-binding fragment thereof according to the present invention comprises a heavy chain, wherein the heavy chain comprises or consists of an amino acid sequence having at least 90%, 91%, 92%, 93%, 94%, 95%, 96%, 97%, 98%, 99% or 100% identity to the amino acid sequence selected from the group consisting of SEQ ID NO: 74, 76, 77, 78, 80, 81, 82, 84, 85, 87, 88, 89, 90, 91, 92, 93, 94, 95, 96 and 97. In some embodiments, the heavy chain of the anti-CD47 antibody comprises an amino acid sequence having one or more amino acid substitutions (e.g., a conservative substitutions), insertions or deletions compared to the amino acid sequence selected from the group consisting of SEQ ID NO: 74, 76, 77, 78, 80, 81, 82, 84, 85, 87, 88, 89, 90, 91, 92, 93, 94, 95, 96 and 97, however, the anti-CD47 antibody comprising said heavy chain still has the ability to bind to CD47.

In some embodiments, the anti-CD47 antibody or antigen-binding fragment thereof according to the present invention comprises a light chain, wherein the light chain comprises or consists of an amino acid sequence having at least 90%, 91%, 92%, 93%, 94%, 95%, 96%, 97%, 98%, 99% or 100% identity to the amino acid sequence shown in SEQ ID NO: 75, 79, 83 and 86. In some embodiments, the light chain of the anti-CD47 antibody comprises an amino acid sequence having one or more amino acid substitutions (e.g., a conservative substitutions), insertions or deletions compared to the amino acid sequence selected from the group consisting of SEQ ID NO: 75, 79, 83 and 86, however, the anti-CD47 antibody comprising said light chain still has the ability to bind to CD47.

In some embodiments, the anti-CD47 antibody or antigen-binding fragment thereof according to the present invention comprises a heavy chain and a light chain, wherein the heavy chain comprise or consists of an amino acid sequence having at least 90%, 91%, 92%, 93%, 94%, 95%, 96%, 97%, 98%, 99% or 100% identity to the amino acid sequence selected from the group consisting of SEQ ID NO: 74, 76, 77, 78, 80, 81, 82, 84, 85, 87, 88, 89, 90, 91, 92, 93, 94, 95, 96 and 97 and the light chain comprises or consists of an amino acid sequence having at least 90%, 91%, 92%, 93%, 94%, 95%, 96%, 97%, 98%, 99% or 100% identity to the amino acid sequence shown in SEQ ID NO: 75, 79, 83 and 86.

In the preferred embodiment, the invention provides an anti-CD47 antibody or antigen-binding fragment thereof, wherein the heavy chain comprises or consists of the amino acid sequence shown in SEQ ID NO: 74; and the light chain comprises or consists of the amino acid sequence shown in SEQ ID NO: 75.

In the preferred embodiment, the invention provides an anti-CD47 antibody or antigen-binding fragment thereof, wherein the heavy chain comprises or consists of the amino acid sequence shown in SEQ ID NO: 76; and the light chain comprises or consists of the amino acid sequence shown in SEQ ID NO: 75.

In the preferred embodiment, the invention provides an anti-CD47 antibody or antigen-binding fragment thereof, wherein the heavy chain comprises or consists of the amino acid sequence shown in SEQ ID NO: 77; and the light chain comprises or consists of the amino acid sequence shown in SEQ ID NO: 75.

In the preferred embodiment, the invention provides an anti-CD47 antibody or antigen-binding fragment thereof, wherein the heavy chain comprises or consists of the amino acid sequence shown in SEQ ID NO: 78; and the light chain comprises or consists of the amino acid sequence shown in SEQ ID NO: 79.

In the preferred embodiment, the invention provides an anti-CD47 antibody or antigen-binding fragment thereof, wherein the heavy chain comprises or consists of the amino acid sequence shown in SEQ ID NO: 80; and the light chain comprises or consists of the amino acid sequence shown in SEQ ID NO: 79.

In the preferred embodiment, the invention provides an anti-CD47 antibody or antigen-binding fragment thereof, wherein the heavy chain comprises or consists of the amino acid sequence shown in SEQ ID NO: 81; and the light chain comprises or consists of the amino acid sequence shown in SEQ ID NO: 79.

In the preferred embodiment, the invention provides an anti-CD47 antibody or antigen-binding fragment thereof, wherein the heavy chain comprises or consists of the amino acid sequence shown in SEQ ID NO: 82; and the light chain comprises or consists of the amino acid sequence shown in SEQ ID NO: 83.

In the preferred embodiment, the invention provides an anti-CD47 antibody or antigen-binding fragment thereof, wherein the heavy chain comprises or consists of the amino acid sequence shown in SEQ ID NO: 84; and the light chain comprises or consists of the amino acid sequence shown in SEQ ID NO: 83.

In the preferred embodiment, the invention provides an anti-CD47 antibody or antigen-binding fragment thereof, wherein the heavy chain comprises or consists of the amino acid sequence shown in SEQ ID NO: 85; and the light chain comprises or consists of the amino acid sequence shown in SEQ ID NO: 86.

In the preferred embodiment, the invention provides an anti-CD47 antibody or antigen-binding fragment thereof, wherein the heavy chain comprises or consists of the amino acid sequence shown in SEQ ID NO: 87; and the light chain comprises or consists of the amino acid sequence shown in SEQ ID NO: 86.

In the preferred embodiment, the invention provides an anti-CD47 antibody or antigen-binding fragment thereof, wherein the heavy chain comprises or consists of the amino acid sequence shown in SEQ ID NO: 88; and the light chain comprises or consists of the amino acid sequence shown in SEQ ID NO: 75.

In the preferred embodiment, the invention provides an anti-CD47 antibody or antigen-binding fragment thereof, wherein the heavy chain comprises or consists of the amino acid sequence shown in SEQ ID NO: 89; and the light chain comprises or consists of the amino acid sequence shown in SEQ ID NO: 75.

In the preferred embodiment, the invention provides an anti-CD47 antibody or antigen-binding fragment thereof, wherein the heavy chain comprises or consists of the amino acid sequence shown in SEQ ID NO: 90; and the light chain comprises or consists of the amino acid sequence shown in SEQ ID NO: 75.

In the preferred embodiment, the invention provides an anti-CD47 antibody or antigen-binding fragment thereof, wherein the heavy chain comprises or consists of the amino acid sequence shown in SEQ ID NO: 91; and the light chain comprises or consists of the amino acid sequence shown in SEQ ID NO: 79.

In the preferred embodiment, the invention provides an anti-CD47 antibody or antigen-binding fragment thereof, wherein the heavy chain comprises or consists of the amino acid sequence shown in SEQ ID NO: 92; and the light chain comprises or consists of the amino acid sequence shown in SEQ ID NO: 79.

In the preferred embodiment, the invention provides an anti-CD47 antibody or antigen-binding fragment thereof, wherein the heavy chain comprises or consists of the amino acid sequence shown in SEQ ID NO: 93; and the light chain comprises or consists of the amino acid sequence shown in SEQ ID NO: 79.

In the preferred embodiment, the invention provides an anti-CD47 antibody or antigen-binding fragment thereof, wherein the heavy chain comprises or consists of the amino acid sequence shown in SEQ ID NO: 94; and the light chain comprises or consists of the amino acid sequence shown in SEQ ID NO: 83.

In the preferred embodiment, the invention provides an anti-CD47 antibody or antigen-binding fragment thereof, wherein the heavy chain comprises or consists of the amino acid sequence shown in SEQ ID NO: 95; and the light chain comprises or consists of the amino acid sequence shown in SEQ ID NO: 83.

In the preferred embodiment, the invention provides an anti-CD47 antibody or antigen-binding fragment thereof, wherein the heavy chain comprises or consists of the amino acid sequence shown in SEQ ID NO: 96; and the light chain comprises or consists of the amino acid sequence shown in SEQ ID NO: 86.

In the preferred embodiment, the invention provides an anti-CD47 antibody or antigen-binding fragment thereof, wherein the heavy chain comprises or consists of the amino acid sequence shown in SEQ ID NO: 97; and the light chain comprises or consists of the amino acid sequence shown in SEQ ID NO: 86.

In some embodiments, the antibody according to the invention also encompasses the variants of the amino acid sequence of the anti-CD47 antibody, the antibodies competing with any of the antibodies described above for binding to CD47, and the antibodies binding to the same epitopes of CD47 as any of the antibodies described above.

In some embodiments, the anti-CD47 antibody is a monoclonal antibody. In some embodiments, the anti-CD47 antibody is humanized. In some embodiments, the anti-CD47 antibody is a human antibody. In some embodiments, at least a part of the framework sequence of the anti-CD47 antibody is a human consensus framework sequence. In one embodiment, the anti-CD47 antibody of the invention also encompasses the antibody fragments thereof, preferably selected from the group consisting of the following antibody fragments: Fab, Fab'-SH, Fv, scFv or (Fab')$_2$ fragment.

In some embodiments, the anti-CD47 antibody of the invention is a blocking antibody which blocks CD47 binding to SIRPα.

In one aspect, the invention provides nucleic acids encoding any of the anti-CD47 antibodies or fragments thereof above mentioned. In one embodiment, a vector comprising the said nucleic acid is provided. In one embodiment, the vector is an expression vector. In one embodiment, a host cell comprising the vector is provided. In one embodiment, the host cell is eukaryotic. In another embodiment, the host cell is selected from the group consisting of yeast cells, mammalian cells or other cells which are suitable for preparing the antibodies or the antigen binding fragments thereof. In another embodiment, the host cells were prokaryotic.

In one embodiment, the present invention provides a method for preparing an anti-CD47 antibody or fragment thereof (preferably an antigen-binding fragment), wherein the method comprises culturing the host cell under a condition which is suitable for expressing the nucleic acid encoding the said antibody or fragment thereof (preferably the antigen-binding fragment), and optionally isolating the antibody or fragment thereof (preferably the antigen-binding fragment). In a certain embodiment, the method further comprises recovering the anti-CD47 antibody or fragment thereof (preferably the antigen-binding fragment) from the host cell.

In one embodiment, the present invention provides the anti-CD47 antibody or fragment thereof prepared by the method of the invention.

In some embodiments, the invention provides a composition comprising any of the anti-CD47 antibodies or fragments thereof described herein (preferably the antigen-binding fragments thereof), preferably the composition servicing as a pharmaceutical composition. In one embodiment, the composition also comprises pharmaceutical carriers.

In one aspect, the present invention is directed to a method for inhibiting CD47 binding to SIRPα in a subject, comprising administrating to the subject the effective amount of any of the anti-CD47 antibodies or fragments thereof herein. The present invention is directed further to the use of any of the anti-CD47 antibodies or fragments thereof disclosed herein in preparing a composition or medication for inhibiting CD47 binding to SIRPα in a subject.

In one aspect, the present invention is directed to a method for facilitating macrophage phagocytosis in a subject, comprising administrating to the subject the effective amount of any of the anti-CD47 antibodies or fragments thereof herein. The present invention is directed further to the use of any of the anti-CD47 antibodies or fragments thereof disclosed herein in preparing a composition or medication for facilitating macrophage phagocytosis in a subject. In one embodiment, the anti-CD47 antibody of the invention can enhance macrophage phagocytosis by at least 10%, 20%, 30%, 40%, 50%, 60%, 70%, 80%, 90%, 100% or above 100%, compared to a control.

In the another aspect, the present invention is directed to a method for treating a CD47-related disorder in a subject, comprising administrating to the subject the effective amount of any of the anti-CD47 antibodies or fragments thereof herein. The present invention is directed further to the use of any of the anti-CD47 antibodies or fragments thereof disclosed herein in preparing a medication for treating a CD47-related disorder in a subject.

In some embodiments, the CD47-related disorder is a variety of haematological disorders and solid tumors, including, but not limited to acute myelocytic leukemia (AML), chronic myelocytic leukemia, acute lymphocytic leukaemia (ALL), Non-Hodgkin's lymphoma (NHL), multiple myeloma (MM), lymphoma, breast carcinoma, gastric carcinoma, lung cancer, esophageal carcinoma, intestinal carcinoma, ovarian carcinoma, cervical carcinoma, renal carcinoma, pancreatic carcinoma, bladder carcinoma, glioma, melanoma and other solid tumors.

In one aspect, the present invention is directed to a method for immunotherapy on tumors with CD47 being the target, comprising administrating to a subject the effective amount of any of the anti-CD47 antibodies or fragments thereof described herein. The present invention is directed further to the use of any of the anti-CD47 antibodies or fragments thereof disclosed herein in preparing a medication for treating a tumor.

In one aspect, the present invention is directed to a method for treating any disease or disorder which can be ameliorated, delayed, inhibited or prevented by eliminating, inhibiting or decreasing CD47 activity.

In another aspect, the method according to the present invention is further directed to a method for treating a tumor with a combination therapy, comprising administrating to a subject the effective amount of any of the anti-CD47 antibodies or fragments thereof described herein and one or more of other medicaments. In some embodiments, method disclosed therein further comprises co-administering to a subjects an effective amount of the second medicament, while the anti-CD47 antibody or fragment thereof disclosed herein being the first medicament. In one embodiment, the second medicament is a chemotherapeutic agent, radiotherapeutic agent or biomacromolecular drug for treating the relevant diseases. In one embodiment, the biomacromolecular drug is for example various monocolonal antibody medicaments which attack tumor cells through recognition by T cells, e.g., rituximab, cetuximab and trastuzumab. The expression "second medicament" as used herein can not be interpreted as only one kind of medicament besides the first medicament. Thus, the second medicament need not be one medicament, but may constitute or comprise more than one of such medicaments.

In some embodiments, the subjects or individual is a mammal, preferably a human being.

In some embodiments, the anti-CD47 antibody or antigen-binding fragment thereof provided in the present invention may be effective in facilitating macrophage phagocytosis.

In one preferred embodiment, the anti-CD47 antibody or antigen-binding fragment thereof provided in the present invention is surprisingly able to inhibit effectively the growth of the tumor, compared to a control antibody.

In a more preferred embodiment, the anti-CD47 antibody or antigen-binding fragment thereof provided in the present invention enables the complete regression of tumor, which is totally unexpected and has never been reported in the state of the art.

In one aspect, the present invention is directed to a method of detecting the CD47 protein in a sample, comprising (a) contacting the sample with any of the anti-CD47 antibodies or fragments thereof described herein; and (b) detecting formation of the complex between the anti-CD47 antibody or antigen-binding fragment thereof and the CD47 protein. In certain embodiments, the CD47 is a human CD47. In one embodiment, the detection method may be an in vitro or in vivo method. In one embodiment, the anti-CD47 antibody is used to select subjects eligible for therapy with an anti-CD47 antibody. In one embodiment, the anti-CD47 antibody is detectably labelled.

In another aspect, the present invention is directed to a method for determining the efficacy of a tumor therapy, comprising the step of determining the number of the CD47-expressing cancer cells in a sample from a subject before and after the therapy, wherein the decreased number of the CD47-expressing cancer cells indicates that the therapy is effective.

The present invention also encompasses any combination of any of the embodiments described herein. Any of the embodiments or any combination thereof described herein is applicable to each and all anti-CD47 antibodies or fragments thereof, methods and uses of the invention described herein.

BRIEF DESCRIPTION OF THE DRAWINGS

FIG. 1. Affinity assay with flow cytometery on an anti-CD47 antibody in IgG1 format produced in yeasts at the cellular level.

FIG. 2. Blocking of SIRPα binding to a CD47 expressed on CHO cells by the present antibody in IgG1 format produced in yeast cells as assayed with flow cytometery.

FIG. 3. Blocking of SIRPα binding to a CD47 expressed on CHO cells by the present antibody in IgG4 format produced in CHO cells as assayed with flow cytometery.

FIG. 4. Detection of the ability of the present antibody in IgG1 format produced in yeast cells to facilitate phagocytosis of tumor cells by macrophages, the antibody including the antibody-affinity-matured antibodies ADI-29336, ADI-29340, ADI-29341 and ADI-29349 in IgG1 format produced in yeast cells.

FIG. 5. Detection of the ability of the present IgG1 antibody produced in yeast cells to facilitate phagocytosis of tumor cells by macrophages.

FIG. 6. Detection of the ability of the present antibody in IgG4 format produced in CHO cells to facilitate phagocytosis of tumor cells by macrophages.

FIG. 7. Detection of the ability of the present antibody in IgG4 format produced in CHO cells to facilitate phagocytosis of tumor cells by macrophages. Include are ADI-29336, ADI-29340, ADI-29341 and ADI-29349 and ADI-29371.

FIG. 8. Study on the anti-tumor activity of the present antibody ADI-26630 in IgG4 format produced in CHO cells in a mouse model (NOD/SCID Raji tumor model). Wherein FIG. 8B is a enlarged partial view of FIG. 8A.

FIG. 9: Study on the anti-tumor activity of the present antibody ADI-26624 in IgG4 format produced in CHO cells in a mouse model (NOD/SCID Raji tumor model).

FIG. 10: Study on the anti-tumor activity of the present antibodies ADI-26630, ADI29340 and ADI29341 in IgG4 format produced in CHO cells at a dosage of 0.5 mg/kg in a mouse model (NOD/SCID Raji tumor model).

FIG. 11: Study on the anti-tumor activity of the present antibodies ADI-26630, ADI29340 and ADI29341 in IgG4 format produced in CHO cells at a dosage of 5 mg/kg in a mouse model (NOD/SCID Raji tumor model).

FIG. 12: Result of detecting the activity of an anti-CD47 antibody of the invention to facilitate RBC agglutination activity.

DETAILED DESCRIPTION 1.1 Definition

Before the present invention is detailed below, it is to be understood that the present invention is not limited to the particular methodologies, protocols and reagents described herein, as those may vary. It is also to be understood that the terminology used herein is for the purpose of describing the particular embodiments only, and is not intended to limit the scope of the invention, which will be limited only by the appended claims. Unless defined otherwise, all technical and scientific terms used herein have the same meaning as commonly understood by one of ordinary skill in the art to which the invention pertains.

For interpretation of the specification, the following definitions will be applied and wherever appropriate, terms used in the singular may also include the plural and vice versa. It is to be understood that the terminology used herein is for the purpose of describing specific embodiments only and is not intended to be limiting.

The term "about" used in combination of a numerical value is intended to encompass the numerical values in a range from a lower limit less than the specified numerical value by 5% to an upper limit greater than the specified numerical value by 5%.

The term "conservation substitution" refers to substitution of an amino acid by another amino acid in the same class, for example, substitution of an acidic amino acid by another acidic amino acid, substitution of a basic amino acid by another basic amino acid, and substitution of a neutral amino acid by another neutral amino acid. Exemplary substitutions are shown in the Table below:

| Original residue | Exemplary substitution | Preferred substitution |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen binding activity. An intact antibody will generally comprise at least two of full-length heavy chains and two full-length light chains, while in certain circumstances can comprises fewer chains, e.g. the naturally-occurring antibodies in camel can comprises heavy chains only.

The term "antigen binding moiety" as used herein refers to a moiety that specifically binds to a target antigen. The term convers antibodies and other natural molecules (e.g., receptors, ligands) or synthetic molecules (e.g., DARPins) which can specifically binds to a target antigen. In one preferred embodiment, the antigen-binding moiety of an antibody according to the invention is an antibody fragment.

The terms "full-length antibody", "intact antibody," and "whole antibody" are used herein interchangeably to refer to an antibody having a structure substantially similar to a native antibody structure or having heavy chains that contain an Fc region as defined herein.

As used herein, the terms "monoclonal antibody" or "monoclonal antibody composition" refer to a preparation of antibody molecules of single amino acid composition, and are not to be construed as requiring production of the antibody by any particular method. Monoclonal antibodies or antigen-binding fragments thereof can be produced, for example, by hybridoma technologies, recombinant technologies, phage display technologies, synthetic technologies, e.g., CDR-grafting, or combinations of such or other technologies known in the art.

As used herein, the terms "bind to" and "specifically bind to" refers to an antibody or antigen-binding moiety binding to an antigenic epitope in an in-vitro assay, preferably in a bio-light interferometry (ForteBio) using a purified wild-type antigen. In certain embodiments, an antibody or antigen-binding moiety is said to specifically bind an antigen when it preferentially recognizes its target antigen in a complex mixture of proteins and/or macromolecules.

Depending on the amino acid sequence of the constant region of the heavy chains, antibodies are divided with "Class": IgA, IgD, IgE, IgG, and IgM, and several of these classes may be further divided into subclasses, e.g., IgG1, IgG2, IgG3, and IgG4, IgA1 as well as IgA2. The heavy chain constant regions that correspond to the different classes of antibodies are called α, δ, ε, γ and μ. The light chain constant regions (CL) which can be found in all five classes of antibodies are referred to kappa and lambda. Within full-length light and heavy chains, the variable and constant regions are typically joined by a "J" region of about 12 or more amino acids, and the heavy chain also includes a "D" region of about 10 more amino acids. See e.g. Fundamental Immunology, Ch.7 (Paul, W. Ed., 2$^{nd}$ Edition, Raven Press, N.Y. (1989)) (which is incorporated herein by reference in its entirety for all purposes). The variable regions of each light/heavy chain pair form typically the antigen-binding sites.

The term "variable region" or "variable domain" refers to the domain of an antibody that is involved in the antibody binding to antigen. The variable domains of the heavy chain and light chain of a native antibody generally have similar structures, with each domain comprising four conserved framework regions (FRs) and three complementary-determining regions. (see, e.g, Kindt et al., Kuby Immunology, 6th Edition, W. H. Freeman and Co., p. 91 (2007)). A single VH or VL domain may be sufficient to confer antigen-binding specificity. Furthermore, antibodies that bind a particular antigen may be isolated using a VH or VL domain from an antibody that binds to the antigen to screen a library of complementary VL or VH domains, respectively. See e.g. Portolano, et al., J. Immunol. 150: 880-887 (1993); Clarkson, et al., Nature 352: 624-628 (1991).

The variable regions exhibit typically the same general structure of relatively conserved framework regions (FRs) joined by three hypervariable regions, the latter also called complementarity determining regions or CDRs. Generally, CDRs of the two chains from each pair are aligned by the framework regions, which CDRs enable specific binding to an epitope. From N-terminus to C-terminus, two light and heavy chain variable regions typically comprise the domains FR1, CDR1, FR2, CDR2, FR3, CDR3 and FR4.

"Complementarity determining regions" or "CDR regions" or "CDRs" or "hyper variable regions" (which can be used interchangeably with hypervariable regions "HVR"), is an amino acids region in an antibody variable region, which is primarily responsible for binding to an epitope of an antigen. Heavy and the light chain CDRs typically are called CDR1, CDR2 and CDR3, sequentially numbered from the N-terminus. CDRs located in the heavy chain variable domain of an antibody are referred to as HCDR1, HCDR2 and HCDR3, and CDRs located in the light chain variable domain of an antibody are referred to as LCDR1, LCDR2 and LCDR3.

Methods and techniques for identifying the CDR sequences of a given VH or VL are well-known in the art: The Kabat Complementarity Determining Regions (CDRs) are identified on the basis of sequence variability and are the most commonly used (Kabat et al., Sequences of Proteins of Immunological Interest, 5th Ed. Public Health Service, National Institutes of Health, Bethesda, Md. (1991)), Chothia definition refers instead to the location of the structural loops (Chothia, et al. (1987) J. Mol. Biol. 196: 901-917; Chothia, et al. (1989) Nature 342: 877-883), AbM HVR is a compromise between the Kabat HVRs and Chothia structural loops, and are used by Oxford Molecular's AbM antibody modeling software, "contacting" (Contact) HVR is on the basis of analysis of a complicated crystalline structure available. According to the different conventions for identifying the CDRs, each of the HVR/CDR residues in these HVRs is described as follows.

| CDR | Kabat definition | AbM definition | Chothia definition | Contact definition |
|---|---|---|---|---|
| (Kabat numbering system) | | | | |
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| (Chothia numbering system) | | | | |
| HCDR1 | H31-H35 | H26-H35 | H26-H32 | H30-H35 |
| (Kabat numbering system) | | | | |
| HCDR2 | H50-H65 | H50-H58 | H53-H55 | H47-H58 |
| HCDR3 | H95-H102 | H95-H102 | H96-H101 | H93-H101 |

In one embodiment, the CDR of an antibody of the invention has the CDR sequence located at the Kabat residue position below according to Kabat numbering system:

Positions 24-34 (LCDR1), Positions 50-56 (LCDR2), and Positions 89-97 (LCDR3) in the VL, and Positions 27-35 (HCDR1), Positions 50-65 (HCDR2), and Positions 93-102 (HCDR3) in VH.

A CDR can also be identified on the basis of the position having the same Kabat number as the reference CDR sequence (e.g., one of the exemplary CDRs of the invention).

An "antibody fragment" refers to a molecule other than an intact antibody that comprises a portion of an intact antibody that binds the antigen to which the intact antibody binds.

"Affinity" refers to the strength of the sum total of non-covalent interactions between a single binding site of a molecule (e.g., an antibody) and its binding partner (e.g., an antigen). Unless specified otherwise, when used herein, "binding affinity" refers to intrinsic binding affinity which reflects a 1:1 interaction between the members of a binding pair (e.g., an antibody and an antigen). The affinity of a molecule X for its partner Y can generally be represented by the dissociation constant (Kd). Affinity can be measured by the common methods known in the art, including those known in the art and described herein.

The term "compete" when used in the context of antigen-binding proteins (e.g., neutralizing antigen-binding proteins or neutralizing antibodies) that compete for the same epitope means competition between the antigen-binding proteins which is determined by an assay below: the antigen-binding protein to be tested (e.g., an antibody or immunologically functional thereof) in the assay prevents or inhibits (e.g., reduces) specific binding of a reference antigen-binding protein (e.g., a ligand or reference antibody) to a common antigen (e.g., a CD47 or fragment thereof). A number of competitive binding assays can be used for determining whether an antigen-binding protein competes with another one. For example, these assays are solid phase direct or indirect radioimmunoassay (RIA), solid phase direct or indirect enzyme immune assay (EIA), sandwich competition assay (e.g., see Stahli et al., 1983, Methods in Enzymology 9: 242-253). Typically, the assay involves the use of purified antigen bound to a solid surface or cells loaded with either of an unlabeled antigen-binding protein to be tested and a labeled reference antigen-binding protein. Competitive inhibition is measured by determining the amount of the label bound to the solid surface or cells in the presence of the antigen-binding protein to be tested. Usually the antigen-binding protein to be tested is present in excess. The antigen-binding protein identified by the competition assay (the competitive antigen-binding protein) includes: the antigen-binding protein that binds to the same epitope as the reference antigen-binding protein; and the antigen-binding protein that binds to an adjacent epitope sufficiently proximal to the epitope bound by the reference antigen-binding protein for mutual steric hindrance of the two epitopes to occur. Additional details regarding methods for determining competitive binding are provided in the Examples herein. Usually, when present in excess, a competing antigen-binding protein will inhibit (e.g., reduce) specific binding of a reference antigen-binding protein to a common antigen by at least 40-45%, 45-50%, 50-55%, 55-60%, 60-65%, 65-70%, 70-75% or 75% or more. In some instance, binding is inhibited by at least 80-85%, 85-90%, 90-95%, 95-97% or 97% or more.

A "human antibody" is one which possesses an amino acid sequence which corresponds to that of an antibody generated by a human or a human cell or derived from a non-human source that utilizes human antibody repertoires or other human antibody-encoding sequences. This definition of a human antibody explicitly excludes a humanized antibody comprising non-human antigen-binding residues.

A "human consensus framework" refers to a framework that represents the most commonly occurring amino acid residues in a selection of human immunoglobulin VL or VH framework sequences. Generally, the selection of human immunoglobulin VL or VH sequences is a selection from a subtype of variable domain sequences. Generally, the subtype of the sequence is the one in Kabat, et al., Sequences of Proteins of Immunological Interest, 5th edition, NIH Publication 91-3242, Bethesda Md. (1991), Vols 1-3. In one embodiment, for the VL, the subtype is the subtype kappa I as in Kabat et al. (see above). In one embodiment, for the VH, the subtype is the subtype kappa III as in Kabat et al. (see above).

A "humanized" antibody refers to a chimeric antibody comprising amino acid residues from non-human HVRs and amino acid residues from human FRs. In some embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "diabodies" refers to antibody fragments having two antigen-binding sites, which fragments comprise a heavy chain variable domain (VH) connected to a light chain variable domain (VL) in the same polypeptide chain (VH-VL). By using a linker that is too short to enable pairing between the two domains on the same chain, the domains are forced to pair with the complementary domains of another chain so as to create two antigen-binding sites. Diabodies may be bivalent or bispecific. Diabodies are described more fully in e.g. EP 404,097; WO 1993/01161; Hudson, et al., Nat. Med. 9: 129-134 (2003); and Hollinger, et al., Proc. Natl. Acad. Sci. USA 90: 6444-6448 (1993). Tribodies and Terabodies are also described in Hudson, et al., Nat. Med. 9: 129-134 (2003).

"Effector functions" refer to those biological activities which are attributable to the Fc region of an antibody and which vary with the antibody isotype. Examples of effector functions of antibodies include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B-cell activation.

The terms "effective amount" and "therapeutically effective amount" refer to an amount or dosage of the antibody or antigen-binding fragment thereof of the invention which after administered to a subject in a single or multiple dosages, generates the expected effects in the treated subject, including amelioration of the subject's disorder (e.g., amelioration of one or more symptoms) and/or the delayed progression of the symptoms and like. "Effective amount" and "therapeutically effective amount" can also refer to an amount sufficient to decrease CD47 signals (e.g. see Yamauchi, et al., 2013 Blood, January 4; Soto-Pantoja, et al., 2013 Expert Opin Ther Targets, 17: 89-103; Irandoust, et al., 2013 PLoS One, Epub January 8; Chao, et al., 2012 Curr Opin Immunol, 24: 225-32; Theocharides, et al., 2012 J Exp Med, 209 (10): 1883-99), for example, an amount of an antibody sufficient to decrease the signal for inhibiting phagocytosis generated from interaction between CD47/SIRPα on the CD47/SIRPα signaling axis in macrophages, that is, the antibody of the invention facilitate macrophage-mediated phagocytosis of CD47-expressing cells.

In one embodiment, the effective amount of the anti-CD47 antibody of the invention can enhance/increase macrophage phagocytosis by 10%, 20%, 30%, 40%, 50%, 60%, 70%, 80%, 90% or 100%, compared to the control.

Therapeutically effective amounts can be determined easily by physicians in charge as those of skill in the art with consideration of a variety of the following factors: the species of the mammal; size, age and general health thereof; the disease involved; the extent or severity of the disease; the response of an individual patient; the particular antibody administered; the mode of administration; the bioavailability profile of the formulation administered; the selected dose regimen; and use of any concurrent therapy, etc.

As described above, in certain circumstances, the interaction between an antibody and the target antigen thereof will interfere with the functionality of the target. Furthermore, the administration dosage required is not only dependent on the binding affinity of an antibody to its specific antigen, but also the clearance rate of an antibody given in an administered subject. As a non-limiting example, therapeutically effective dose of an antibody or an antibody fragment of the invention is typically in a range from about 0.1 mg/kg of body weight to about 100 mg/kg of body weight. In a few embodiments, the antibody of the invention is administered in a subject at a dose of 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 50 mg/kg, 75 mg/kg, 100 mg/kg or higher. The common dose frequency ranges for example from twice per day to once per week, once every two weeks, once every three weeks, once a month, once every two months, once every three months, once half a year.

The term "block" used herein indicate the decreased CD47 signaling in the presence of the antibody of the invention. Blocking of CD47-mediated signaling means that the CD47 signaling level in the presence of the anti-CD47 antibody of the invention is lower than the control CD47 signaling level (namely the CD47 signaling level in the absence of the antibody of the invention), with the decreased range of greater than or equal to 5%, 10%, 20%, 25%, 30%, 40%, 50%, 60%, 70%, 75%, 80%, 90%, 95%, 99% or 100%. The CD47 signaling level can be measured with many standard techniques, such as luciferase reporter assays which measure the activation of the downstream gene and/or the activation responding to CD47. A person of skill in the art is to understood that the CD47 signaling level can be measured with many tests, including e.g. commercially available kits.

The terms "host cell," "host cell line," and "host cell culture" are used interchangeably and refer to a cell into which exogenous nucleic acid has been introduced, including the progeny of this cell. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "cytotoxic agent" is used herein to refer to a substance that inhibits or prevents a cellular function and/or causes cell death or destruction.

The term "vector" when used herein denotes a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

An "immunoconjugate" is an antibody conjugated to one or more heterologous molecule(s), including but not limited to a cytotoxic agent.

An "individual" or "subject" include a mammal. Mammals include, but are not limited to, domesticated animals (e.g. cows, sheep, cats, dogs, and horses), primates (e.g. humans and non-human primates such as monkeys), rabbits, and rodents (e.g. mice and rats). In some embodiments, the individual or subject is a human.

An "isolated" antibody is one which has been separated from a component of its natural environment. In some embodiments, an antibody is purified to the purity of greater than 95% or 99% as determined by, for example, electrophoresis (e.g., SDS-PAGE, isoelectric focusing (IEF), capillary electrophoresis) or chromatography (e.g., ion exchange or reverse phase HPLC). For review of methods for assessment of antibody purity, see, e.g., Flatman et al., J. Chromatogr. B848: 79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated nucleic acid encoding an anti-CD47 antibody or antigen-binding fragment thereof" refers to one or more nucleic acid molecules encoding the heavy and light chains of the antibody (or antigen-binding fragment thereof), including such nucleic acid molecule(s) present in a single vector or separate vectors, and such nucleic acid molecule(s) present at one or more locations in a host cell.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved with various methods in the art, for instance, using publicly available computer software such as BLAST, BLAST-2, ALIGN or MEGALIGN (DNASTAR) software. A person of skill in the art can determine appropriate parameters for measuring alignment, including any algorithms required to achieve maximal alignment over the full-length of the sequences being compared.

When referring to percentages of sequence identity in the present application, these percentages are calculated over the fully-length of the longer sequence, unless especially specified otherwise. Calculation over the fully-length of the longer sequence is applicable to both nucleic acid and polypeptide sequences.

The terms "red blood cell" and "RBC" is synonymous and used interchangeably.

The term "agglutination" refers to cellular clumping, and the term "hemagglutinating reaction" refers to clumping of a specific subset of cells (namely red blood cells). Consequently, hemagglutinating reaction is one type of agglutination.

1.2 Anti-CD47 Antibody of the Invention

The terms "integrin-associated protein (IAP)" and "CD47" when used herein refers to any native CD47 from any vertebrate source, including mammals such as primates (e.g. humans) and rodents (e.g., mice and rats), unless otherwise indicated. The term encompasses "full-length", unprocessed CD47 as well as any form of CD47 or any fragment thereof that results from processing in the cell. The term also includes naturally occurring variants of CD47, e.g., splice variants or allelic variants.

The terms "anti-CD47 antibody", "anti-CD47", "CD47 antibody" and "an antibody that binds to CD47" refer to an antibody that is capable of binding to CD47 protein or a fragment thereof with sufficient affinity such that the antibody can be used as a diagnostic and/or therapeutic agent in targeting CD47. In one embodiment, the extent of binding of an anti-CD47 antibody to an unrelated, non-CD47 protein is less than about 10% of the binding of the antibody to CD47 as measured, e.g., by a radioimmunoassay (RIA). In some embodiments, an anti-CD47 antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or below $10^{-8}$ M, e.g., from $10^{-8}$ M to $10^{-13}$ M, e.g., from $10^{-9}$ M to $10^{-13}$ M).

In some embodiments, the anti-CD47 antibody or antigen-binding fragment thereof according to the present invention comprises substitutions, insertions or deletions. In the preferred embodiment, substitutions, insertions or deletions occur in regions outside of CDRs (e.g., in the FRs). Alternatively, the anti-CD47 antibody of the invention comprises post-translational modifications on the light chain variable region, the heavy chain variable region, the light or heavy chain.

An anti-CD47 antibody provided in the invention exhibits inhibitory activity, e.g. for inhibiting CD47 expression (e.g., inhibiting CD47 expression on the surface of a cell), activity and/or signaling, or interfering with the interaction between CD47 and SIRPα. An anti-CD47 antibody provided in the invention results in fully or partly decreased or regulated CD47 expression or activity after binding to or interacting with CD47 (e.g., human CD47). The biological function of CD47 is decreased or regulated completely, significantly or partially after interaction between the antibody and the human CD47 polypeptide and/or peptide. When the level of CD47 expression or activity in the presence of an antibody described herein is decreased by at least 95% (e.g., by 96%, 97%, 98%, 99% or 100%) compared to the level of CD47 expression or activity in the absence of interaction with (e.g., binding to) the antibody, the antibody is considered to be able to completely inhibit CD47 expression or activity. The level of CD47 expression or activity in the presence of an anti-CD47 antibody described herein is decreased by at least 50% (e.g., by 55%, 60%, 75%, 80%, 85% or 90%) compared to the level of CD47 expression or activity in the absence of binding to the anti-CD47 antibody, the anti-CD47 antibody is considered to be able to significantly inhibit CD47 expression or activity. The level of CD47 expression or activity in the presence of an antibody described herein is decreased by less than 95% (e.g., by 10%, 20%, 25%, 30%, 40%, 50%, 60%, 75%, 80%, 85% or 90%) compared to the level of CD47 expression or activity in the absence of interaction with (e.g., binding to) the antibody, the antibody is considered to be able to partially inhibit CD47 expression or activity.

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, it may be desirable to create cysteine engineered antibodies, e.g., "thioMAbs," in which one or more residues of an antibody are substituted with cysteine residues.

In certain embodiments, an antibody provided herein may be further modified to contain other non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propylene glycol homopolymers, polypropylene oxide/ethylene oxide co-polymers, polyoxyethylated polyols (e.g., glycerol), polyvinyl alcohol, and mixtures thereof.

In some embodiments, the invention encompasses fragments of an anti-CD47 antibody. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

In some embodiments, the anti-CD47 antibody of the invention is a humanized antibody. Different methods for humanized antibody are known to the skilled worker, for example, as reviewed by Almagro & Fransson, the content of which is incorporated herein by reference in its entirety (Almagro J. C. and Fransson J., (2008) Frontiers in Bioscience 13: 1619-1633). Almagro & Fransson differentiated from rational approaches and empirical approaches. The rational approach is characterized by generating a few engineered antibody variants and evaluating their binding properties or any other properties of interest. If the designed variants does not exert the expected effect, a new round of designation and binding evaluation will be initiated. The rational approach includes CDR-grafting, Resurfacing, Superhumanization and Human String Content Optimization. By contrast, the empirical approach bases upon generating a large library of humanization variants and selecting the optimal clones with enrichment technique or high throughput screening. Thereby, the empirical approach is dependent upon a reliable selection and/or screening system capable of searching against a large number of antibody variants. In vitro display technologies, e.g. phage display and ribosome display, meet to these requirement and are well known to the skilled. The empirical approach includes FR library, Guided selection, Framework-shuffling and Humaneering.

In some embodiments, the anti-CD47 antibody of the invention is a human antibody. Human antibodies can be prepared using various techniques known in the art. Human antibodies are generally described in van Dijk and van de Winkel, Curr. Opin. Pharmacol 5: 368-74 (2001) and Lonberg, Curr. Opin. Immunol 20: 450-459 (2008).

Antibodies of the invention may be isolated by screening combinatorial libraries for antibodies with the desired activity or activities. For example, a variety of methods are known in the art for generating phage display libraries and screening in these libraries for antibodies possessing the desired binding characteristics. These methods are for example reviewed in Hoogenboom, et al., in: Methods in Molecular Biology 178: 1-37 (O' Brien, et al., Ed., Human Press, Totowa, N.J., 2001), and further described for example in McCafferty, et al., Nature 348:552-554; Clackso, et al., Nature 352: 624-628 (1991); Marks, et al., J. Mol. Biol. 222: 581-597 (1992); Marks and Bradbury, in: Methods in Molecular Biology 248: 161-175 (Lo, Ed., Human Press, Totowa, N J, 2003); Sidhu, et al., J. Mol. Biol. 338 (2): 299-310 (2004); Lee, et al., J. Mol. Biol 340 (5): 1073-1093 (2004); Fellouse, Proc. Natl. Acad. Sci. USA 101 (34): 12467-12472 (2004); and Lee et al, J. Immunol. Methods 284 (1-2): 119-132 (2004).

An "antibody and antigen-binding fragment thereof" suitable for use in this invention includes, but is not limited to, polyclonal, monoclonal, monovalent, bispecific, heterogeneously conjugated, multispecific, recombination, heterogeneous, heterogeneously hybriydized, chimeric, humanized (especially grafted with CDR), deimmunized, or human antibodies, Fab fragments, Fab' fragments, F(ab')$_2$ fragments, fragments produced from a Fab expression library, Fd, Fv, disulphide-linked Fvs (dsFvs), single chain antibodies (e.g., scFvs), dibodies or terabodies (Holliger P., et al (1993) Proc. Natl. Acad. Sci. U.S.A 90 (14), 6444-6448), nanobodies (also called single domain antibodies), anti-idiotypic (anti-Id) antibodies (including e.g. anti-Id antibodies against an antibody of the invention) and epitope-binding fragments of any one above-mentioned.

In some embodiments, an antibody of the present invention can be monospecific, bispecific or multispecific. A multispecific monoclonal antibody may be specific to different epitopes on a target polypeptide or may contain antigen-binding domains specific to more than one of target polypeptides. See e.g., Tutt et al., (1991) J. Immunol. 147: 60-69. A monoclonal anti-CD47 antibody can be linked to or co-expressed with another functional molecule (e.g., another peptide or protein). For example, an antibody or fragment thereof can be functionally linked (e.g., by chemical coupling, genetic fusion, noncovalent association or otherwise) to one or more other molecule, so as to create bi- or multi-specific antibodies have the second or more binding specificty.

In some embodiments, the antibody of the invention bind to human CD47 protein.

1.3 Nucleic Acids of the Present Invention and Host Cells Comprising the Same In one aspect, the invention provides nucleic acids encoding any of the anti-CD47 antibodies or fragments thereof above mentioned. The nucleic acids may encode an amino acid sequence comprising the light and/or heavy chain variable regions of an antibody, or an amino acid sequence comprising the light and/or heavy chains of an antibody In one embodiment, one or more vectors comprising the nucleic acids are provided. In one embodiment, the vector is an expression vector.

In one embodiment, a host cell comprising the vector is provided. Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523; and also Charlton, In: Methods in Molecular Biology, Vol. 248 (Lo, B. K. C. (ed.), Humana Press, Totowa, N J (2003), p. 245-254, describing expression of antibody fragments in E. coli). After expression, the antibody may be isolated from the bacterial cell paste in a soluble fraction and can be further purified.

In one embodiment, the host cell is eukaryotic. In another embodiment, the host cell is selected from the group consisting of yeast cells, mammalian cells or other cells which are suitable for preparing the antibodies or the antigen binding fragments thereof. For example, eukaryotic microbes such as filamentous fungi or yeasts are the suitable cloning or expression hosts for antibody-encoding vectors, including fungi and yeast strains whose glycosylation pathways have been "humanized", resulting in the production of an antibody with a partially or fully human glycosylation pattern. See Gerngross, Nat. Biotech. 22: 1409-1414 (2004), and Li, et al., Nat. Biotech. 24: 210-215 (2006). Host cells suitable for the expressing glycosylated antibodies are also derived from multicellular organisms (invertebrates and vertebrates). Vertebrate cells may also be used as hosts. For example, mammalian cell lines that are adapted to grow in suspension may be used. Other examples of useful mammalian host cell lines are monkey kidney CV1 lines (COS-7) transformed with SV40; human embryonic kidney lines (293 or 293T cells, such as described e.g. in Graham, et al., J. Gen Virol. 36: 59 (1977)). Examples of useful mammalian host cell lines include Chinese hamster ovary (CHO), including DHFR-CHO cells (Urlaub, et al., Proc. Natl. Acad. Sci. USA 77: 216 (1980)); and myeloma cell lines such as YO, NS0 and Sp2/0. For a review of certain mammalian host cell lines suitable for antibody production, see, e.g., Yazaki and Wu, In: Methods in Molecular Biology, Vol. 248 (B. K. C. Lo, (Ed.), Humana Press, Totowa, N.J.), p. 255-268 (2003).

In one embodiment, a method of preparing an anti-CD47 antibody is provided, wherein the method comprises culturing a host cell comprising a nucleic acid encoding the antibody, as provided above, under conditions suitable for expression of the antibody, and optionally recovering the antibody from the host cell (or host cell culture medium). For recombinant production of an anti-CD47 antibody, nucleic acid encoding an antibody, e.g., the antibody described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

1.4 Pharmaceutical Compositions and Pharmaceutical Formulations

The present invention further provides pharmaceutical compositions comprising one or more monocolonal antibodies which binds to CD47 or immunologically active fragment thereof. It should be understood that the anti-CD47 antibody or the pharmaceutical composition provided in the present invention may be formulated into carriers, excipients and other agents suitable in a formulation for co-administration, resulting in improved transfer, delivery, tolerance, and the like.

The term "pharmaceutical composition" refers to a formulation which is present in a form so as to permit the biological activity of the active ingredient contained in the formulation to be effective, and which contains no additional components that are unacceptably toxic to a subject to which the formulation would be administered.

The term "pharmaceutical carrier" refers to diluents, adjuvants (e.g. Freund's adjuvant (complete or incomplete)), excipients, or vehicles with which the therapeutic agent is administered.

For use herein, "treatment" refers to alleviate, interrupt, retard, relief, cease, reduce, or revert progression or severity of the existing symptom, disorder, condition or disease, and avoid relapse of the relevant disease.

In some embodiments, the invention comprises an anti-CD47 monocolonal antibody conjugated to a therapeutic module, such as a cytotoxic agent or an immunosuppressive agent ("immunuoconjugate"). Cytotoxic agents include any of remedies detrimental to cells. Examples of cytotoxic agents suitable for formation of an immunuoconjugate (e.g., chemotherapeutic agents) are known in the field. See e.g. WO05/103081. For example, cytotoxic agents include, but not are limited to: Radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents known.

The present invention further includes a composition comprising an anti-CD47 antibody (including a pharmaceutical compositions or pharmaceutical formulation) and a composition comprising a polynucleic acid encoding anti-CD47 antibody. In certain embodiments, the composition comprises one or more antibodies which bind to CD47 or one or more polynucleic acids encoding one or more antibodies which bind to CD47. These compositions may further comprises suitable pharmaceutical carriers, such as pharmaceutical excipients known in the field, including buffering agents.

The pharmaceutical compositions of the invention can comprise an antibody of the invention and pharmaceutical carriers. These pharmaceutical composition can be contained in a kit, such as a diagnostic kit.

Pharmaceutical carriers suitable for use in this invention may be sterile liquids, such as water and oils, including those of petroleum, animal, vegetable or synthetic origin, such as peanut oil, soybean oil, mineral oil, sesame oil and the like. Water is the preferable carrier when the pharmaceutical composition is administered intravenously. Saline solutions and aqueous dextrose and glycerol solutions can also be used as liquid carriers, especially for injectable solutions. Suitable pharmaceutical carriers include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. For the usage of excipients and use thereof, see also "Handbook of Pharmaceutical Excipients", 5$^{th}$ Edition, R. C. Rowe; P. J. Seskey and S. C. Owen, Pharmaceutical Press, London, Chicago. The compositions, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, and saccharin.

Pharmaceutical formulations comprising an anti-CD47 antibody of the invention described herein can be prepared by mixing the anti-CD47 antibody of the invention having the desired degree of purity with one or more optional pharmaceutical carriers (Remington's Pharmaceutical Sciences, 16th Edition, Osol, A. Ed. (1980)), preferably in the form of lyophilized formulations or aqueous solutions.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The pharmaceutical compositions or formulations of the invention can further contain more than one active ingredients as necessary for the particular indication being treated, preferably those with complementary activities that do not adversely affect each other. For example, statins are also ideally provided with. The active ingredients are present appropriately in combination at amounts effective to use of interest.

Sustained-release formulations may be prepared. Suitable examples of sustained-release formulations include semipermeable matrices of solid hydrophobic polymers containing the antibody, which matrices are the shaped articles, e.g. films, or microcapsules.

1.5 Therapeutic Methods With Antibodies and Use Thereof

In one aspect, the present invention is directed to a method for inhibiting and/or antagonizing CD47 binding to SIRPα in a subject, comprising administrating to the subject the effective amount of any of the anti-CD47 antibodies or fragments thereof described herein. In another aspect, the present invention is directed to a method for facilitating phagocytosis of phagocytic cells in a subject, comprising administrating to the subject the effective amount of any of the anti-CD47 antibodies or fragments thereof described herein. In one aspect, the present invention is directed to a method for treating the relevant disease with CD47 being the therapeutic target, comprising administrating to a subject the effective amount of any of the anti-CD47 antibodies or fragments thereof described herein. In one aspect, the present invention is directed to a method for any disease or disorder which can be ameliorated, slowed, inhibited or prevented by eliminating, inhibiting or decreasing CD47 binding to SIRPα. In another aspect, the present invention provides methods for treating a cancer or tumor in a subject in need thereto, for alleviating the symptoms of the cancer or tumor in the subject, and for avoiding relapse of the cancer or tumor in the subject, through administering to the subject the anti-CD47 antibody or fragments thereof of the invention.

In on aspect, the anti-CD47 antibody, the antigen-binding fragment thereof and the pharmaceutical composition comprising the same which are provided in the present invention may be used as a therapeutic agent for diagnosis, prognostication, monitoring, treatment, mitigation and/or phrophylaxis of a disease and disorder relevant to aberrant CD47 expression, activity and/or signaling in a subject. When identifying the presence of the disease and disorder relevant to aberrant CD47 expression, activity and/or signaling in a subject with a standard assay, the anti-CD47 antibody, the antigen-binding fragment thereof and the pharmaceutical composition comprising the same disclosed herein may be administrated.

In further aspects, the present invention provides the use of anti-CD47 antibody in manufacturing or preparing a medication for treating the relevant disease or disorder mentioned above.

In certain embodiments, the method and use described herein further include administering to said individual the effective amount of at least one additional therapeutic agent, e.g., a chemotherapeutic agent, radiotherapeutic agent or biomacromolecular drug. In one embodiment, the biomacromolecular drug is for example various monocolonal antibody medicaments which attack tumor cells through recognition by T cells, e.g., rituximab, cetuximab and trastuzumab.

The above-mentioned combination therapy comprises combined administration (in which more than two of the therapeutic agents are included in the same formulation or the individual formulations) and separate administration, in which administration of the anti-CD47 antibody of the invention can occur prior to, simultaneously, and/or following, administration of the additional therapeutic agent and/or adjuvant.

An antibody according to the invention (and any of the additional therapeutic agents) can be administered by any suitable means, including parenteral, intrapulmonary, and intranasal administration, and, if desired for local treatment, intralesional administration. Parenteral infusions include intramuscular, intravenous, intraarterial, intraperitoneal, or subcutaneous administration. Administration can be via a suitable route, via injection, for example intravenous or subcutaneous injection, depending on the short-term or long-term nature of the administration to some extent. Various dosing schedules including but not limited to single or multiple administrations over various time-points, bolus administration, and pulse infusion are contemplated herein.

For the prevention or treatment of a disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In another aspect, the antibody of the invention can be useful in detecting the course of a therapy for the CD47-related disease in vivo or in vitro. For example, whether or not a particular therapy for treating diseases or alleviating symptoms is effective can be determined by measuring the increased or decreased number of the CD47-expressing cells (for example cancer cells).

Most anti-CD47 antibodies are reported to induce hemagglutinating reaction of human red blood cells. Hemagglutination is an example of homotypic interaction, wherein treatment with a bivalency CD47 binding entity induces aggregation or agglutination of two CD47-expressing cells. For example, an anti-CD47 antibody MABL as a whole IgG or F(ab')$_2$ was reported to enable hemagglutinating reaction of red blood cells, and the effect was weaken only if MABL was altered into a scFv or a divalent scFv (e.g., Uno S, Kinoshita Y, Azuma Y, et al., Antitumor activity of a monoclonal antibody against CD47 in xenograft models of human leukemia, Oncol Rep 2007; 17:1189-94; Kikuchi Y, Uno S, Yoshimura Y, et al., A bivalent single-chain Fv fragment against CD47 induces apoptosis for leukemic cells, Biochem Biophys Res Commun 2004; 315: 912-8). The other known anti-CD47 antibodies (including B6H12, BRC126 and CC2C6) can also results in hemagglutinating reaction of RBC. Consequently, agglutination of the cells is the major limitation on therapeutically targeting CD47 with the existing whole IgG antibodies.

Given that most antibodies disclosed in the art which block interaction of CD47 with SIPRα to facilitate phagocytosis will result in apparent agglutination of cells, there is still a great need for novel anti-CD47 antibodies which is not only able to facilitate effectively macrophage phagocytosis, but also does not lead to agglutination of cells. The need in this respect is met by the anti-CD47 antibodies disclosed in the present application, which not only may be effective to facilitate phagocytosis, even exert excellent effects of anti-tumor growth and tumor elimination, but also do not result in apparent agglutination of cells while exerting therapeutic effects, thereby having significantly reduced side effects.

A person skilled in the art may quantify the agglutination level with the conventional experiment, e.g. hemagglutinating reaction of RBC. For example, a hemagglutination test can be performed by a person skilled in the art in presence of the anti-CD47 antibody of the invention, followed by measuring the area of the RBC spots to determine the level of hemagglutinating reaction, as described in the Examples below. In some cases, comparison was performed between the areas of the RBC spots in the presence of the anti-CD47 antibody of the invention and in the absence of the anti-CD47 antibody of the invention (namely under a condition of zero hemagglutinating reaction), as well as in the presence of the other anti-CD47 antibodies known. In this manner, the hemagglutinating reaction was quantified against the base line control. The larger the area of the RBC spots, the higher the level of hemagglutinating reaction. Alternatively, the hemagglutinating reaction can also quantified by density analysis of the RBC spots.

1.6 Methods and Compositions for Diagnostics and Detection

In certain embodiments, any of the anti-CD47 antibodies or antigen-binding fragments thereof provided herein is useful for detecting the presence of CD47 in a biological sample. The term "detecting" as used herein includes quantitative or qualitative detection. In certain embodiments, a biological sample is blood, serum or other liquid samples of biological sources. In certain embodiments, a biological sample comprises a cell or tissue.

In certain embodiments, labeled anti-CD47 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), fluorescein, 2,3-dihydrophthalazinediones, horseradish peroxidase (HR), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor, such as HR, lactoperoxidase, or microperoxidase; biotin/avidin, spin labels, bacteriophage labels, stable free radicals, and the like.

The invention is further illustrated with the following examples. However, it should be understood that the invention is described with the examples in an illustrative manner other than limiting one, and various modifications may be made by the person skilled in the art.

1.7 Sequences of the Exemplary Anti-CD47 Antibodies of the Invention

TABLE A

Sequences of the Heavy- and Light-Chain CDRs of the Exemplary Antibodies of the Invention

| ADI Name | VH CDR1 | VH CDR2 | VH CDR3 | VL CDR1 | VL CDR2 | VL CDR3 |
|---|---|---|---|---|---|---|
| Position by Kabat Numbering | H27-35 | H50-65 | H93-102 | L24-34 | L50-56 | L89-97 |
| ADI-26624 | GSISSYYWS (SEQ ID NO: 1) | YIYYSGSTNYNPSLKS (SEQ ID NO: 9) | ARGKSAFDP (SEQ ID NO: 17) | RASQGI SRWLA (SEQ ID NO: 23) | AASS LQS (SEQ ID NO: 25) | QQADL HPPLT (SEQ ID NO: 27) |
| ADI-29336 | GSISNYYWS (SEQ ID NO: 2) | TIYYSGSTRYNPSLKS (SEQ ID NO: 10) | ARGKSAFNP (SEQ ID NO: 18) | RASQGI SRWLA (SEQ ID NO: 23) | AASS LQS (SEQ ID NO: 25) | QQADL HPPLT (SEQ ID NO: 27) |
| ADI-29340 | GSIDYYWS (SEQ ID NO: 3) | YIYYSGSTGYNPSLKS (SEQ ID NO: 11) | ARGKSAFDP (SEQ ID NO: 17) | RASQGI SRWLA (SEQ ID NO: 23) | AASS LQS (SEQ ID NO: 25) | QQADL HPPLT (SEQ ID NO: 27) |
| ADI-26630 | GSISSYYWS (SEQ ID NO: 1) | YIYYSGSTNYNPSLKS (SEQ ID NO: 9) | ARGKTGSAA (SEQ ID NO: 19) | RASQGI SRWLA (SEQ ID NO: 23) | AASS LQS (SEQ ID NO: 25) | QQTVS FPIT (SEQ ID NO: 28) |
| ADI-29341 | GSIEYYWS (SEQ ID NO: 4) | YIYYSGSTNYNPSLKS (SEQ ID NO: 9) | ARGKTGSAA (SEQ ID NO: 19) | RASQGI SRWLA (SEQ ID NO: 23) | AASS LQS (SEQ ID NO: 25) | QQTVS FPIT (SEQ ID NO: 28) |
| ADI-29349 | GSIDHYYWS (SEQ ID NO: 5) | YIYYSGSTEYNPSLKS (SEQ ID NO: 12) | ARGKTGSAA (SEQ ID NO: 19) | RASQGI SRWLA (SEQ ID NO: 23) | AASS LQS (SEQ ID NO: 25) | QQTVS FPIT (SEQ ID NO: 28) |
|  | GSIX1X2YYWS (wherein X1 is selected from the group consisting of S, D or E; and X2 is selected from the group consisting of S, N, Y or H) (SEQ ID NO: 98) | X1IYYSGSTX2YNPSLKS, wherein X1 is selected from the group consisting of Y or T; and X2 is selected from the group consisting of N, R, G or E (SEQ ID NO: 100) | ARGKX1X2X3X4X5, wherein X1 is selected from the group consisting of S or T; X2 is selected from the group consisting of A or G; X3 is selected from the group consisting of F or S; X4 is selected from the group consisting of D, N or A; and X5 is selected from the group consisting of P or A (SEQ ID NO: 102) |  |  |  |
| ADI-26591 | FTFSSYAMS (SEQ ID NO: 6) | AISGSGGSTYYADSVKG (SEQ ID NO: 13) | AKTPIYYGFDL (SEQ ID NO: 20) | RASQGI SSWLA (SEQ ID NO: 24) | GASS LQS (SEQ ID NO: 26) | QQKNP FPPT (SEQ ID NO: 29) |
| ADI-29371 | FTFGNYAMS (SEQ ID NO: 7) | MISG-GGSTYYADSVKG (SEQ ID NO: 14) | AKTPIYYGFDL (SEQ ID NO: 20) | RASQGI SSWLA (SEQ ID NO: 24) | GASS LQS (SEQ ID NO: 26) | QQKNP FPPT (SEQ ID NO: 29) |
| ADI-30793 | FTFDSYAMT (SEQ ID NO: 8) | VISGSGGKTYYADSVKG (SEQ ID NO: 15) | AKTHLYYGFDL (SEQ ID NO: 21) | RASQGI SSWLA (SEQ ID NO: 24) | GASS LQS (SEQ ID NO: 26) | QQKNP FPPF (SEQ ID NO: 30) |
| ADI-30794 | FTFGNYAMS (SEQ ID NO: 7) | AISGSGGKTYYADSVKG (SEQ ID NO: 16) | AKTAIYYGFDL (SEQ ID NO: 22) | RASQGI SSWLA (SEQ ID NO: 24) | GASS LQS (SEQ ID NO: 26) | QQKNP FPPF (SEQ ID NO: 30) |

TABLE A-continued

Sequences of the Heavy- and Light-Chain CDRs of the Exemplary Antibodies of the Invention

| ADI Name | VH CDR1 | VH CDR2 | VH CDR3 | VL CDR1 | VL CDR2 | VL CDR3 |
|---|---|---|---|---|---|---|
| | FTFX1X2YAMX3 (in which X1 is selected from the group consisting of S, G or D; X2 is selected from the group consisting of S or N; and X3 is selected from the group consisting of S or T (SEQ ID NO: 99) | X1ISGX2GGX3TYYADSVKG, wherein X1 is selected from the group consisting of A, M or V; X2 is selected from the group consisting of S or deletion; and X3 is selected from the group consisting of S or K (SEQ ID NO: 101) | AKTX1X2YYGFDL, wherein X1 is selected from the group consisting of P, H or A; and X2 is selected from the group consisting of I or L (SEQ ID NO: 103) | | | |

TABLE B

Sequences of the Heavy and Light Chain Variable Regions of the Exemplary Antibodies of the Invention

| Name | VH DNA | VH protein | VL DNA | VL protein |
|---|---|---|---|---|
| ADI-26624 | CAGGTGCAGCTGCAGGAGTCGGGCCC AGGACTGGTGAAGCCTTCGGAGACCC TGTCCCTCACCTGCACTGTCTCTGGTG GCTCCATCAGTAGTTACTACTGGAGC TGGATCCGGCAGCCCCCAGGGAAGGG ACTGGAGTGGATTGGGTATATCTATT ACAGTGGGAGCACCAACTACAACCCC TCCCTCAAGAGTCGAGTCACCATATC AGTAGACACGTCCAAGAACCAGTTCT CCCTGAAGCTGAGTTCTGTGACCGCC GCAGACACGGCGGTGTACTACTGCGC CAGGGGTAAGAGTGCATTCGACCCAT GGGGACAGGGTACATTGGTCACCGTC TCCTCA(SEQ ID NO: 59) | QVQLQESGPGLVKP SETLSLTCTVSGGSIS SYYWSWIRQPPGKG LEWIGYIYYSGSTNY NPSLKSRVTISVDTS KNQFSLKLSSVTAA DTAVYYCARGKSAF DPWGQGTLVTVSS (SEQ ID NO: 44) | GACATCCAGATGACCCAGTCTCCATCT TCCGTGTCTGCATCTGTAGGAGACAGA GTCACCATCACTTGTCGGGCGAGTCAG GGTATTAGCAGGTGGTTAGCCTGGTAT CAGCAGAAACCAGGGAAAGCCCCTAA GCTCCTGATCTATGCTGCATCCAGTTTG CAAAGTGGGGTCCCATCAAGGTTCAGC GGCAGTGGATCTGGGACAGATTTCACT CTCACCATCAGCAGCCTGCAGCCTGAA GATTTTGCAACTTATTACTGTCAGCAG GCAGACCTCCACCCTCCTCTCACTTTTG GCGGAGGGACCAAGGTTGAGATCAAA (SEQ ID NO: 69) | DIQMTQSPSSVSAS VGDRVTITCRASQG ISRWLAWYQQKPG KAPKLLIYAASSLQ SGVPSRFSGSGSGT DFTLTISSLQPEDFA TYYCQQADLHPPL TFGGGTKVEIK (SEQ ID NO: 54) |
| ADI-29336 | CAGGTGCAGCTGCAGGAGTCGGGCCC AGGACTGGTGAAGCCTTCGGAGACCC TGTCCCTCACCTGCACTGTCTCTGGTG GCTCCATCAGTAATTACTACTGGAGCT GGATCCGGCAGCCCCCAGGGAAGGGA CTGGAGTGGATTGGGACGATCTATTA CAGTGGGAGCACCCGTTACAACCCCT CCCTCAAGAGTCGAGTCACCATATCA GTAGACACGTCCAAGAACCAGTTCTC CCTGAAGCTGAGTTCTGTGACCGCCGC AGACACGGCGGTGTACTACTGCGCCA GGGGTAAGAGTGCATTCAACCCATGG GGACAGGGTACATTGGTCACCGTCTC CTCA(SEQ ID NO: 60) | QVQLQESGPGLVKPS ETLSLTCTVSGGSISN YYWSWIRQPPGKGL EWIGTIYYSGSTRYN PSLKSRVTISVDTSK NQFSLKLSSVTAADT AVYYCARGKSAFNP WGQGTLVTVSS (SEQ ID NO: 45) | GACATCCAGATGACCCAGTCTCCATCT TCCGTGTCTGCATCTGTAGGAGACAGA GTCACCATCACTTGTCGGGCGAGTCAG GGTATTAGCAGGTGGTTAGCCTGGTAT CAGCAGAAACCAGGGAAAGCCCCTAA GCTCCTGATCTATGCTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGGCAGACCTCCACCCTCCTCTCACT TTTGGCGGAGGGACCAAGGTTGAGAT CAAA(SEQ ID NO: 69) | DIQMTQSPSSVSAS VGDRVTITCRASQG ISRWLAWYQQKPG KAPKLLIYAASSLQ SGVPSRFSGSGSGT DFTLTISSLQPEDFA TYYCQQADLHPPL TFGGGTKVEIK (SEQ ID NO: 54) |
| ADI-29340 | CAGGTGCAGCTGCAGGAGTCGGGCCC AGGACTGGTGAAGCCTTCGGAGACCC TGTCCCTCACCTGCACTGTCTCTGGTG GCTCCATCGATTATTACTACTGGAGCT GGATCCGGCAGCCCCCAGGGAAGGGA CTGGAGTGGATTGGGTATATCTATTAC TCGGGGAGCACCGGTTACAACCCCTC CCTCAAGAGTCGAGTCACCATATCAG TAGACACGTCCAAGAACCAGTTCTCC CTGAAGCTGAGTTCTGTGACCGCCGC AGACACGGCGGTGTACTACTGCGCCA GGGGTAAGAGTGCATTCGACCCATGG GGACAGGGTACATTGGTCACCGTCTC CTCA(SEQ ID NO: 61) | QVQLQESGPGLVKPS ETLSLTCTVSGGSID YYYWSWIRQPPGKG LEWIGYIYYSGSTGY NPSLKSRVTISVDTS KNQFSLKLSSVTAAD TAVYYCARGKSAFD PWGQGTLVTVSS (SEQ ID NO: 46) | GACATCCAGATGACCCAGTCTCCATCT TCCGTGTCTGCATCTGTAGGAGACAGA GTCACCATCACTTGTCGGGCGAGTCAG GGTATTAGCAGGTGGTTAGCCTGGTAT CAGCAGAAACCAGGGAAAGCCCCTAA GCTCCTGATCTATGCTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGGCAGACCTCCACCCTCCTCTCACT TTTGGCGGAGGGACCAAGGTTGAGAT CAAA(SEQ ID NO: 69) | DIQMTQSPSSVSAS VGDRVTITCRASQG ISRWLAWYQQKPG KAPKLLIYAASSLQ SGVPSRFSGSGSGT DFTLTISSLQPEDFA TYYCQQADLHPPL TFGGGTKVEIK (SEQ ID NO: 54) |
| ADI-26630 | CAGGTGCAGCTGCAGGAGTCGGGCCC AGGACTGGTGAAGCCTTCGGAGACCC TGTCCCTCACCTGCACTGTCTCTGGTG GCTCCATCAGTAGTTACTACTGGAGCT GGATCCGGCAGCCCCCAGGGAAGGGA CTGGAGTGGATTGGGTATATCTATTAC AGTGGGAGCACCAACTACAACCCCTC | QVQLQESGPGLVKP SETLSLTCTVSGGSIS SYYWSWIRQPPGKG LEWIGYIYYSGSTNY NPSLKSRVTISVDTS KNQFSLKLSSVTAA DTAVYYCARGKTGS | GACATCCAGATGACCCAGTCTCCATCT TCCGTGTCTGCATCTGTAGGAGACAGA GTCACCATCACTTGTCGGGCGAGTCAG GGTATTAGCAGGTGGTTAGCCTGGTAT CAGCAGAAACCAGGGAAAGCCCCTAA GCTCCTGATCTATGCTGCATCCAGTTT GCAAAGTGGGGTCCCATCAAGGTTCA | DIQMTQSPSSVSAS VGDRVTITCRASQG ISRWLAWYQQKPG KAPKLLIYAASSLQ SGVPSRFSGSGSGT DFTLTISSLQPEDFA TYYCQQTVSFPITF |

TABLE B-continued

Sequences of the Heavy and Light Chain Variable Regions of the Exemplary Antibodies of the Invention

| Name | VH DNA | VH protein | VL DNA | VL protein |
|---|---|---|---|---|
| | CCTCAAGAGTCGAGTCACCATATCAG TAGACACGTCCAAGAACCAGTTCTCC CTGAAGCTGAGTTCTGTGACCGCCGC AGACACGGCGGTGTACTACTGCGCCA GGGGTAAGACGGGATCTGCCGCATGG GGACAGGGTACATTGGTCACCGTCTC CTCA(SEQ ID NO: 62) | AAWGQGTLVTVSS (SEQ ID NO: 47) | GCGGCAGTGGATCTGGGACAGATTTC ACTCTCACCATCAGCAGCCTGCAGCCT GAAGATTTTGCAACTTATTACTGTCAG CAGACAGTCCTTCCCTATCACTTTT GGCGGAGGGACCAAGGTTGAGATCAA A(SEQ ID NO: 70) | GGGTKVEIK (SEQ ID NO: 55) |
| ADI-29341 | CAGGTGCAGCTGCAGGAGTCGGGCCC AGGACTGGTGAAGCCTTCGGAGACCC TGTCCCTCACCTGCACTGTCTCTGGTG GCTCCATCGAGCATTACTACTGGAGCT GGATCCGGCAGCCCCCAGGGAAGGGA CTGGAGTGGATTGGGTATATCTATTAC AGTGGGAGCACCAACTACAACCCCTC CCTCAAGAGTCGAGTCACCATATCAG TAGACACGTCCAAGAACCAGTTCTCC CTGAAGCTGAGTTCTGTGACCGCCGC AGACACGGCGGTGTACTACTGCGCCA GGGGTAAGACGGGATCTGCCGCATGG GGACAGGGTACATTGGTCACCGTCTC CTCA(SEQ ID NO: 63) | QVQLQESGPGLVKPS ETLSLTCTVSGGSIEH YYWSWIRQPPGKGL EWIGYIYYSGSTNYN PSLKSRVTISVDTSK NQFSLKLSSVTAADT AVYYCARGKTGSAA WGQGTLVTVSS (SEQ ID NO: 48) | GACATCCAGATGACCCAGTCTCCATCT TCCGTGTCTGCATCTGTAGGAGACAGA GTCACCATCACTTGTCGGGCGAGTCAG ATCAGCAGATGGTTAGCCTGGTAT CAGCAGAAACCAGGGAAAGCCCCTAA GCTCCTGATCTATGCTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTACTATTGTCAG CAGACAGTCTCCTTCCCTATCACTTTC GGCGGAGGGACCAAGGTGGAGATCAA A(SEQ ID NO: 71) | DIQMTQSPSSVSAS VGDRVTITCRASQG ISRWLAWYQQKPG KAPKLLIYAASSLQ SGVPSRFSGSGSGT DFTLTISSLQPEDFA TYYCQQTVSFPITF GGGTKVEIK (SEQ ID NO: 55) |
| ADI-29349 | CAGGTGCAGCTGCAGGAGTCGGGCCC AGGACTGGTGAAGCCTTCGGAGACCC TGTCCCTCACCTGCACTGTCTCTGGTG GCTCCATCGATCATTACTACTGGAGTT GGATCCGGCAGCCCCCAGGGAAGGGA CTGGAGTGGATTGGGTATATCTATTAC TCTGGGAGCACCGAGTACAACCCCTC CCTCAAGAGTCGAGTCACCATATCAG TAGACACGTCCAAGAACCAGTTCTCC CTGAAGCTGAGTTCTGTGACCGCCGC AGACACGGCGGTGTACTACTGCGCCA GGGGTAAGACGGGATCTGCCGCATGG GGACAGGGTACATTGGTCACCGTCTC CTCA(SEQ ID NO: 64) | QVQLQESGPGLVKPS ETLSLTCTVSGGSID HYYWSWIRQPPGKG LEWIGYIYYSGSTEY NPSLKSRVTISVDTS KNQFSLKLSSVTAAD TAVYYCARGKTGSA AWGQGTLVTVSS (SEQ ID NO: 49) | GACATCCAGATGACCCAGTCTCCATCT TCCGTGTCTGCATCTGTAGGAGACAGA GTCACCATCACTTGTCGGGCGAGTCAG ATCAGCAGATGGTTAGCCTGGTAT CAGCAGAAACCAGGGAAAGCCCCTAA GCTCCTGATCTATGCTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGACAGTCTCCTTCCCTATCACTTTT GGCGGAGGGACCAAGGTTGAGATCAA A(SEQ ID NO: 70) | DIQMTQSPSSVSAS VGDRVTITCRASQG ISRWLAWYQQKPG KAPKLLIYAASSLQ SGVPSRFSGSGSGT DFTLTISSLQPEDFA TYYCQQTVSFPITF GGGTKVEIK (SEQ ID NO: 55) |
| ADI-26591 | GAGGTGCAGCTGTTGGAGTCTGGGGG AGGCTTGGTACAGCCTGGGGGGTCCC TGAGACTCTCCTGTGCAGCCTCTGGAT TCACCTTTAGCAGCTATGCCATGAGCT GGGTCCGCCAGGCTCCAGGGAAGGGG CTGGAGTGGGTCTCAGCTATTAGTGGT AGTGGTGGTAGCACATATACGCAGACT CCCGTGAAGGGCCGGTTCACCATCTC CAGAGACAATTCCAAGAACACGCTGT ATCTGCAAATGAACAGCCTGAGAGCC GAGGACACGGCGGTGTACTACTGCGC CAAGACGCCTATATACTACGGCTTCG ACCTATGGGGGAGAGGTACCTTGGTC ACCGTCTCCTCA (SEQ ID NO: 65) | EVQLLESGGGLVQP GGSLRLSCAASGFTF SSYAMSWVRQAPGK GLEWVSAISGSGGST YYADSVKGRFTISRD NSKNTLYLQMNSLR AEDTAVYYCAKTPIY YGFDLWGRGTLVTV SS (SEQ ID NO: 50) | GACATCCAGTTGACCCAGTCTCCATCT TCCGTGTCTGCATCTGTAGGAGACAGA GTCACCATCACTTGTCGGGCGAGTCAG ATCAGCAGCTGGTTAGCCTGGTAT CAGCAGAAACCAGGGAAAGCCCCTAA GCTCCTGATCTATGGTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGAAAAATCCCTTCCCTCCTACTTTT GGCGGAGGGACCAAGGTTGAGATCAA A(SEQ ID NO: 72) | DIQLTQSPSSVSAS VGDRVTITCRASQG ISSWLAWYQQKPG KAPKLLIYGASSLQ SGVPSRFSGSGSGT DFTLTISSLQPEDFA TYYCQQKNPFPPTF GGGTKVEIK (SEQ ID NO: 57) |
| ADI-29371 | GAGGTGCAGCTGTTGGAGTCTGGGGG AGGCTTGGTACAGCCTGGGGGGTCCC TGAGACTCTCCTGTGCAGCCTCTGGAT TCACCTTTGGGAATTATGCCATGAGCT GGGTCCGCCAGGCTCCAGGGAAGGGG CTGGAGTGGGTCTCAATGATTAGTGG GGGTGGTAGCACATACACGCAGACT CCGTGAAGGGCCGGTTCACCATCTCC AGAGACAATTCCAAGAACACGCTGTA TCTGCAAATGAACAGCCTGAGAGCCG AGGACACGGCGGTGTACTACTGCGCC AAGACGCCTATATACTACGGCTTCGA CCTATGGGGGAGAGGTACCTTGGTCA CCGTCTCCTCA (SEQ ID NO: 66) | EVQLLESGGGLVQP GGSLRLSCAASGFTF GNYAMSWVRQAPG KGLEWVSMISGGGS TYYADSVKGRFTISR DNSKNTLYLQMNSL RAEDTAVYYCAKTPI YYGFDLWGRGTLVT VSS (SEQ ID NO: 51) | GACATCCAGTTGACCCAGTCTCCATCT TCCGTGTCTGCATCTGTAGGAGACAGA GTCACCATCACTTGTCGGGCGAGTCAG ATCAGCAGCTGGTTAGCCTGGTAT CAGCAGAAACCAGGGAAAGCCCCTAA GCTCCTGATCTATGGTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGAAAAATCCCTTCCCTCCTACTTTT GGCGGAGGGACCAAGGTTGAGATCAA A(SEQ ID NO: 72) | DIQLTQSPSSVSAS VGDRVTITCRASQG ISSWLAWYQQKPG KAPKLLIYGASSLQ SGVPSRFSGSGSGT DFTLTISSLQPEDFA TYYCQQKNPFPPTF GGGTKVEIK (SEQ ID NO: 57) |
| ADI-30793 | GAGGTGCAGCTGTTGGAGTCTGGGGG AGGCTTGGTACAGCCTGGGGGGTCCC TGAGACTCTCCTGTGCAGCCTCTGGAT TCACCTTTGATAGCTATGCCATGACTT GGGTCCGCCAGGCTCCAGGGAAGGGG | EVQLLESGGGLVQP GGSLRLSCAASGFTF DSYAMTWVRQAPG KGLEWVSVISGSGG KTYYADSVKGRFTIS | GACATCCAGTTGACCCAGTCTCCATCT TCCGTGTCTGCATCTGTAGGAGACAGA GTCACCATCACTTGTCGGGCGAGTCAG ATCAGCAGCTGGTTAGCCTGGTAT CAGCAGAAACCAGGGAAAGCCCCTAA | DIQLTQSPSSVSAS VGDRVTITCRASQG ISSWLAWYQQKPG KAPKLLIYGASSLQ SGVPSRFSGSGSGT |

TABLE B-continued

Sequences of the Heavy and Light Chain Variable Regions of the Exemplary Antibodies of the Invention

| Name | VH DNA | VH protein | VL DNA | VL protein |
|---|---|---|---|---|
| | CTGGAGTGGGTCTCAGTTATTAGTGGA AGTGGTGGTAAGACATACTACGCAGA CTCCGTGAAGGGCCGGTTCACCATCTC CAGAGACAACTCCAAGAACACGCTGT ATCTGCAAATGAACAGCCTGAGAGCC GAGGACACGGCGGTGTACTACTGCGC CAAGACGCATCTTTACTACGGCTTCGA CCTATGGGGAGAGGTACCTTGGTCA CCGTCTCCTCA (SEQ ID NO: 67) | RDNSKNTLYLQMNS LRAEDTAVYYCAKT HLYYGFDLWGRGTL VTVSS (SEQ ID NO: 52) | GCTCCTGATCTATGGTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGAAAAATCCCTTCCCTCCTTTTTTT GGCGGAGGGACCAAGGTTGAGATCAA A (SEQ ID NO: 73) | DFTLTISSLQPEDFA TYYCQQKNPFPPFF GGGTKVEIK (SEQ ID NO: 58) |
| ADI-30794 | GAGGTGCAGCTGTTGGAGTCTGGGGG AGGCTTGGTACAGCCTGGGGGGTCCC TGAGACTCTCCTGTGCAGCCTCTGGAT TCACCTTTGGGAATTATGCCATGAGCT GGGTCCGCCAGGCTCCAGGGAAGGGG CTGGAGTGGGTCTCAGCTATTAGTGG AAGTGGTGGTAAGACATACTACGCAG ACTCCGTGAAGGGCCGGTTCACCATC TCCAGAGACAATTCCAAGAACACGCTG TATCTGCAAATGAACAGCCTGAGAGC CGAGGACACGGCGGTGTACTACTGCG CCAAGACGGCTATATACTACGGCTTC GACCTATGGGGGAGAGGTACCTTGGT CACCGTCTCCTCA (SEQ ID NO: 68) | EVQLLESGGGLVQP GGSLRLSCAASGFTF GNYAMSWVRQAPG KGLEWVSAISGSGG KTYYADSVKGRFTIS RDNSKNTLYLQMNS LRAEDTAVYYCAKT AIYYGFDLWGRGTL VTVSS (SEQ ID NO: 53) | GACATCCAGTTGACCCAGTCTCCATCT TCCGTGTCTGCATCTGTAGGAGACAGA GTCACCATCACTTGTCGGGCGAGTCAG GGTATTAGCAGCTGGTTAGCCTGGTAT CAGCAGAAACCAGGGAAAGCCCCTAA GCTCCTGATCTATGGTGCATCCAGTTT GCAAAGTGGGGTCCCATCAAGGTTCA GCGGCAGTGGATCTGGGACAGATTTC ACTCTCACCATCAGCAGCCTGCAGCCT GAAGATTTTGCAACTTATTACTGTCAG CAGAAAAATCCCTTCCCTCCTTTTTTT GGCGGAGGGACCAAGGTTGAGATCAA A (SEQ ID NO: 73) | DIQLTQSPSSVSAS VGDRVTITCRASQG ISSWLAWYQQKPG KAPKLLIYGASSLQ SGVPSRFSGSGSGT DFTLTISSLQPEDFA TYYCQQKNPFPPFF GGGTKVEIK (SEQ ID NO: 58) |

TABLE C

Sequences of the Heavy and Light Chain FRs of the Exemplary Antibodies of the Invention

| ADI Name | VH FR1 | VH FR2 | VH FR3 | VH FR4 | VL FR1 | VL FR2 | VL FR3 | VL FR4 |
|---|---|---|---|---|---|---|---|---|
| ADI-26624, ADI-29336, ADI-29340, ADI-26630, ADI-29341, ADI-29349 | QVQL PGLV KPSE TLSL TCTV SG (SEQ ID NO: 31) | WIRQ QESG PPGK GLEW IG (SEQ ID NO: 35) | RVTI SVDT SKNQ FSLK (SEQ ID NO: 39) LSSV TAAD ITC TAVY YC | WGQG TLVT VSS (SEQ ID NO: 37) | DIQM TQSP SSVS ASVG DRVT ITC (SEQ ID NO: 41) | WYQQ KPGK APKL LIY (SEQ ID NO: 42) | GVPS RFSG SGSG TDFT LTIS SLQP EDFA TYYC (SEQ ID NO: 43) | FGGG TKVE IK (SEQ ID NO: 59) |
| ADI-26591, ADI-29371, ADI-30793, ADI-30794 | EVQL LESG GGLV QPGG SLRL SCAA SG (SEQ ID NO: 32) | WVRQ APGK GLEW VS (SEQ ID NO: 36) | RFTI SRDN SKNT TAVY YC (SEQ ID NO: 38) RAED | WGRG TLVT VSS (SEQ ID NO: 40) | DIQL TQSP SSVS ASVG DRVT ITC (SEQ ID NO: 41) | WYQQ KPGK APKL LIY (SEQ ID NO: 42) | GVPS RFSG SGSG TDFT LTIS SLQP EDFA TYYC (SEQ ID NO: 43) | FGGG TKVE IK (SEQ ID NO: 59) |

TABLE D

Numbering of a part of the sequences in the present sequence listing.

| ADI Name | SEQ ID NO for the heavy chain Heavy chain variable region VH | | | | | | | | | SEQ ID NO for the light chain Light chain variable region | | | | | | | | | IgG4 | | IgG1 | |
|---|---|---|---|---|---|---|---|---|---|---|---|---|---|---|---|---|---|---|---|---|---|---|
| | VH FR1 | VH CDR1 | VH FR2 | VH CDR2 | VH FR3 | VH CDR3 | VH FR4 | VH DNA | V H Pro. | VL FR1 | VL CDR1 | VL FR2 | VL CDR2 | VL FR3 | VL CDR3 | VL FR4 | V L DNA | V L Pro. | Heavy Chain HC | Light Chain LC | Heavy Chain HC | Light Chain LC |
| ADI-26624 | 31 | 1 | 33 | 9 | 35 | 17 | 37 | 59 | 44 | 39 | 23 | 41 | 25 | 42 | 27 | 43 | 69 | 54 | 74 | 75 | 88 | 75 |
| ADI-29336 | 31 | 2 | 33 | 10 | 35 | 18 | 37 | 60 | 45 | 39 | 23 | 41 | 25 | 42 | 27 | 43 | 69 | 54 | 76 | 75 | 89 | 75 |
| ADI-29340 | 31 | 3 | 33 | 11 | 35 | 17 | 37 | 61 | 46 | 39 | 23 | 41 | 25 | 42 | 27 | 43 | 69 | 54 | 77 | 75 | 90 | 75 |
| ADI-26630 | 31 | 1 | 33 | 9 | 35 | 19 | 37 | 62 | 47 | 39 | 23 | 41 | 25 | 42 | 28 | 43 | 70 | 55 | 78 | 79 | 91 | 79 |

TABLE D-continued

Numbering of a part of the sequences in the present sequence listing.

| ADI Name | SEQ ID NO for the heavy chain Heavy chain variable region VH | | | | | | | | | SEQ ID NO for the light chain Light chain variable region | | | | | | | | | IgG4 | | IgG1 | |
|---|---|---|---|---|---|---|---|---|---|---|---|---|---|---|---|---|---|---|---|---|---|---|
| | V H F R1 | V H CD R1 | V H F R2 | V H CD R2 | V H F R3 | V H CD R3 | V H F R4 | V H DN A | V H Pro. | V L F R1 | V L CD R1 | V L F R2 | V L CD R2 | V L F R3 | V L CD R3 | V L F R4 | V L DN A | V L Pro. | Heavy Chain HC | Light Chain LC | Heavy Chain HC | Light Chain LC |
| ADI-29341 | 31 | 4 | 33 | 9 | 35 | 19 | 37 | 63 | 48 | 39 | 23 | 41 | 25 | 42 | 28 | 43 | 71 | 55 | 80 | 79 | 92 | 79 |
| ADI-29349 | 31 | 5 | 33 | 12 | 35 | 19 | 37 | 64 | 49 | 39 | 23 | 41 | 25 | 42 | 28 | 43 | 70 | 55 | 81 | 79 | 93 | 79 |
| ADI-26591 | 32 | 6 | 34 | 13 | 36 | 20 | 38 | 65 | 50 | 40 | 24 | 41 | 26 | 42 | 29 | 43 | 72 | 57 | 82 | 83 | 94 | 83 |
| ADI-29371 | 32 | 7 | 34 | 14 | 36 | 20 | 38 | 66 | 51 | 40 | 24 | 41 | 26 | 42 | 29 | 43 | 72 | 57 | 84 | 83 | 95 | 83 |
| ADI-30793 | 32 | 8 | 34 | 15 | 36 | 21 | 38 | 67 | 52 | 40 | 24 | 41 | 26 | 42 | 30 | 43 | 73 | 58 | 85 | 86 | 96 | 86 |
| ADI-30794 | 32 | 7 | 34 | 16 | 36 | 22 | 38 | 68 | 53 | 40 | 24 | 41 | 26 | 42 | 30 | 43 | 73 | 58 | 87 | 86 | 97 | 86 |

Fully-length Amino Acid Sequences of the Heavy and Light Chains of the Antibodies of the Invention

```
ADI26624-IgG4
Amino acid sequence of the HC
                                                    (SEQ ID NO: 74)
QVQLQESGPGLVKPSETLSLTCTVSGGSISSYYWSWIRQPPGKGLEWIGYIYYSGSTNYNPS

LKSRVTISVDTSKNQFSLKLSSVTAADTAVYYCARGKSAFDPWGQGTLVTVSSASTKGPSVF

PLAPCSRSTSESTAALGCLVKDYFPEPVTVSWNSGALTSGVHTFPAVLQSSGLYSLSSVVTVP

SSSLGTKTYTCNVDHKPSNTKVDKRVESKYGPPCPPCPAPEAAGGPSVFLFPPKPKDTLMIS

RTPEVTCVVVDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCSVMHEALHNH

YTQKSLSLSLG

Amino acid sequence of the LC
                                                    (SEQ ID NO: 75)
DIQMTQSPSSVSASVGDRVTITCRASQGISRWLAWYQQKPGKAPKLLIYAASSLQSGVPSRF

SGSGSGTDFTLTISSLQPEDFATYYCQQADLHPPLTFGGGTKVEIKRTVAAPSVFIFPPSDEQL

KSGTASVVCLLNNFYPREAKVQWKVDNALQSGNSQESVTEQDSKDSTYSLSSTLTLSKAD

YEKHKVYACEVTHQGLSSPVTKSFNRGEC

ADI29336-IgG4
Amino acid sequence of the HC
                                                    (SEQ ID NO: 76)
QVQLQESGPGLVKPSETLSLTCTVSGGSISNYYWSWIRQPPGKGLEWIGTIYYSGSTRYNPS

LKSRVTISVDTSKNQFSLKLSSVTAADTAVYYCARGKSAFNPWGQGTLVTVSSASTKGPSV

FPLAPCSRSTSESTAALGCLVKDYFPEPVTVSWNSGALTSGVHTFPAVLQSSGLYSLSSVVT

VPSSSLGTKTYTCNVDHKPSNTKVDKRVESKYGPPCPPCPAPEAAGGPSVFLFPPKPKDTL

MISRTPEVTCVVVDVSQEDPEVQFNWYVDGVEVHNAKTKPREEQFNSTYRVVSVLTVLH

QDWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEAL

HNHYTQKSLSLSLG

Amino acid sequence of the LC
```

-continued

ADI29340-IgG4
Amino acid sequence of the HC (SEQ ID NO: 75)

(SEQ ID NO: 77)
QVQLQESGPGLVKPSETLSLTCTVSGGSIDYYWSWIRQPPGKGLEWIGYIYYSGSTGYNPS

LKSRVTISVDTSKNQFSLKLSSVTAADTAVYYCARGKSAFDPWGQGTLVTVSSASTKGPSVF

PLAPCSRSTSESTAALGCLVKDYFPEPVTVSWNSGALTSGVHTFPAVLQSSGLYSLSSVVTVP

SSSLGTKTYTCNVDHKPSNTKVDKRVESKYGPPCPPCPAPEAAGGPSVFLFPPKPKDTLMIS

RTPEVTCVVVDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCSVMHEALHNH

YTQKSLSLSLG

Amino acid sequence of the LC (SEQ ID NO: 75)

ADI26630-IgG4
Amino acid sequence of the HC (SEQ ID NO: 78)
QVQLQESGPGLVKPSETLSLTCTVSGGSISSYYWSWIRQPPGKGLEWIGYIYYSGSTNYNPS

LKSRVTISVDTSKNQFSLKLSSVTAADTAVYYCARGKTGSAAWGQGTLVTVSSASTKGPSV

FPLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEAAGGPSVFLFPPKPKDTLMI

SRTPEVTCVVVDVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVFSCSVMHEALHN

HYTQKSLSLSLG

Amino acid sequence of the LC (SEQ ID NO: 79)
DIQMTQSPSSVSASVGDRVTITCRASQGISRWLAWYQQKPGKAPKLLIYAASSLQSGVPSRF

SGSGSGTDFTLTISSLQPEDFATYYCQQTVSFPITFGGGTKVEIKRTVAAPSVFIFPPSDEQLKS

GTASVVCLLNNFYPREAKVQWKVDNALQSGNSQESVTEQDSKDSTYSLSSTLTLSKADYE

KHKVYACEVTHQGLSSPVTKSFNRGEC

ADI29341-IgG4
Amino acid sequence of the HC (SEQ ID NO: 80)
QVQLQESGPGLVKPSETLSLTCTVSGGSIEHYYWSWIRQPPGKGLEWIGYIYYSGSTNYNPS

LKSRVTISVDTSKNQFSLKLSSVTAADTAVYYCARGKTGSAAWGQGTLVTVSSASTKGPSV

FPLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEAAGGPSVFLFPPKPKDTLMI

SRTPEVTCVVVDVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVFSCSVMHEALHN

HYTQKSLSLSLG

Amino acid sequence of the LC (SEQ ID NO: 79)

ADI 29349-IgG4
Amino acid sequence of the HC (SEQ ID NO: 81)
QVQLQESGPGLVKPSETLSLTCTVSGGSIDHYYWSWIRQPPGKGLEWIGYIYYSGSTEYNPS

LKSRVTISVDTSKNQFSLKLSSVTAADTAVYYCARGKTGSAAWGQGTLVTVSSASTKGPSV

FPLAPCSRSTSESTAALGCLVKDYFPEPVTVSWNSGALTSGVHTFPAVLQSSGLYSLSSVVTV

```
PSSSLGTKTYTCNVDHKPSNTKVDKRVESKYGPPCPPCPAPEAAGGPSVFLFPPKPKDTLMI

SRTPEVTCVVVDVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVFSCSVMHEALHN

HYTQKSLSLSLG

Amino acid sequence of the LC
                                                    (SEQ ID NO: 79)
ADI 26591-IgG4
Amino acid sequence of the HC
                                                    (SEQ ID NO: 82)
EVQLLESGGGLVQPGGSLRLSCAASGFTFSSYAMSWVRQAPGKGLEWVSAISGSGGSTYYA

DSVKGRFTISRDNSKNTLYLQMNSLRAEDTAVYYCAKTPIYYGFDLWGRGTLVTVSSASTK

GPSVFPLAPCSRSTSESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEGNVFSCSVMHEA

LHNHYTQKSLSLSLG

Amino acid sequence of the LC
                                                    (SEQ ID NO: 83)
DIQLTQSPSSVSASVGDRVTITCRASQGISSWLAWYQQKPGKAPKLLIYGASSLQSGVPSRFS

GSGSGTDFTLTISSLQPEDFATYYCQQKNPFPPTFGGGTKVEIKRTVAAPSVFIFPPSDEQLKS

GTASVVCLLNNFYPREAKVQWKVDNALQSGNSQESVTEQDSKDSTYSLSSTLTLSKADYE

KHKVYACEVTHQGLSSPVTKSFNRGEC

ADI 29371-IgG4
Amino acid sequence of the HC
                                                    (SEQ ID NO: 84)
EVQLLESGGGLVQPGGSLRLSCAASGFTFGNYAMSWVRQAPGKGLEWVSMISGGGSTYYA

DSVKGRFTISRDNSKNTLYLQMNSLRAEDTAVYYCAKTPIYYGFDLWGRGTLVTVSSASTK

GPSVFPLAPCSRSTSESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEAAGGPSVFLFPPKPKD

TLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEGNVFSCSVMHEA

LHNHYTQKSLSLSLG

Amino acid sequence of the LC
                                                    (SEQ ID NO: 83)
ADI 30793-IgG4
Amino acid sequence of the HC
                                                    (SEQ ID NO: 85)
EVQLLESGGGLVQPGGSLRLSCAASGFTFDSYAMTWVRQAPGKGLEWVSVISGSGGKTYY

ADSVKGRFTISRDNSKNTLYLQMNSLRAEDTAVYYCAKTHLYYGFDLWGRGTLVTVSSAS

TKGPSVFPLAPCSRSTSESTAALGCLVKDYFPEPVTVSWNSGALTSGVHTFPAVLQSSGLYSL

SSVVTVPSSSLGTKTYTCNVDHKPSNTKVDKRVESKYGPPCPPCPAPEAAGGPSVFLFPPKP

KDTLMISRTPEVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQEGNVFSCSVMH

EALHNHYTQKSLSLSLG
```

Amino acid sequence of the LC
                                                                (SEQ ID NO: 86)
DIQLTQSPSSVSASVGDRVTITCRASQGISSWLAWYQQKPGKAPKLLIYGASSLQSGVPSRF

SGSGSGTDFTLTISSLQPEDFATYYCQQKNPFPPPFFGGGTKVEIKRTVAAPSVFIFPPSDEQLK

SGTASVVCLLNNFYPREAKVQWKVDNALQSGNSQESVTEQDSKDSTYSLSSTLTLSKADY

EKHKVYACEVTHQGLSSPVTKSFNRGEC

ADI 30794-IgG4
Amino acid sequence of the HC
                                                                (SEQ ID NO: 87)
EVQLLESGGGLVQPGGSLRLSCAASGFTFGNYAMSWVRQAPGKGLEWVSAISGSGGKTY

YADSVKGRFTISRDNSKNTLYLQMNSLRAEDTAVYYCAKTAIYYGFDLWGRGTLVTVSSA

STKGPSVFPLAPCSRSTSESTAALGCLVKDYFPEPVTVSWNSGALTSGVHTFPAVLQSSGLYS

LSSVVTVPSSSLGTKTYTCNVDHKPSNTKVDKRVESKYGPPCPPCPAPEAAGGPSVFLFPPK

PKDTLMISRTPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEEMTKNQVSLTC

LVKGFYPSDIAVEWESNGQPENNYKTTPPVLDSDGSFFLYSRLTVDKSRWQEGNVFSCSVM

HEALHNHYTQKSLSLSLG

Amino acid sequence of the LC
                                                                (SEQ ID NO: 86)
ADI26624-IgG1
Amino acid sequence of the HC
                                                                (SEQ ID NO: 88)
QVQLQESGPGLVKPSETLSLTCTVSGGSISSYYWSWIRQPPGKGLEWIGYIYYSGSTNYNPS

LKSRVTISVDTSKNQFSLKLSSVTAADTAVYYCARGKSAFDPWGQGTLVTVSSASTKGPSVF

PLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

Amino acid sequence of the LC
                                                                (SEQ ID NO: 75)
ADI29336-IgG1
Amino acid sequence of the HC
                                                                (SEQ ID NO: 89)
QVQLQESGPGLVKPSETLSLTCTVSGGSISNYYWSWIRQPPGKGLEWIGTIYYSGSTRYNPS

LKSRVTISVDTSKNQFSLKLSSVTAADTAVYYCARGKSAFNPWGQGTLVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

Amino acid sequence of the LC
                                                                (SEQ ID NO: 75)
ADI29340-IgG1
Amino acid sequence of the HC
                                                                (SEQ ID NO: 90)
QVQLQESGPGLVKPSETLSLTCTVSGGSIDYYYWSWIRQPPGKGLEWIGYIYYSGSTGYNPS

LKSRVTISVDTSKNQFSLKLSSVTAADTAVYYCARGKSAFDPWGQGTLVTVSSASTKGPSVF

PLAPSSKSTSGGTAALGCLVKDYFPEPVTVSWNSGALTSGVHTFPAVLQSSGLYSLSSVVTV

-continued

PSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

Amino acid sequence of the LC
(SEQ ID NO: 75)

ADI26630-IgG1
Amino acid sequence of the HC
(SEQ ID NO: 91)
QVQLQESGPGLVKPSETLSLTCTVSGGSISSYYWSWIRQPPGKGLEWIGYIYYSGSTNYNPS

LKSRVTISVDTSKNQFSLKLSSVTAADTAVYYCARGKTGSAAWGQGTLVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

Amino acid sequence of the LC
(SEQ ID NO: 79)

ADI29341-IgG1
Amino acid sequence of the HC
(SEQ ID NO: 92)
QVQLQESGPGLVKPSETLSLTCTVSGGSIEHYYWSWIRQPPGKGLEWIGYIYYSGSTNYNPS

LKSRVTISVDTSKNQFSLKLSSVTAADTAVYYCARGKTGSAAWGQGTLVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

Amino acid sequence of the LC
(SEQ ID NO: 79)

ADI 29349-IgG1
Amino acid sequence of the HC
(SEQ ID NO: 93)
QVQLQESGPGLVKPSETLSLTCTVSGGSIDHYYWSWIRQPPGKGLEWIGYIYYSGSTEYNPS

LKSRVTISVDTSKNQFSLKLSSVTAADTAVYYCARGKTGSAAWGQGTLVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

Amino acid sequence of the LC
(SEQ ID NO: 79)

-continued

ADI 26591-IgG1
Amino acid sequence of the HC
(SEQ ID NO: 94)
EVQLLESGGGLVQPGGSLRLSCAASGFTFSSYAMSWVRQAPGKGLEWVSAISGSGGSTYYA

DSVKGRFTISRDNSKNTLYLQMNSLRAEDTAVYYCAKTPIYYGFDLWGRGTLVTVSSASTK

GPSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HEALHNHYTQKSLSLSPG

Amino acid sequence of the LC
(SEQ ID NO: 83)
ADI 29371-IgG1
Amino acid sequence of the HC
(SEQ ID NO: 95)
EVQLLESGGGLVQPGGSLRLSCAASGFTFGNYAMSWVRQAPGKGLEWVSMISGGGSTYYA

DSVKGRFTISRDNSKNTLYLQMNSLRAEDTAVYYCAKTPIYYGFDLWGRGTLVTVSSASTK

GPSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HEALHNHYTQKSLSLSPG

Amino acid sequence of the LC
(SEQ ID NO: 83)
ADI 30793-IgG1
Amino acid sequence of the HC
(SEQ ID NO: 96)
EVQLLESGGGLVQPGGSLRLSCAASGFTFDSYAMTWVRQAPGKGLEWVSVISGSGGKTYY

ADSVKGRFTISRDNSKNTLYLQMNSLRAEDTAVYYCAKTHLYYGFDLWGRGTLVTVSSAS

TKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDKSRWQQGNVFSCS

VMHEALHNHYTQKSLSLSPG

Amino acid sequence of the LC
(SEQ ID NO: 86)
ADI 30794-IgG1
Amino acid sequence of the HC
(SEQ ID NO: 97)
EVQLLESGGGLVQPGGSLRLSCAASGFTFGNYAMSWVRQAPGKGLEWVSAISGSGGKTY

YADSVKGRFTISRDNSKNTLYLQMNSLRAEDTAVYYCAKTAIYYGFDLWGRGTLVTVSSA

STKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDKSRWQQGNVFSCS

VMHEALHNHYTQKSLSLSPG

-continued

Amino acid sequence of the LC
(SEQ ID NO: 86)

Amino acid sequence of CD47 protein
(SEQ ID NO: 56)
MWPLVAALLLGSACCGSAQLLFNKTKSVEFTFCNDTVVIPCFVTNMEAQNTTEVYVKWKF

KGRDIYTFDGALNKSTVPTDFSSAKIEVSQLLKGDASLKMDKSDAVSHTGNYTCEVTELTR

EGETIIELKYRVVSWFSPNENILIVIFPIFAILLFWGQFGIKTLKYRSGGMDEKTIALLVAGLVI

TVIVIVGAILFVPGEYSLKNATGLGLIVTSTGILILLHYYVFSTAIGLTSFVIAILVIQVIAYILAV

VGLSLCIAACIPMHGPLLISGLSILALAQLLGLVYMKFVE

Sequences of the negative control present in appended drawings are as follows:

IgG1 HC:
(SEQ ID NO: 104)
MGWSLILLFLVAVATRVLSEVRLLESGGGLVQPGGSLRLSCAASGFT

FSNYAMGWVRQAPGKGLEWVSAISGSGGSTYYADSVKGRFTTSRDDS

KNALYLQMNSLRAEDTAVYYCARGGPGWYAADVWGQGTTVTVSSAST

KGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTV

LHQDWLNGKEYKCKVSNKALPAPIEKTISKAKGQPREPQVYTLPPSR

DELTKNQVSLTCLVKGFYPSDIAVEWESNGQPENNYKTTPPVLDSDG

SFFLYSKLTVDKSRWQQGNVFSCSVMHEALHNHYTQKSLSLSPG

IgG1 LC
(SEQ ID NO: 105)
MDFQVQIISFLLISASVIMSRGDIQMTQSPSSLSASVGDRVTITCRA

SQSISSYLNWYQQKPGKAPKLLIYAASSLQSGVPSRFSGSGSGTDFT

LTISSLQPEDFATYYCQQADLPAFAFGGGTKVEIKRTVAAPSVFIFP

PSDEQLKSGTASVVCLLNNFYPREAKVQWKVDNALQSGNSQESVTEQ

DSKDSTYSLSSTLTLSKADYEKHKVYACEVTHQGLSSPVTKSFNRGE

C

IgG4 HC:
(SEQ ID NO: 106)
MGWSLILLFLVAVATRVLSEVRLLESGGGLVQPGGSLRLSCAASGFT

FSNYAMGWVRQAPGKGLEWVSAISGSGGSTYYADSVKGRFTTSRDDS

KNALYLQMNSLRAEDTAVYYCARGGPGWYAADVWGQGTTVTVSSAST

KGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKR

VESKYGPPCPPCPAPEFLGGPSVFLFPPKPKDTLMISRTPEVTCVVV

DVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEM

TKNQVSLTCLVKGFYPSDIAVEWESNGQPENNYKTTPPVLDSDGSFF

LYSRLTVDKSRWQEGNVFSCSVMHEALHNHYTQKSLSLSLGK

IgG4 LC:
(SEQ ID NO: 107)
MDFQVQIISFLLISASVIMSRGDIQMTQSPSSLSASVGDRVTITCRA

SQSISSYLNWYQQKPGKAPKLLIYAASSLQSGVPSRFSGSGSGTDFT

LTISSLQPEDFATYYCQQADLPAFAFGGGTKVEIKRTVAAPSVFIFP

PSDEQLKSGTASVVCLLNNFYPREAKVQWKVDNALQSGNSQESVTEQ

DSKDSTYSLSSTLTLSKADYEKHKVYACEVTHQGLSSPVTKSFNRGE

C

The negative control of IgG1 Class is used when test antibodies of IgG1 Class are used; and the negative control of IgG4 Class is used when test antibodies of IgG4 Class are used.

EXAMPLES

Example 1. Production and Purification of an Anti-CD47 Antibody and the Control Antibody In the section "sequence listing" of the present application are listed the amino acid sequences of the CDR regions, of the light and heavy chain variable regions, and of the light and heavy chains of 10 antibodies exemplified in the present invention (ADI-26624, ADI-29336, ADI-29340, ADI-26630, ADI-29341, ADI-29349, ADI-26591, ADI-29371, ADI-30793, ADI-30794), as well as the corresponsive nucleotide sequences. Additionally, the sequence numbering for the light heavy chains, the heavy chains, the light and heavy chain variable regions of the exemplary antibodies above-mentioned in the present invention are shown in Table 1.

The antibody of the invention was expressed in yeast cells and CHO-S cells and purified.

Expression and Purification in Yeast cells

The yeast-based antibody presentation libraries (Adimab) were amplified according to the existing procedures (WO2009036379; WO 2010105256; WO2012009568), with the diversity in each library being $1×10^9$. In brief, magnetic activated cell sorting was performed with MACS system from Miltenyi Company in the first two rounds of screening. First, the yeast cells in the libraries (~$1×10^{19}$ cells/library) were incubated separately in a FACS washing buffer (a phosphate buffer with 0.1% bovine serum protein) containing 100 nM biotin-labeled CD47 antigen (Acro Biosystems, Catalogues number CD7-H5227-1 mg) at room temperature for 15 min Cells were washed with 50 ml of pre-cooled FACS washing buffer, then resuspended in 40 ml of the same washing buffer, and incubated at 4° C. for 15 min after addition of 500 µl of Streptinomycin microbead (Miltenyi LS). After the supernatant was discarded by centrifugation at 1000 rpm for 5 min, cell pellets were resuspended in 5 ml of FACS washing buffer and the cell suspension was loaded onto the Miltenyi LS column. After completion of loading, the column was washed with the FACS washing buffer 3 times with 3 ml for each wash. The Miltenyi LS column was taken off the magnetic region and eluted with 5 ml of the growth medium. The eluted yeast cells were collected and grown overnight at 37° C.

A flow cytometer was used for the next round of sorting: Approximately $1 \times 10^8$ of yeast cells obtained through MACS system screening were washed with FACS buffer thrice, and cultured in a culture broth containing biotin-labelled CD47 antigen at a low concentration (100-1 nM) at the room temperature. The culture broth was discarded, and the cells were washed with the FACS washing buffer twice and then mixed with LC-FITC (FITC-labelled goat antibody against human immunoglobin F(ab') kappa chain, Southern Biotech) (1:100 diluted) reagent, and with SA-633 (streptavidin-633, Molecular Probes) (1:500 diluted) or SA-PE (streptavidin-phycoerythrin, Sigma) (1:50 diluted) reagent, incubated at 4° C. for 15 min. The cells were eluted with the pre-cooled FACS washing buffer twice, centrifuged, re-suspended in 0.4 ml of the buffer, and transferred into a separation tube with a filter. The cells were sorted with FACS ARIA (BD Biosciences).

Yeast cells obtained through the screening which expressed anti-CD47 antibodies were induced at 30° C. for 48 hours with shaking, to express antibodies against CD47. After completion of the induction, yeast cells were removed by centrifugation at 1300 rpm for 10 min and the supernatant harvested. Anti-CD47 antibodies in the supernatant were purified on a Protein A column, eluted with an acetate solution of pH 2.0. Anti-CD47 antibodies were harvested with the antibody purity of >95%. The corresponsive Fab fragments could be obtained by papain digestion and purification with KappaSelect (GE Healthcare Life Sciences).

Expression and Purification in CHO-S Cells

A CHO-S cell line expressing the antibody was established using Freedom® CHO-S® kit (Invitrogen) according to the manufacturers' instructions. First, DNA sequences for the heavy and the light chains of the antibody molecule were inserted into the same pCHO1.0 plasmid, wherein the heavy chain is upstream of the light chain. The constructed pCHO1.0 plasmid was then transferred into the CHO cell line with chemical transfection and electroporation. The antibody yield was detected using ForteBio 48 hr after the transfection, to determine the transfection efficiency. A cell pool with high antibody expression was obtained after the transfected cells were subject to two rounds of selective screening. The cell pool was then propagated to express abundantly antibodies, and the cell supernatant was collected and purified on the Protein A column with the purity of antibody>95%.

TABLE 1

Numbering for the amino acid sequences of the light heavy chains, the heavy chains, the light and heavy chain variable regions of the 10 exemplary antibodies obtained in the present invention

| Antibody name | VH | VL | HC | LC |
| --- | --- | --- | --- | --- |
| ADI-26624 | 44 | 54 | 74/88 | 75 |
| ADI-29336 | 45 | 54 | 76/89 | 75 |
| ADI-29340 | 46 | 54 | 77/90 | 75 |
| ADI-26630 | 47 | 55 | 78/91 | 79 |
| ADI-29341 | 48 | 55 | 80/92 | 79 |
| ADI-29349 | 49 | 55 | 81/93 | 79 |
| ADI-26591 | 50 | 57 | 82/94 | 83 |
| ADI-29371 | 51 | 57 | 84/95 | 83 |

TABLE 1-continued

Numbering for the amino acid sequences of the light heavy chains, the heavy chains, the light and heavy chain variable regions of the 10 exemplary antibodies obtained in the present invention

| Antibody name | VH | VL | HC | LC |
| --- | --- | --- | --- | --- |
| ADI-30793 | 52 | 58 | 85/96 | 86 |
| ADI-30794 | 53 | 58 | 87/97 | 86 |

The following control antibodies used in the Example were expressed in 293HEK cells and purified:

| Control antibody |
| --- |
| Hu5F9 |
| AB6.12 |

Hu5F9 is a human anti-CD47 antibody transiently expressed in 293 HEK cell, with the same sequence as that of the antibody "5F9" in U.S. Patent US2015/0183874 A1. AB6.12 is a humanized anti-CD47 antibody transiently expressed in 293 HEK cell, with the same sequence as that of the antibody "AB6.12" in U.S. Pat. No. 9,045,541. The antibody "AB6.12" disclosed in U.S. Pat. No. 9,045,541 is a anti-CD47 antibody which will not result in apparent agglutination of cells.

For transient expression of the antibody in 293HEK cells, a vector pTT5 was used. First, the heavy and the light chains of the antibody were cloned into the single pTT5 vector. The pTT5 vector bearing the heavy and the light chains of the antibody was transfected with chemical transfection into 293HEK cells. The chemical transfection reagent used is PEI (purchased from Polysciences) and the transiently transfecting 293HEK cells were performed according to the protocol provided by the manufacturer. First, the plasmid DNA and transfection reagents were prepared in a clean bench, half of F17 culture medium (Gibco) (volume of which is ⅕ of the transfection volume) was each added into a 50 ml centrifuge tube, with one half being supplemented with the filtrated plasmid (130 µg/100 ml) and another half being supplemented with the filtrated PEI (1 g/L, Polysciences) (the mass ratio (plasmid:PEI)=1:3), each mixed well for 5 min. Then, the two halves were gently mixed 20 time and left to stand for 15-30 min, with longer than 30 min not permitted. The DNA/PEI mixture was poured gently into 293HEK cells and well mixed. The cells ware cultured under a condition of 37° C., 8% $CO_2$ for 7 days and fresh medium was added every 48 hrs. After 7 days or continuous culturing to cell viability of ≤60%, a centrifugation was performed at 13000 rpm for 20 min. The supernatant was collected and purified on the Protein A column with the purity of antibody>95%.

Example 2: Affinity Determination of an Anti-CD47 Antibody of the Invention

The equilibrium dissociation constant ($K_D$) of the 10 exemplary antibodies mentioned above in the present invention for human CD47 (hCD47) (Fab fragments used in the monovalency test to rule out the potential impact by Fc fragments), was determined with the bio-light interferometry (ForteBio) assay.

ForteBio affinity assay was performed generally as previously described (Estep, P., et al., High throughput solution Based measurement of antibody-antigen affinity and epitope binding. MAbs, 2013, 5 (2): p. 270-8). In brief, Sensors were equilibrated off-line in assay buffer for 30 min and then tested on-line for 60 sec to establish the base line. The purified antibody obtained as described above was loaded on-line onto AHQ sensor (ForteBio) to perform ForteBio affinity measurement. Then, the sensor loaded with the antibody was exposed to 100 nM of CD47 antigen for 5 min, followed by transferring the sensor into the assay buffer for 5 min to measure the dissociation rate. A kinetics analysis was performed using the 1:1 binding model.

In the test conducted as described in the above assay, affinities of ADI-26624, ADI-26630, ADI-26591, ADI-29336, ADI-29340, ADI-29341, ADI-29349, ADI-29371, ADI-30793, and ADI-30794 are shown in Table 2.

Accuri C6 System (BD Biosciences) and a concentration-dependent graph was fitted with GraphPad, according to MFI of the cells.

ADI-26591, ADI-26624 and ADI-26630 (in IgG1 format, expressed in yeast) bind to the hCD47 overexpressed on CHO cells (SEQ ID NO: 56) with $EC_{50}$ values of 3.77 nM, 2.254 nM and 3.895 nM, respectively, consistent with the binding ability of the control antibody Hu5F9 to the hCD47 overexpressed on CHO cells (the $EC_{50}$ value of the control antibody Hu5F9 being 3.726 nM) (See FIG. 1).

In the test conducted as described in the above assay, ADI-29336, ADI-29340, ADI-29341, ADI-29349, ADI-29371, ADI-30793, and ADI-30794 in IgG1 format produced in yeast cells bind to the hCD47 overexpressed on

TABLE 2

Binding of the antibody of the invention in IgG1 format measured by bio-light interferometry

| Antibody | ForteBio Image: Human CD47-Fc at the tip of AHQ, the antibody in Fab format in a solution (100 nM) [monovalent] | ForteBio Image: The antibody in IgG1 format at the tip of AHQ, human CD47-Fc in a solution (100 nM) [bivalent] | ForteBio Image: The antibody in IgG1 format at the tip of AHQ, cynomolgus CD47-Fc in a solution (100 nM) [bivalent] | ForteBio Image: The antibody in IgG1 format at the tip of AHQ, mouse CD47-Fc in a solution (100 nM) [bivalent] |
|---|---|---|---|---|
| ADI-26591 | N.B. | 5.38E−09 | 3.39E−09 | N.B. |
| ADI-29371 | 2.18E−07 | 1.95E−09 | 1.41E−09 | N.B. |
| ADI-30793 | 9.34E−09 | 6.32E−10 | 5.84E−10 | 4.57E−09 |
| ADI-30794 | 3.13E−09 | 5.62E−10 | 7.84E−10 | N.B. |
| ADI-26624 | 6.578E−08 | 1.054E−09 | 7.827E−10 | N.B. |
| ADI-29336 | 1.325E−09 | 4.768E−10 | 5.43626E−10 | N.B. |
| ADI-29340 | 5.484E−09 | 4.885E−10 | 6.12182E−10 | 2.12E−08 |
| ADI-26630 | 3.567E−08 | 8.37E−10 | 7.27E−10 | N.B. |
| ADI-29341 | 4.623E−09 | 5.006E−10 | 5.30363E−10 | N.B. |
| ADI-29349 | 4.511E−09 | 5.552E−10 | 5.67054E−10 | 1.72E−08 |
| Hu5F9 | 1.66E−08 | 4.20E−10 | 6.41E−10 | 1.266E−08 |

Note:
N.B. indicates no binding.

It can be seen that all of the 10 exemplary antibodies mentioned above in the invention exhibit very high affinities, comparable to the affinity of Hu5F9, an anti-CD47 antibody known and recognized in the art.

Example 3: Anti-CD47 Antibody of the Present Invention Binding to Human CD47

In an assay on the basis of flow cytometery, binding of the 10 exemplary antibodies mentioned above in the invention to the human CD47 was measured.

CHO cells overexpressing human CD47 (CHO-hCD47 cells) were created by transfecting CHO cells with a pCHO1.0 vector (Invitrogen) which bears a human CD47 cDNA (Sino Biological) cloned into the multiple cloning site (MCS). CHO-hCD47 cells ($0.2 \times 10^6$ cells) were mixed with the test antibodies at different concentrations (the 10 exemplary antibodies mentioned above in the invention and Hu5F9, the maximal concentration of 900 nM, threefold dilution, totally tested at 11 concentrations) in PBS with 0.1% bovine serum albumin (BSA) and incubated on ice for 30 min. Then the cells were washed at least two times and incubated with a secondary antibody (PE-labelled goat anti-human IgG antibody, Southern Biotech, final concentration of 5 μg/ml) in PBS with 0.1% BSA on ice for 30 min (in dark). The cells were washed at least two times and analyzed by flow cytometry. Flow cytometry was performed on CHO cells with $EC_{50}$ values of 6.725 nM, 3.529 nM, 3.344 nM, 3.13 nM, 2.132 nM, 2.921 nM and 3.697 nM, respectively, essentially consistent with the binding ability of the control antibody Hu5F9 to the CD47 overexpressed on CHO cells (with the $EC_{50}$ value of 3.726 nM).

The antibodies ADI-29336, ADI-29340, ADI-29341, ADI-29349 and ADI-29371 in IgG4 format produced in CHO cells bind to hCD47 overexpressed on CHO cells with $EC_{50}$ values of 2.475 nM, 2.194 nM, 1.892 nM, 2.043 nM and 2.31 nM, respectively, the affinities of these antibodies to hCD47 at the cellular level all being higher than that of the control antibody Hu5F9 (with the $EC_{50}$ value of 3.726 nM).

Example 4. Anti-CD47 Antibody of the Invention Blocking Interaction of the Human CD47 Ligand SIRPα with CD47

Ability of the 10 exemplary antibodies to block human CD47 binding to SIRPα was measured with flow cytometry.

$0.2 \times 10^6$ of the human CD47-expressing CHO cells prepared as described previously in Example 3 were co-incubated with the test antibodies (ADI-26624, ADI-26630, ADI-29336, ADI-29340, ADI-29341, ADI-29349 and Hu5F9, the maximal concentration of 900 nM, threefold dilution, totally tested at 11 concentrations) and 200 nM of a mouse Fc-labelled SIRPα protein (Acro Biosystems) in PBS with 0.1% BSA on ice for 30 min. Then the cells were washed 3 times and subsequently incubated with a secondary antibody, goat-anti-mouse IgG-APC (Allophycocyanin) (Biolegend), in PBS with 0.1% BSA on ice for 30 min (in dark). Cells were washed 3 times. Flow cytometry assay was performed on Accuri C6 System (BD Biosciences) and MFI was calculated with C6 software.

The abilities of ADI-26624, ADI-29336, ADI-29340, ADI-29371, ADI-26630, ADI-29341 and ADI-29349 in IgG1 format produced in yeast cells to block the human SIRPα-APC binding to CD47 are consistent with that of the control antibody AB6.12.

Specifically, $IC_{50}$ values for the abilities of ADI-26624, ADI-29336, and ADI-29340 to block the human SIRPα-APC binding to CD47 are 11.2 nM, 8.548 nM, and 5.081 nM, respectively. $IC_{50}$ values for the abilities of ADI-26630, ADI-29341, and ADI-29349 to block the human SIRPα-APC binding to CD47 are 2.986 nM, 2.476 nM, and 3.097 nM, respectively. $IC_{50}$ value for the ability of the control antibody AB6.12 to block the human SIRPα-APC binding to CD47 is 3.385 nM. (See FIG. 2).

The abilities of the antibodies ADI-26624, ADI-26630, ADI-29336, ADI-29340, ADI-29341 and ADI-29349 in IgG4 format produced in CHO cells to block the human SIRPα-APC binding to CD47 are all slightly higher than those of the control antibodies AB6.12 and Hu5F9.

Specifically, $IC_{50}$ values for the abilities of ADI-26624, ADI-29336, and ADI-29340 to block the human SIRPα-APC binding to CD47 are 1.043 nM, 1.389 nM, and 1.223 nM, respectively. $IC_{50}$ values for the abilities of ADI-26630, ADI-29341, and ADI-29349 to block the human SIRPα-APC binding to CD47 are 1.123 nM, 0.6042 nM, and 0.7355 nM, respectively. $IC_{50}$ values for the abilities of the control antibodies AB6.12 and Hu5F9 to block the human SIRPα-APC binding to CD47 are 1.768 nM and 1.843 nM, respectively. (See FIG. 3).

Example 5. Detection of the Ability of an Anti-CD47 Antibody of the Invention to Facilitate Phagocytosis of Tumor Cells by Macrophages In an assay on the basis of flow cytometery, the abilities of the antibodies of the invention (ADI-26624, ADI-29336, ADI-29340, ADI-26630, ADI-29341, ADI-29349, ADI-29371, ADI-30793 and ADI-30794) to facilitate phagocytosis of tumor cells by macrophages were measured.

Fresh blood taken from a donor underwent density gradient centrifugation, resulting in peripheral blood mononucleated cells (PBMCs). CD14 positive monocytes were obtained and purified from the isolated PBMC according to the instructions of a kit (EasySep™ Human CD14 Positive Selection Kit, Steam Cell), and 10 ng/mL granulocyte-macrophage colony-stimulating factor (GM-CSF, R&D Systems) was added, followed by adherent culture for 7 continuous days, during which 20 ng/mL interferon-γ (IFN-γ, Acro Biosystem) was added for stimulation of 1 hour on Day 5 and subsequently 100 ng/mL lipopolysaccharide (LPS, Sigma) was added for additional stimulation of 48 hour. Thus, the monocytes were induced into macrophages. The target tumor cells CCRF-CEM (purchased from ATCC) were fluorescently-labeled according to the instructions of the CellTrace™ CFSE kit. The labelled tumor cells were co-culture with the differentiated macrophage mentioned above at a ratio of 4:1, while the test antibodies were added at different concentrations and incubated at 37° C. for 3 hrs. Then the cells were washed at least two times, followed by addition of an allophycocyanin (APC)-labelled anti-CD14 antibody (purchased from BD), and incubated in PBS with 0.1% BSA on ice for 30 min (in dark). The cells were washed at least two times and analyzed by flow cytometry. The phagocytized population of cells is that of the living cells which are positive for both CD14 and the fluorescence dye CFSE (carboxyfluorescein diacetate, succinimidyl ester).

ADI-29336, ADI-29340, ADI-29341, ADI-29349, ADI-30793, and ADI-30794 in IgG1 format produced in yeast cells all have very strong abilities to facilitate phagocytosis of tumor cells by macrophages. The ability of ADI-29340 to facilitate phagocytosis of tumor cells by macrophages is stronger than those of the control antibodies Hu5F9 and AB6.12, while the ability of ADI-30793 and ADI-30794 to facilitate phagocytosis of tumor cells by macrophages is comparable to that of the control antibody AB6.12 (See FIGS. 4 and 5).

ADI-26624 and ADI-26630 in IgG4 format produced in CHO cells can facilitate effectively phagocytosis of tumor cells by macrophages. The abilities of ADI-26624 and ADI-26630 to facilitate phagocytosis of tumor cells by macrophages are consistent with that of the control antibody Hu5F9 (See FIG. 6).

ADI-29336, ADI-29340, ADI-29341, ADI-29349 and ADI-29371 in IgG4 format produced in CHO cells all have very strong abilities to facilitate phagocytosis of tumor cells by macrophages. It can be seen from the results that the abilities of ADI-29336, ADI-29340, ADI-29341 and ADI-29349 to facilitate phagocytosis of tumor cells by macrophages are significantly higher than that of the control antibody Hu5F9, and the ability of ADI-29371 to facilitate phagocytosis of tumor cells by macrophages is comparable to that of the control antibody Hu5F9 (See FIG. 7).

Example 6. Anti-Tumor Activity of an Anti-CD47 Antibody of the Invention

The anti-tumor efficacy of the anti-CD47 antibody of the invention (ADI-26624, ADI-26630, ADI-29340 and ADI29341) is studied in a NOD/SCID mouse model.

The procedure is as follows:

Human Burkitt's lymphomas Raji cells (ATCC #CCL-86) was purchased from ATCC and routinely sub-cultured strictly according to ATCC requirements for the subsequent in vivo experiments. Cells were collected by centrifugation, resuspended in sterile PBS and adjusted to a cell density of $10^7$ cells/ml. 0.1 ml of the cell suspension was drew and mixed with Matrigel at 1:1 to be inoculated subcutaneously into the right flank of NOD/SCID mice (Beijing Vital River Laboratory Animal Technology Co., Ltd.). Tumor and the body weight were measured weekly twice throughout the study. Mice were euthanized when tumor endpoints were met or the mice had a body weight loss of >20%. 10 days after inoculation, the mice eligible for the experiment were randomized with 8 animals per group. Tumor volumes in the mice were measured by a caliper with the following formula: (breadth) 2×length/2 in each group, with the maximal tumor volume in each group of mice being 110 $mm^3$.

First, the applicants studied the efficacy of the antibodies ADI-26624 and ADI-26630 of the present invention to inhibit tumor.

The mice obtained by the method mentioned above were randomized and subject to different treatments: intraperitoneal injection of 1 mg/kg or 5 mg/kg of PBS, the control IgG antibody (IgG4), Benchmark (Hu5F9), and the antibodies ADI-26624 and ADI-26630 of the present invention with an administration frequency of once every other day for 2 consecutive weeks. The detailed grouping and the mode of administration are shown in Table 3:

TABLE 3

| Group | Inoculated Cells | Treatment modality | |
|---|---|---|---|
| 1 | Raji cells:Matrigel (1:1) | PBS | |
| 2 | Raji cells:Matrigel (1:1) | IgG control (5 mg/kg) | once every other day for two consecutive weeks |
| 3 | Raji cells:Matrigel (1:1) | Hu5F9 (5 mg/kg) | once every other day for two consecutive weeks |
| 4 | Raji cells:Matrigel (1:1) | Hu5F9 (1 mg/kg) | once every other day for two consecutive weeks |
| 5 | Raji cells:Matrigel (1:1) | AD126624 (5 mg/kg) | once every other day for two consecutive weeks |
| 6 | Raji cells:Matrigel (1:1) | AD126624 (1 mg/kg) | once every other day for two consecutive weeks |
| 7 | Raji cells:Matrigel (1:1) | AD126630 (5 mg/kg) | once every other day for two consecutive weeks |
| 8 | Raji cells:Matrigel (1:1) | AD126630 (1 mg/kg) | once every other day for two consecutive weeks |

At the end of the experiment, the tumor growth inhibition rate was calculated with the following formula:

$$TGI\% = 100\% \times ((Tvol_{post\ PBS\ treatment} - Tvol_{post\ antibody\ treatment}) / (Tvol_{post\ PBS\ treatment} - Tvol_{prior\ to\ PBS\ treatment})),$$

wherein $Tvol_{post\ PBS\ treatment}$ is the tumor volume after completion of the experiment in the blank control PBS Group, $Tvol_{post\ antibody\ treatment}$ is the tumor volume after completion of the experiment in the antibody Groups (IgG, Hu5F9 and the antibodies of the present invention), and $Tvol_{prior\ to\ PBS\ treatment}$ is the initial tumor volume in the blank control PBS Group.

For the experimental result, see FIGS. 8, 9 and Table 4 below. It can be seen that the anti-CD47 monoclonal antibodies ADI-26624 and ADI-26630 in IgG4 format of the present application expressed in CHO cells inhibit significantly growth of the tumor, compared to the control IgG (equitech-Bio) and the control antibody Hu5F9.

The tumor growth inhibition rate in Arms ADI-26630 of 1 mg/kg, ADI-26630 of 5 mg/kg, ADI-26624 of 1 mg/kg, and ADI-26624 of 5 mg/kg are 100%, 104%, 79%, 94%, respectively. Tumors disappeared completely in 5/8 mice in Arm ADI-26630 of 5 mg/kg, and 2/8 mice in Arm ADI-26630 of 1 mg/kg, where the number of the animals with complete disappearance of tumors in both Arms are higher than that in the control antibody Hu5F9 Arm at the same dosage (2 animals in Arms at 5 mg/kg and 1 animal in Arms at 5 mg/kg) (Table 4). The mice in all Arms in this study had no significant change in body weight 32 days after inoculation.

Thus, it can be seen that the antibody of the invention exhibits very good therapeutic effect for tumor which is superior over the therapeutic effect of the control antibody Hu5F9.

TABLE 4

Statistical table for tumor size and tumor growth inhibition rate in the study with the present antibody in IgG4 format expressed in CHO cells.

| Group | Initial tumor volume (mm³) | Tumor volume at the end of the experiment (mm³) | Ratio of growth inhibition (%) | The number of the animals with complete disappearance of tumors | Proportion of animals with complete disappearance of tumors (%) |
|---|---|---|---|---|---|
| PBS (blank control) | 111 | 1711 | | 0/8 | 0 |
| human IgG (negative control), 5 mg/kg | 110 | 1496 | 13 | 0/8 | 0 |
| Hu5F9, 1 mg/kg | 110 | 207 | 94 | 1/8 | 12 |
| Hu5F9, 5 mg/kg | 111 | 119 | 100 | 2/8 | 25 |
| ADI-26630, 1 mg/kg | 110 | 113 | 100 | 2/8 | 25 |
| ADI-26630, 5 mg/kg | 109 | 48 | 104 | 5/8 | 63 |
| ADI-26624, 1 mg/kg | 110 | 445 | 79 | 0/8 | 0 |
| ADI-26624, 5 mg/kg | 110 | 215 | 94 | 0/8 | 0 |

Next, the present inventors proceeds with detecting inhibitory effects of the antibodies ADI-29340 and ADI29341 on tumor.

The mice obtained by the method mentioned above were randomized and subject to different treatments, that is, intraperitoneal injection of 0.5 mg/kg or 5 mg/kg of PBS, the control IgG antibody (IgG4), and the antibodies ADI-26630, ADI-29340 and ADI29341 of the present invention, once every other day for 2 consecutive weeks. The detailed grouping and the mode of administration are shown in Table 5 below:

TABLE 5

| Group | Inoculated Cells | Treatment modality | |
|---|---|---|---|
| 1 | Raji cells:Matrigel (1:1) | PBS | |
| 2 | Raji cells:Matrigel (1:1) | Human IgG control (5 mg/kg) | once every other day for two consecutive weeks |
| 3 | Raji cells:Matrigel (1:1) | AD126630 (5 mg/kg) | once every other day for two consecutive weeks |
| 4 | Raji cells:Matrigel (1:1) | AD126630 (0.5 mg/kg) | once every other day for two consecutive weeks |
| 5 | Raji cells:Matrigel (1:1) | AD1269340 (5 mg/kg) | once every other day for two consecutive weeks |
| 6 | Raji cells:Matrigel (1:1) | AD129340 (0.5 mg/kg) | once every other day for two consecutive weeks |
| 7 | Raji cells:Matrigel (1:1) | AD1269341 (5 mg/kg) | once every other day for two consecutive weeks |
| 8 | Raji cells:Matrigel (1:1) | AD129341 (0.5 mg/kg) | once every other day for two consecutive weeks |

At the end of the experiment, the tumor growth inhibition rate was calculated with the abovementioned formula. It was found that the anti-CD47 monoclonal antibodies ADI-26630, ADI-29340 and ADI-29341 in IgG4 format of the present application expressed in CHO cells could inhibit significantly growth of the tumor (Table 6, FIG. 10 and FIG. 11).

The tumor growth inhibition rate in Arms ADI-26630 of 0.5 mg/kg, ADI-26630 of 5 mg/kg, ADI-29340 of 0.5 mg/kg, ADI-29340 of 5 mg/kg, ADI-29341 of 0.5 mg/kg, and ADI-29341 of 5 mg/kg are 99%, 110%, 103%, 109%, 104%, and 109%, respectively. Tumors disappeared completely in 5/8 mice in Arm ADI-29340 of 0.5 mg/kg, 4/8 mice in Arm ADI-29341 of 0.5 mg/kg, and 8/8 mice in Arms ADI-26630 and ADI-29340 of 5 mg/kg (Table 6). The mice in all Arms in this study had no significant change in body weight 30 days after inoculation.

Thus, it can be seen that the antibody of the invention exhibits very good therapeutic effect on tumor.

TABLE 6

Statistical table for tumor size and tumor growth inhibition rate in the study with the present antibody in IgG4 format expressed in CHO cells.

| Group | Initial tumor volume (mm³) | Tumor volume at the end of the experiment (mm³) | Ratio of growth inhibition (%) | The number of the animals with complete disappearance of tumors | Proportion of animals with complete disappearance of tumors (%) |
|---|---|---|---|---|---|
| PBS (blank control) | 101 | 1047 | | 0/8 | 0 |
| h-IgG, 5 mg/kg | 100 | 1089 | | 0/8 | 0 |
| ADI26630, 0.5 mg/kg | 99 | 113 | 99 | 1/8 | 12.5 |
| ADI26630, 5 mg/kg | 99 | 0 | 110 | 8/8 | 100 |
| ADI29340, 0.5 mg/kg | 98 | 69 | 103 | 5/8 | 62.5 |
| ADI29340, 5 mg/kg | 99 | 8 | 109 | 8/8 | 100 |
| ADI29341, 0.5 mg/kg | 99 | 60 | 104 | 4/8 | 50 |
| ADI29341, 5 mg/kg | 99 | 12 | 109 | 7/8 | 87.5 |

Example 7. Detection of the Activity of an Anti-CD47 Antibody of the Invention to Facilitate RBC Agglutination It is known in the art that most anti-CD47 antibodies have the side effect of facilitating RBC agglutination, thereby limiting the therapeutic applications of these antibodies. Therefore, the present inventors further investigated the RBC agglutination of the antibodies disclosed in the present application.

The test procedure is as follows:

Fresh human blood is collected and washed with PBS thrice to prepare a 10% of human RBC suspension. The human RBCs are incubated with the test antibody (maximal concentration of 60 ug/ml, threefold dilution, total of 11 concentrations) in a 96-well round bottom plate at 37° C. for 2-6 hours. After the reaction ended, a photographs is taken and the result is judged. The criteria for result adjudication is that RBC agglutination reaction occurs if the red blood cells settle and spread in reticulation at the bottom of the well, appearing as a haze (see the result for Hu5F9 in FIG. 12), and RBC agglutination reaction does not occur if RBC would settle in a punctuate red dot at the bottom of the well (see the control in FIG. 12)

In the test conducted as described in the above assay, the result of the hemagglutinating reaction was shown in FIG. 12. It can be seen from FIG. 12 that the activities of ADI26630, ADI29340 and ADI29341 in RBC agglutination are very weak, and that the activities of the same to facilitate RBC agglutination is significantly lower than that of the control Hu5F9, and comparable to that of the control AB6.12. It can be seen that the antibodies disclosed in the present application have significantly decreased agglutination of blood cells, and consequently may result in the significantly decreased side effect in clinical treatment paradigm and can be used extensively in treatment of various cancers.

The invention claimed is:

1. An isolated anti-CD47 monoclonal antibody or an antigen binding fragment thereof, comprising:
   (i) three complementarity determining regions HCDRs of the heavy chain variable region comprising the amino acid sequence set forth in SEQ ID NO: 44, 45 or 46, and three complementarity determining regions LCDRs of the variable region of a light chain comprising the amino acid sequence set forth in SEQ ID NO: 54;
   (ii) three complementarity determining regions HCDRs of the heavy chain variable region comprising the amino acid sequence set forth in SEQ ID NO: 47, 48 or 49, and three complementarity determining regions LCDRs of the variable region of a light chain comprising the amino acid sequence set forth in SEQ ID NO: 55;
   (iii) three complementarity determining regions HCDRs of the heavy chain variable region comprising the amino acid sequence set forth in SEQ ID NO: 50 or 51, and three complementarity determining regions LCDRs of the variable region of a light chain comprising the amino acid sequence set forth in SEQ ID NO: 57; or
   (iv) three complementarity determining regions HCDRs of the heavy chain variable region comprising the amino acid sequence set forth in SEQ ID NO: 52 or 53, and three complementarity determining regions LCDRs of the variable region of a light chain comprising the amino acid sequence set forth in SEQ ID NO: 58.

2. An isolated anti-CD47 monoclonal antibody or an antigen binding fragment thereof, comprising three complementarity determining regions HCDR1, HCDR2 and HCDR3 of the heavy chain variable region and three complementarity determining regions LCDR1, LCDR2 and LCDR3 of the light chain variable region, wherein:
   (i) HCDR1 comprises the amino acid sequence as shown in SEQ ID NO: 1, HCDR2 comprises the amino acid sequence as shown in SEQ ID NO: 9, HCDR3 comprises the amino acid sequence as shown in SEQ ID NO: 17, LCDR1 comprises the amino acid sequence as shown in SEQ ID NO: 23, LCDR2 comprises the amino acid sequence as shown in SEQ ID NO: 25, and LCDR3 comprises the amino acid sequence as shown in SEQ ID NO: 27;
   (ii) HCDR1 comprises the amino acid sequence as shown in SEQ ID NO: 2, HCDR2 comprises the amino acid sequence as shown in SEQ ID NO: 10, HCDR3 comprises the amino acid sequence as shown in SEQ ID NO: 18, LCDR1 comprises the amino acid sequence as shown in SEQ ID NO: 23, LCDR2 comprises the amino acid sequence as shown in SEQ ID NO: 25, and LCDR3 comprises the amino acid sequence as shown in SEQ ID NO: 27;

(iii) HCDR1 comprises the amino acid sequence as shown in SEQ ID NO: 3, HCDR2 comprises the amino acid sequence as shown in SEQ ID NO: 11, HCDR3 comprises the amino acid sequence as shown in SEQ ID NO: 17, LCDR1 comprises the amino acid sequence as shown in SEQ ID NO: 23, LCDR2 comprises the amino acid sequence as shown in SEQ ID NO: 25, and LCDR3 comprises the amino acid sequence as shown in SEQ ID NO: 27;

(iv) HCDR1 comprises the amino acid sequence as shown in SEQ ID NO: 1, HCDR2 comprises the amino acid sequence as shown in SEQ ID NO: 9, HCDR3 comprises the amino acid sequence as shown in SEQ ID NO: 19, LCDR1 comprises the amino acid sequence as shown in SEQ ID NO: 23, LCDR2 comprises the amino acid sequence as shown in SEQ ID NO: 25, and LCDR3 comprises the amino acid sequence as shown in SEQ ID NO: 28;

(v) HCDR1 comprises the amino acid sequence as shown in SEQ ID NO: 4, HCDR2 comprises the amino acid sequence as shown in SEQ ID NO: 9, HCDR3 comprises the amino acid sequence as shown in SEQ ID NO: 19, LCDR1 comprises the amino acid sequence as shown in SEQ ID NO: 23, LCDR2 comprises the amino acid sequence as shown in SEQ ID NO: 25, and LCDR3 comprises the amino acid sequence as shown in SEQ ID NO: 28;

(vi) HCDR1 comprises the amino acid sequence as shown in SEQ ID NO: 5, HCDR2 comprises the amino acid sequence as shown in SEQ ID NO: 12, HCDR3 comprises the amino acid sequence as shown in SEQ ID NO: 19, LCDR1 comprises the amino acid sequence as shown in SEQ ID NO: 23, LCDR2 comprises the amino acid sequence as shown in SEQ ID NO: 25, and LCDR3 comprises the amino acid sequence as shown in SEQ ID NO: 28;

(vii) HCDR1 comprises the amino acid sequence as shown in SEQ ID NO: 6, HCDR2 comprises the amino acid sequence as shown in SEQ ID NO: 13, HCDR3 comprises the amino acid sequence as shown in SEQ ID NO: 20, LCDR1 comprises the amino acid sequence as shown in SEQ ID NO: 24, LCDR2 comprises the amino acid sequence as shown in SEQ ID NO: 26, and LCDR3 comprises the amino acid sequence as shown in SEQ ID NO: 29;

(viii) HCDR1 comprises the amino acid sequence as shown in SEQ ID NO: 7, HCDR2 comprises the amino acid sequence as shown in SEQ ID NO: 14, HCDR3 comprises the amino acid sequence as shown in SEQ ID NO: 20, LCDR1 comprises the amino acid sequence as shown in SEQ ID NO: 24, LCDR2 comprises the amino acid sequence as shown in SEQ ID NO: 26, and LCDR3 comprises the amino acid sequence as shown in SEQ ID NO: 29;

(ix) HCDR1 comprises the amino acid sequence as shown in SEQ ID NO: 8, HCDR2 comprises the amino acid sequence as shown in SEQ ID NO: 15, HCDR3 comprises the amino acid sequence as shown in SEQ ID NO: 21, LCDR1 comprises the amino acid sequence as shown in SEQ ID NO: 24, LCDR2 comprises the amino acid sequence as shown in SEQ ID NO: 26, and LCDR3 comprises the amino acid sequence as shown in SEQ ID NO: 30; or (x) HCDR1 comprises the amino acid sequence as shown in SEQ ID NO: 7, HCDR2 comprises the amino acid sequence as shown in SEQ ID NO: 16, HCDR3 comprises the amino acid sequence as shown in SEQ ID NO: 22, LCDR1 comprises the amino acid sequence as shown in SEQ ID NO: 24, LCDR2 comprises the amino acid sequence as shown in SEQ ID NO: 26, and LCDR3 comprises the amino acid sequence as shown in SEQ ID NO: 30.

3. The isolated monoclonal antibody or antigen binding fragment thereof according to claim 1, comprising:
(i) a heavy chain variable region comprising an amino acid sequence having at least 90% sequence identity to the amino acid sequence shown in SEQ ID NO: 44, 45 or 46, and a light chain variable region comprising an amino acid sequence having at least 90% sequence identity to the amino acid sequence shown in SEQ ID NO: 54,
(ii) a heavy chain variable region comprising an amino acid sequence having at least 90% sequence identity to the amino acid sequence shown in SEQ ID NO: 47, 48 or 49, and a light chain variable region comprising an amino acid sequence having at least 90% sequence identity to the amino acid sequence shown in SEQ ID NO: 55,
(iii) a heavy chain variable region comprising an amino acid sequence having at least 90% sequence identity to the amino acid sequence shown in SEQ ID NO: 50 or 51, and a light chain variable region comprising an amino acid sequence having at least 90% sequence identity to the amino acid sequence shown in SEQ ID NO: 57, or
(iv) a heavy chain variable region comprising an amino acid sequence having at least 90% sequence identity to the amino acid sequence shown in SEQ ID NO: 52 or 53, and a light chain variable region comprising an amino acid sequence having at least 90% sequence identity to the amino acid sequence shown in SEQ ID NO: 58.

4. The isolated monoclonal antibody or antigen-binding fragment thereof according to claim 1, comprising:
(i) a heavy chain comprising an amino acid sequence having at least 90% sequence identity to the amino acid sequence shown in SEQ ID NO: 74, 76, 77, 88, 89 or 90, and a light chain comprising an amino acid sequence having at least 90% sequence identity to the amino acid sequence shown in SEQ ID NO: 75,
(ii) a heavy chain comprising an amino acid sequence having at least 90% sequence identity to the amino acid sequence shown in SEQ ID NO: 78, 80, 81, 91, 92 or 93, and a light chain comprising an amino acid sequence having at least 90% sequence identity to the amino acid sequence shown in SEQ ID NO: 79,
(iii) a heavy chain comprising an amino acid sequence having at least 90% sequence identity to the amino acid sequence shown in SEQ ID NO: 82, 84, 94 or 95, and a light chain comprising an amino acid sequence having at least 90% sequence identity to the amino acid sequence shown in SEQ ID NO: 83, or
(iv) a heavy chain comprising an amino acid sequence having at least 90% sequence identity to the amino acid sequence shown in SEQ ID NO: 85, 87, 96 or 97, and a light chain comprising an amino acid sequence having at least 90% sequence identity to the amino acid sequence shown in SEQ ID NO: 86.

5. The isolated monoclonal antibody or antigen-binding fragment thereof according to claim 1, wherein said antibody is a humanized antibody or human antibody.

6. The isolated monoclonal antibody or antigen-binding fragment thereof according to claim 1, wherein said antigen-binding fragment is selected from the group consisting of Fab, Fab'-SH, Fv, scFv or (Fab')$_2$ fragment.

7. The isolated monoclonal antibody or antigen-binding fragment thereof according to claim 1, comprising framework sequence, wherein at least a portion of the framework sequence is a human consensus framework sequence.

8. An isolated nucleic acid encoding the isolated anti-CD47 monoclonal antibodies or antigen-binding fragments thereof of claim 1.

9. A vector comprising the nucleic acid of claim 8.

10. A host cell comprising the vector of claim 9, wherein said host cell being a prokaryotic or eukaryotic cell.

11. A method for preparing the anti-CD47 monoclonal antibody or an antigen-binding fragment thereof, comprising cultivation of the host cell of claim 10 under a condition which is suitable for expressing the anti-CD47 monoclonal antibodies or antigen-binding fragments thereof of claim 1.

12. The anti-CD47 monoclonal antibodies or antigen-binding fragments thereof prepared by the method of claim 11.

13. A pharmaceutical composition, comprising the anti-CD47 antibodies or antigen-binding fragments thereof according to claim 1, and pharmaceutical carriers, wherein said antigen-binding fragments are selected from the group consisting of Fab, Fab'-SH, Fv, scFv and (Fab')$_2$.

14. A method for treating a CD47-expressing cancer or tumor in a human subject or for alleviating the symptoms of the cancer or tumor, comprising administering to the human subject an effective amount of the pharmaceutical composition of claim 13.

15. The method of claim 14, wherein the cancer or tumor is hematologic neoplasias and solid tumors, selected from acute myelocytic leukemia (AML), chronic myelocytic leukemia (CML), acute lymphocytic leukemia (ALL), chronic lymphocytic leukemia (CLL), Non-Hodgkin's lymphoma (NHL), multiple myeloma (MM), lymphoma, breast carcinoma, head and neck cancer, gastric carcinoma, lung cancer, esophageal carcinoma, intestinal carcinoma, ovarian carcinoma, cervical carcinoma, hepatic carcinoma, renal carcinoma, pancreatic carcinoma, bladder carcinoma, colorectal cancer, glioma, melanoma and other solid tumors.

16. The method of claim 14, further comprising administering to the human subject an effective amount of one or more of other medications.

17. A method for detecting the presence of CD47 protein in a sample, comprising:
   (a) contacting the samples with the antibody or antigen-binding fragment thereof according to claim 1; and
   (b) detecting formation of a complex between the antibody or antigen-binding fragment thereof and the CD47 protein.

18. A method for determining the efficacy of a tumor therapy, comprising determining the number of the CD47-expressing cancer cells in a sample from a subject before and after the therapy, wherein the decreased number of the CD47-expressing cancer cells after the therapy indicates that the therapy is effective.

19. A pharmaceutical composition, comprising the anti-CD47 antibodies or antigen-binding fragments thereof according to claim 12, and pharmaceutical carriers.

20. A method for detecting the presence of CD47 protein in a sample, comprising:
   (a) contacting the sample with the antibody or antigen-binding fragment thereof according to claim 12; and
   (b) detecting formation of a complex between the antibody or antigen-binding fragment thereof and the CD47 protein.

* * * * *